(12) United States Patent
Steitz et al.

(10) Patent No.: US 7,504,486 B2
(45) Date of Patent: Mar. 17, 2009

(54) DETERMINATION AND USES OF THE ATOMIC STRUCTURES OF RIBOSOMES AND RIBOSOMAL SUBUNITS AND THEIR LIGAND COMPLEXES

(75) Inventors: Thomas A. Steitz, Branford, CT (US); Peter B. Moore, North Haven, CT (US); Nenad Ban, Zürich (CH); Poul Nissen, Aarhus N (DK); Jeffrey Hansen, New Haven, CT (US)

(73) Assignee: Yale University, New Haven, CT (US)

( * ) Notice: Subject to any disclaimer, the term of this patent is extended or adjusted under 35 U.S.C. 154(b) by 748 days.

(21) Appl. No.: 10/391,289

(22) Filed: Mar. 17, 2003

(65) Prior Publication Data

US 2003/0232779 A1 Dec. 18, 2003

Related U.S. Application Data

(62) Division of application No. 09/635,708, filed on Aug. 9, 2000, now Pat. No. 6,638,908.

(51) Int. Cl.
C07K 1/14 (2006.01)
G01N 31/00 (2006.01)

(52) U.S. Cl. .......................... 530/412; 436/4
(58) Field of Classification Search .................. None
See application file for complete search history.

(56) References Cited

U.S. PATENT DOCUMENTS

| | | | |
|---|---|---|---|
| 5,180,719 A | 1/1993 | White et al. |
| 5,281,703 A | 1/1994 | White et al. |
| 5,336,768 A | 8/1994 | Albrecht et al. |
| 5,466,681 A | 11/1995 | Krivan et al. |
| 5,693,791 A | 12/1997 | Truett |
| 5,866,549 A | 2/1999 | Or et al. |
| 5,905,144 A | 5/1999 | Truett |
| 6,380,356 B1 | 4/2002 | Griffin et al. |
| 6,437,119 B1 | 8/2002 | Truett |
| 6,446,032 B1 | 9/2002 | Schimmel |
| 6,468,979 B1 | 10/2002 | Pellacini et al. |
| 6,638,908 B1 | 10/2003 | Steitz et al. |
| 6,939,848 B2 | 9/2005 | Steitz et al. |
| 6,947,844 B2 | 9/2005 | Steitz et al. |
| 6,947,845 B2 | 9/2005 | Steitz et al. |
| 6,952,650 B2 | 10/2005 | Steitz et al. |
| 2002/0022257 A1 | 2/2002 | Suh et al. |
| 2002/0086308 A1 | 7/2002 | Steitz et al. |
| 2002/0188108 A1 | 12/2002 | Noller et al. |
| 2003/0027315 A1 | 2/2003 | Yonath et al. |
| 2004/0137518 A1 | 7/2004 | Lambert et al. |
| 2005/0234227 A1 | 10/2005 | Steitz et al. |
| 2005/0272681 A1 | 12/2005 | Steitz et al. |
| 2006/0136146 A1 | 6/2006 | Steitz et al. |

FOREIGN PATENT DOCUMENTS

EP 1 172 374 A2 1/2002
EP 1 186 614 A2 3/2002
EP 1 188 769 A2 3/2002
WO WO 95/07271 3/1995
WO WO 96/18633 6/1996
WO WO 97/35195 9/1997
WO WO-9957253 11/1999
WO WO 99/63937 A3 12/1999
WO WO 00/32619 A1 6/2000
WO WO 01/80863 A1 11/2001

OTHER PUBLICATIONS

Giege et al. Crystallogenesis of Biological Macromolecules: Facts and Perspectives. Acta Cryst. 1994. D50: 339-350.*
Weber, P.C., Overview of Crystallization Methods. Methods in Enzymology, 1997, vol. 276, pp. 13-22.*
Drenth, "Principles of Protein X-Ray Crystallography", 2nd Edition, 1999 Springer-Verlag New York Inc., Chapter 1, pp. 1-21.*
Szymanski et al., 5S rRNA: Structure and Interactions. Biochemical Journal. 2003. vol. 371, pp. 641-651.*
Cudney R. Protein Crystallization and Dumb Luck. The Rigaku Journal. 1999. vol. 16, No. 1, pp. 1-7.*
Kundrot, C.E. Which Strategy for a Protein Crystallization Project? Cellular Molecular Life Science. 2004. vol. 61, pp. 525-536.*
Yonath et al., Crystallographic and Image Reconstruction Studies on Ribosomal Particles from Bacterial Sources. Methods in Enzymology. 1988. vol. 164, pp. 95-117.*
Glotz et al. Three-Dimensional Crystals of Ribosomes and Their Subunits from Eu- and Archaebacteria. Biochemistry International. 1987. vol. 15, No. 5, pp. 953-960.*
Benevenuti et al., Crystallization of Soluble Proteins in Vapor Diffusion for X-ray Crystallography, Nature Protocols, published on-line Jun. 28, 2007, 2(7):1633-1651.*
McPherson, A. Current Approaches to Macromolecular Crystallization. European Journal of Biochemistry. 1990. vol. 189, pp. 1-23.*
Agalarov, S,. et al., (2000) "Structure of the S15, S6, S18-rRNA Complex: Assembly of the 30S Ribosome Central Domain," *Science* vol. 288, pp. 107-112.
Agrawal, R., et al., (1998) "Visualization of Elongation Factor G on the *Escherichia coli* 70S Ribosome: The Mechanism of Translocation," *Proc. Natl. Acad. Sci.* USA vol. 95, pp. 6134-6138.
Ban, N., et al., (2000) "The Complete Atomic Structure of the Large Ribosomal Subunit at 2.4 Å Resolution," *Science* vol. 289, No. 5481, pp. 821-1096.

(Continued)

*Primary Examiner*—Suzanne M. Noakes
(74) *Attorney, Agent, or Firm*—Goodwin Procter LLP

(57) ABSTRACT

The present invention provides methods for producing high resolution crystals of ribosomes and ribosomal subunits as well as the crystals produced by such methods. The x-ray diffraction patterns of the crystals provided by the present invention are of sufficiently high resolution for determining the three-dimensional structure of ribosomes and ribosomal subunits, for identifying ligand binding sites on ribosomes and ribosomal subunits, and for molecular modeling of ligands which interact with ribosomes and ribosomal subunits. The present invention provides methods for identifying ribosome-related ligands and methods for designing ligands with specific ribosome-binding properties. Thus, the methods of the present invention may be used to produce ligands which are designed to kill or inhibit any specific target organism(s).

2 Claims, 23 Drawing Sheets
(22 of 23 Drawing Sheet(s) Filed in Color)

OTHER PUBLICATIONS

Ban, N., et al., (1999) "Placement of Protein and RNA Structures into a 5 Å-Resolution Map of the 50S Ribosomal Subunit," *Nature* vol. 400, pp. 841-847.

Ban, N., et al., (1998) "A 9 Å Resolution X-Ray Crystallographic Map of the Large Ribosomal Subunit," *Cell* vol. 93, pp. 1105-1115.

Baranov, P., et al., (1998) "The Database of Ribosomal Cross Links (DRC)," *Nucleic Acids Research* vol. 26, No. 1, pp. 187-189.

Brodersen, D., et al., (2000) "The Structural Basis for the Action of the Antibiotics Tetracycline, Pactamycin, and Hygromycin B on the 30S Ribosomal Subunit," *Cell* vol. 103, pp. 1143-1154.

Brünger, A., et al., (1998) "Crystallography & NMR System: A New Software Suite for Macromolecular Structure Determination," *Acta Cryst*, vol. D54, pp. 905-921.

Brënger, A., (1997) "Patterson Correlation Searches and Refinement," *Methods in Enzymology*, vol. 276, pp. 558-580.

Carter, A., et al., (2001) "Crystal Structure of an Initiation Factor Bound to the 30S Ribosomal Subunit," *Science* vol. 291, pp. 498-501.

Carter, A., et al., (2000) "Functional Insights from the Structure of the 30S Ribosomal Subunit and It's Interactions with Antibiotics," *Nature* vol. 407, pp. 340-348.

Cate, J., et al., (1999) "X-Ray Crystal Structures of 70S Ribosome Functional Complexes," *Science* vol. 285, No. 5, pp. 2095-2104.

Clemons, W. Jr., et al., (1999) "Structure of a Bacterial 30S Ribosomal Subunit at 5.5 Å Resolution," *Nature* vol. 400, pp. 833-840.

Culver, G., et al., (1999) "Identification of an RNA-Protein Bridge Spanning the Ribosomal Subunit Interface," *Science* vol. 285, pp. 2133-2135.

Dahlberg, A., et al., (2001) "The Ribosome in Action," *Science* vol. 292, pp. 868-869.

Davies, C. et al., (1998) "Ribosomal Proteins S5 and L6: High-Resolution Crystal Structures and Roles in Protein Synthesis and Antibiotic Resistance," *Journal of Molecular Biology*, vol. 279, pp. 873-888.

Douthwaite, S., et al., (1995) "Recognition Determinants for Proteins and Antibiotics within 23S rRNA," *Biochem. Cell Biol*, vol. 73, pp. 1179-1185.

Douthwaite, S., et al., (1993) "Erythromycin Binding is Reduced in Ribosomes with Conformational Alterations in the 23 S rRNA Peptidyl Transferase Loop," *Journal Mol. Biol*, vol. 232, pp. 725-731.

Douthwaite, (1992) "Functional Interactions within 23S rRNA Involving the Peptidyltransferase Center," *Journal of Bacteriology* vol. 174, No. 4, pp. 1333-1338.

Fitzhugh, A., et al., (1998) "Antibiotic Inhibitors of the Peptidyl Transferase Center. I. Clindamycin as a Composite Analogue of the Transfer RNA Fragments L-Pro-Met and the D-Ribosyl Ring of Adenosine," *Bioorganic and Medicinal Chemistry Letters*, vol. 8, pp. 87-92.

Gabashvili, I., et al., (2000) "Solution Structure of the *E coli* 70S Ribosome at 11.5 Å Resolution," *Cell*, vol. 100, pp. 537-549.

Garrett, R., et al., (1996) "The Peptidyl Tranferase Center," *Ribosomal RNA* pp. 327-355.

Garza-Ramos, G. et al., (2001) "Binding Site of Macrolide Antibiotics on the Ribosome: New Resistance Mutation Identifies a Specific Interaction of Ketolides with rRNA," *Journal of Bacteriology*, vol. 183, No. 23, pp. 6898-6907.

Gonzales, R., et al., (2001) "Infections Due to Vancomycin-Resistant *Enterococcus faecium* Resistant to Iinezolid," *The Lancet* vol. 357, p. 1179.

Green, R., et al., (1997) "Ribosomes and Translation," *Annu. Rev. Biochemistry* vol. 66, pp. 679-716.

Gregory, S., et al., (1999) "Erythromycin Resistance Mutations in Ribosomal Proteins L22 and L4 Perturb the Higher Order Structure of 23 S Ribosomal RNA," *J. Mol. Biol.* vol. 289, pp. 827-834.

Gschwend, D. et al., (1996) "Molecular Docking Towards Drug Discovery," *Journal of Molecular Recognition*, vol. 9, pp. 175-186.

Guetell, R. (1996) "Comparative Sequence Analysis and the Structure of 16S and 23S rRNA," *Ribosomal RNA* pp. 111-128.

Hansen, H.A.S., et al., (1990) "Crystals of Complexes Mimicking Protein Biosynthesis are Suitable for Crystallographic Studies," *Bioclumica et Biophysica Acta*. vol. 1050, pp. 1-7.

Harms, J., et al., (2001) "High Resolution Structure of the Large Ribosomal Subunit from a Mesophilic Eubacterium," *Cell*, vol. 107, pp. 679-688.

Harms, J., et al., (1999) "Elucidating the Medium-Resolution Structure of Ribosomal Particles: an Interplay between Electron Cryo-Microscopy and X-ray Crystallography," *Structure* vol. 7, No. 8, pp. 931-941.

Hansen, L., et al., (1999) "The Macrolide-Ketolide Antibiotic Binding Site is Formed by Structures in Domains II and V of 23S Ribosomal RNA," *Molecular Microbiology*, vol. 31, No. 2, pp. 623-631.

Kloss, P., et al., (1999) "Resistance Mutations in 23 S rRNA Identify the Site of Action of the Protein Synthesis Inhibitor Linezolid in the Ribosomal Peptidyl Transferase Center," *J. Mol. Biol.* vol. 294, No. 1, pp. 93-101.

Lázaro, E., et al., (1996) "A Sparsomycin-Resistant Mutant of *Halobacterium salinarium* Lacks a Modification at Nucleotide U2603 in the Peptidyl Transferase Centre of 23 S rRNA," *J. Mol. Biol.* vol. 261, No. 2, pp. 231-238.

Lázaro, E., et al., (1991) "Chemical, Biochemical and Genetic Endeavors Characterizing the Interaction of Sparsomycin with the Ribosome," *Biochimic* vol. 73, pp. 1137-1143.

Lipinski, C., et al., (1997) "Experimental and Computational Approaches to Estimate Solubility and Permeability in Drug Discovery and Development Settings," *Adv. Drug Delivery Rev.* vol. 23, No. 3-25.

Maskowski et al., (1987) "Single Crystals of Large Ribosomal Particles from *Halobacterium marismortui* Diffract to 6 Å," *Journal Molecular Biology* vol. 193 pp. 818-822.

Matadeen, R., et al., (1999) "The *Escherichia coli* Large Ribosomal Subunit at 7.5 Å Resolution," *Structure*, vol. 7, No. 12, pp. 1575-1583.

Moazed et al., (1989) "Interaction of +RNA with 23S rRNA in the Ribosomal A, P, and E Sites," *Cell* vol. 57, pp. 585-597.

Moore, P.B. (1999) "Structural Motifs in RNA," *Annu. Rev. Biochemistry* vol. 67, pp. 287-300.

Moore, P.B. (1998) "The Three-Dimensional Structure of the Ribosome and its Components," *Annu. Rev. Biophys.* vol. 27, pp. 35-58.

Mueller, F., et al., (2000) "The 3D Arrangement of the 23 S and 5 S rRNA in the *Escherichia coli* 50 S Ribosomal Subunit Based on a Cryo-Electron Microscopic Reconstruction at 7.5 Å Resolution," *Journal Molecular Biology* vol. 298, pp. 35-59.

Mussig, J., et al., (1989) "Crystals of Wild-type, Mutated, Derivatized and Complexed 50 S Ribosomal Subunits from *Bacillus stearothermophilus* Suitable for X-ray Analysis," *J. Mol Biol.* vol. 205, pp. 619-621.

Nakatogawa, H., et al., (2002) "The Ribosomal Exit Tunnel Functions as a Discriminating Gate," *Cell* vol. 108, pp. 529-636.

Navaza, J., et al., (1997) "AMoRe: An Automated Molecular Replacement Program Package," *Methods in Enzymology* vol. 276, 581-595.

Nissen, P., et al., (2000) "The Structural Basis of Ribosome Activity in Peptide Bond Synthesis," *Science* vol. 289, pp. 920-930.

Nitta, J., et al., (1998) "Reconstitution of Peptide Bond Formation with *Escherichia coli* 23S Ribosomal RNA Domains," *Science* vol. 281, pp. 666-669.

Noller, H., (1991) "Ribosomal RNA and Translation," *Ann. Rev. Biochemistry* vol. 60, pp. 191-227.

Ogle, J., et al., (2001) "Recognition of Cognate Transfer RNA by the 30S Ribosomal Subunit," *Science* vol. 292, pp. 897-902.

Pestka, S., (1974) "Antibiotics as Probes of Ribosome Structure: Binding of Chloramphenicol and Erythromycin to Polyribosomes: Effect of Other Antibiotics," *Antimicrobial Agents and Chemotherapy* vol. 5, No. 3, pp. 255-267.

Porse, B., et al., (1999) "Ribosomal Mechanics, Antibiotics, and GTP Hydrolysis," *Cell* vol. 97, pp. 423-426.

Porse, B., et al., (1999) "Sites of Interaction of Streptogramin A and B Antibiotics in the Peptidyl Transferase Loop of 23 S rRNA and the Synergism of Their Inhibitory Mechanisms," *J. Mol. Biol.* vol. 286, No. 2, pp. 375-387.

Ramakrishnan, V., (2002) "Ribosome Structure and the Mechanism of Translation," *Cell* vol. 108, pp. 557-572.

Ramakrishnan, V., et al., (1995) "Structures of Prokaryotic Ribosomal Proteins: Implications for RNA Binding and Evolution," *Biochem. Cell Biol.* vol. 73, pp. 979-986.

Rodriguez-Fonseca, C., et al., (1995) "Fine Structure of the Peptidyl Transferase Centre on 23 S-like rRNAs Deduced from Chemical Probing of Antibiotic-Ribosome Complexes," *J. Mol. Biol.* vol. 247, pp. 224-235.

Schlünzen, F., et al., (2001) "Structural Basis for the Interaction of Antibiotics with the Peptidyl Transferase Centre in Eubacteria," *Nature* vol. 413, pp. 814-821.

Schlünzen, F., et al., (2000) "Structure of Functionally Activated Small Ribosomal Subunit at 3.3 Å Resolution," *Cell* vol. 102, pp. 615-623.

Schlünzen, F., et al., (1995) "A Milestone in Ribosomal Crystallography: The Construction of Preliminary Electron Density Maps at Intermediate Resolution," *Biochemistry Cell Biology* vol. 73, pp. 739-749.

Shinabarger, D., et al., (1997) "Mechanism of Action of Oxazolidinones: Effects of Linezolid and Eperezolid on Translation Reactions," *Antimicrobial Agents and Chemotherapy* vol. 41, No. 10, pp. 2132-2136.

Spahn, C.M.T., et al., (1995) "Throwing a Spanner in the Works: Antibiotics and the Translation Apparatus," *Journal of Molecular Medicine*, vol. 74, No. 8, pp. 423-439.

Swaney, S., et al., (1998) "The Oxazolidinone Linezolid Inhibits Initiation of Protein Synthesis in Bacteria," *Antimicrobial Agents and Chemotherapy* vol. 42, No. 12, pp. 3251-3255.

Tenson, T., et al., (2002) "Regulatory Nascent Peptides in the Ribosomal Tunnel," *Cell* vol. 108, pp. 591-594.

Timmermans, P., et al., (1982) "Sparsophenicol: A New Synthetic Hybrid Antibiotic Inhibiting Ribosomal Peptide Synthesis" *J. Med. Chem.* vol. 25, pp. 1123-1125.

Tocilj, A., et al., (1999) "The Small Ribosomal Subunit from *Thermus thermophilus* at 4.5 Å Resolution: Pattern Fittings and the Identification of a Functional Site," *Proc. Natl. Acad. Sci. USA* vol. 96, pp. 14252-14257.

Trakhanov, S.D., et al., (1987) "Crystallization of 70 S Ribosomes and 30 S Ribosomal Subunits from *Thermus thermophilis*," *Febs Letters.* vol. 220, No. 2, pp. 319-322.

Tronrud, D., (1997) "TNT Refinement Package," *Macromolecular Crystallography, Part B, Methods in Enzymology*, vol. 277, pp. 306-319.

Tsiodras, S., et al., (2001) "Linezolid Resistance in a Clinical Isolate of *Staphylococcus aureus*," *The Lancet* vol. 358, pp. 207-208.

Vannuffel et al., (1996) "Mechanism of Action of Streptogramins and Macrolides," *Drugs* vol. 51, Suppl I, pp. 20-30.

Vannuffel et al., (1992) "Identification of a Single Base Change in Ribosomal RNA Leading to Erythromycin Resistance," *The Journal of Biological Chemistry* vol. 267(12), pp. 8377-8382.

Vester et al., (2001) "Macrolide Resistance Conferred by Base Substitutions," *Antimicrobial Agents and Chemotherapy* vol. 45, No. 1, pp. 1-12.

Vester et al., (1988) "The Importance of Highly Conserved Nucleotides in the Binding Region of Chloramphenicol at the Peptidyl transfer Centre of *Escherichia coli* 23S Ribosomal RNA," *The EMBO Journal* vol. 7, No. 11, pp. 3577-3587.

Volkmann et al., (1990) "Characterization and Preliminary Crystallographic Studies on Large Ribosomal Subunits from *Thermus thermophilus*," *J. Mol. Biol.* vol. 216, pp. 239-241.

Von Bohlen, (1991) "Characterization and Preliminary Attempts for Derivatization of Crystals of Large Ribosomal Subunits from *Haloarcula marismortui* Diffracting to 3 Å Resolution," *Journal Molecular Biology* vol. 222, pp. 11-15.

Welch, M., et al., (1997) "23S rRNA Similarity from Selection for Peptidyl Transferase Mimicry," *Biochemistry* vol. 36, pp. 6614-6623.

Welch, M., et al., (1995) "An Inhibitor of Ribosomal Peptidyl Transferase Using Transition-State Analogy," *Biochemistry* vol. 34, pp. 385-390.

Wimberly, B., et al., (2000) "Structure of the 30S Ribosomal Subunit," *Nature* vol. 407, pp. 327-339.

Wittmann et al., (1982) "Crystallization of *Escherichia coli* Ribosomes," *Febs Letters* vol. 146, No. 1, pp. 217-220.

Wool, I., et al., (1995) "Structure and Evolution of Mammalian Ribosomal Proteins," *Biochemistry Cell Biology* vol. 73, pp. 933-947.

Xiong, L., et al., (2000) "Oxazolidinone Resistance Mutations in 23s rRNA of *Escherichia coli* Reveal the Central Region of Domain V as the Primary Site of Drug Action," Journal of Bacteriology vol. 182, No. 19, pp. 5325-5331.

Yonath, A., et al., (1998) "Crystallographic Studies on the Ribosome, a Large Macromolecular Assembly Exhibiting Severe Nonisomorphism, Extreme Beam Sensitivity and No Internal Symmetry," *Acta Cryst.* vol. A54, pp. 945-955.

Yonath, A., et al., (1986) "Characterization of Single Crystals of the Large Ribosomal Particles from *Bacillus stearothermophilus*," *J. Mol. Biol.* vol. 187, pp. 633-636.

Yusupova, G., et al., (2001) "The Path of Messenger RNA through the Ribosome," *Cell* vol. 106, pp. 233-241.

Yusupov, M., et al., (2001) "Crystal Structure of the Ribosome 5.5 Å Resolution," *Science* vol. 292, pp. 883-896.

Yusupov, M., et al., (1991) "*Thermus thermophilus* Ribosomes for Crystallographic Studies," *Biochimie* vol. 73, pp. 887-897.

Zemlicka, J., et al., (1993) "Hybrids of Antibiotics Inhibiting Protein Synthesis, Synthesis and Biological Activity," *J. Med. Chem.* vol. 36, pp. 1239-1244.

European Search Report for Application No. 01306825.9 dated May 24, 2002.

Hansen et al. (2002) "Structural Insights into Peptide Bond Formation," *Proc. Natl. Acad. Sci. USA*, 99(18):11670-11675.

Hansen et al. (2002) "The Structures of Four Macrolide Antibiotics Bound to the Large Ribosomal Subunit," *Molecular Cell*, 10:117-128.

Klein et al., "The Kink-Turn: A New RNA Secondary Structure Motif," *EMBO J.*, 20(15):4214-4221 (2001).

Nissen et al., "RNA Tertiary Interactions in the Large Ribosomal Subunit: The A-Minor Motif," *Proc. Natl. Acad. Sci. USA*, 98(9):4899-4903 (2001).

Schmeing et al., "A Pre-Translocational Intermediate in Protein Synthesis Observed in Crystals of Enzymatically Active 50S Subunits," *Nature Struct. Biol.*, 9(3):225-230 (2002).

Drenth, "Principles of Protein X-ray Crystallography," 1994. Springer-Verlag, pp. 1-18.

Franceshi et al. (1993) "Towards Atomic Resolution of Prokaryotic Ribosomes: Crystallographic, Genetic and Biochemical Studies" in *The Translational Apparatus* 397-410.

Hope et al. (1989) "Cryocrystallography of Ribosomal Particles" *Acta. Cryst.* B45: 190-199.

Shevack et al. (1985) "Characterization and Crystallization of Ribosomal Particles from *Halobacterium marismortui*" *FEBS Letters* 184(1): 68-71.

Yonath et al. (1980) "Crystallization of the Large Ribosomal Subunits from *Bacillus stearothermophilus*" *Biochem. Intern'l.* 1(5): 428-435.

Yonath et al. (1984) "Some X-ray Diffraction Patterns from Single Crystals of the Large Ribosomal Subunit from *Bacillus stearothermophilus*" *J. Mol. Biol.* 177: 201-206.

Yonath et al. (1988) "Crystallography of Ribosomal Particles" *J. Cryst. Growth* 90: 231-244.

Fourmy et al. (1996) "Structure of the A Site of *Escherichia coli* 16S Ribosomal RNA Complexed with an Aminoglycoside Antibiotic" *Science* 274(5291):1367-1371.

Hermann et al. (1999) "Docking of Cationic Antibiotics to Negatively Charged Pockets in RNA Folds" *J. Med. Chem.* 42(7):1250-1261.

Ioannou et al. (1998) "Kinetics of Inhibition of Rabbit Reticulocyte Peptidyltransferase by Anisomycin and Sparsomycin" *Molecular Pharmacology* 53(6):1089-1096.

Kirillov et al. (1999) "Peptidyl Transferase Antibiotics Perturb the Relative Positioning of the 3'-Terminal Adenosine of P/P'-Site-Bound tRNA and 23S rRNA in the Ribosome" *RNA* 5(8): 1003-1013.

Spickler et al. (1997) "Streptomycin Binds to the Decoding Center of 16 S Ribosomal RNA" *J. Mol. Biol.* 273(3):586-599.

Wong et al. (1998) "Specificity of Aminoglycoside Antibiotics for the A-Site of the Decoding Region of Ribosomal RNA" *Chemistry & Biology* 5(7):397-406.

European Search Report for Application No. 02255442.2 dated Mar. 6, 2003.

Hanessian et al. (1984) "Quantamycin': A Computer-Simulated New-Generation Inhibitor of Bacterial Ribosomal Binding" *Journal American Chemical Society* 106:6114-6115.

Vince et al. (1975) "Chloramphenicol Binding Site with Analogues of Chloramphenicol and Puromycin" *Antimicrobial Agents and Chemotherapy* 8(4):439-443.

Shuker et al. (1996) "Discovering High-Affinity Ligands for Proteins: SAR by NMR" *Science* 274(5292):1531-1541.

Hecker et al. (1993) "Application of Hygromycin A Structure Activity Relationships to the Antibiotic A201A" *Bioorganic & Medicinal Chemistry Letters* 3(2):295-298.

Wang et al. (1997) "Dimeric Aminoglycoside: Design, Synthesis and RNA Binding" *Bioorganic & Medicinal Chemistry Letters* 7(14):1951-1956.

Holmes et al. (1993) "Novel Dimeric Penicillin Derived Inhibitors of HIV-1 Proteinase: Interactions with the Catalytic Aspartates" *Bioorganic & Medicinal Chemistry Letters* 3(4):503-508.

Rao et al. (1997) "Tight Binding of a Dimeric Derivative of Vancomycin with Dimeric L-Lys-D-Ata-D-Ala" *J. Am. Chem. Soc.* 119:10286-10290.

Tanihara et al. (1998) "Thrombin-Sensitive Peptide Linkers for Biological Signal-Responsive Drug Release Systems" *Peptides* 19(3):421-425.

Hansen et al. (2003) "Structures of Five Antibiotics Bound at the Peptidyl Transferase Center of the Large Ribosomal Subunit" *J. Mol. Biol.* 330, 1061-1075.

Di Giambattista, M., et al., (1990) "Affinity Labeling of the Virginiamycin S. Binding Site on Bacterial Ribosome," *Biochemistry* vol. 29, pp. 9203-9211.

Moazed, D., et al., (1987) "Chloramphenicol, Erythromycin, Carbomycin and Vernamycin B Protect Overlapping Sites in the Peptidyl Transferase Region of 23S Ribosomal RNA," *Biochimie* vol. 69, pp. 879-884.

Carlson et al. (2000) "Accomodating Protein Flexibility in Computational Drug Design," Molec. Pharm. 57:213-218.

Dube et al. (1998) "The 80S rat liver ribosome at 25 A resolution by electron cryomicroscopy and angular reconstitution," Structure 6: 389-399.

Flower (2002) Drug Design and Citting Edge Approaches, The Royal Society of Chemistry, p. 21-27.

Hegyi et al. (1999) "The Relationship Between Protein Structure and Function: A Comprehensive Survey with Application to the Yeast Genome," J. Mol. Biol. 288: 147-164.

Malhotra et al. (1998) "*Escherichia coli* 70 S Ribosome at 15 A Resolution by Cryo-electron Microscopy: Localization of fMet-tRNA and Fitting of L1 Protein," J. Mol. Biol. 280: 103-116.

Shevack et al. (1985) "Characterization and Crystallization of Ribosomal Particles from *Halobacterium marismortui*," FEBS Letters 84: 68-71.

* cited by examiner

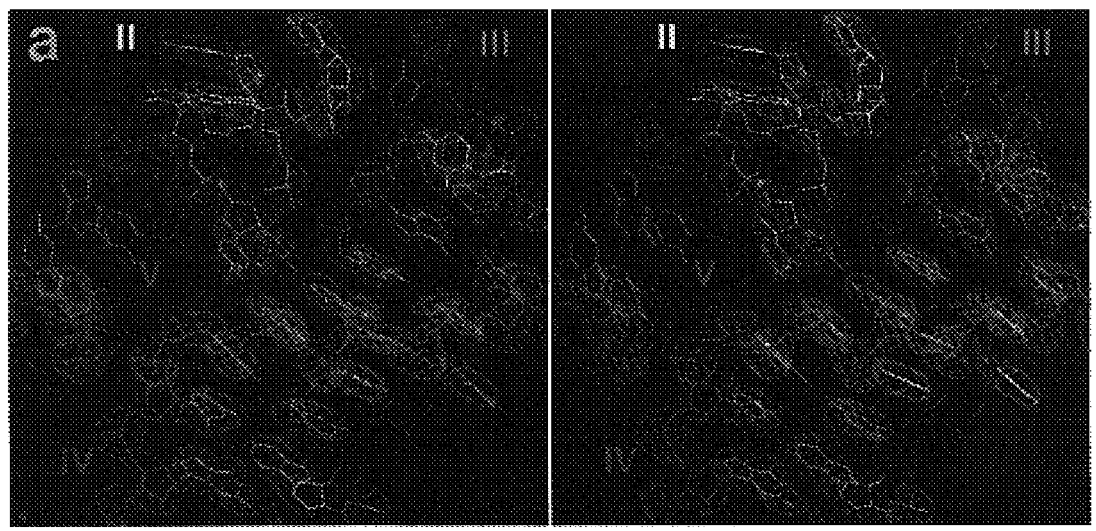
FIG. 1a
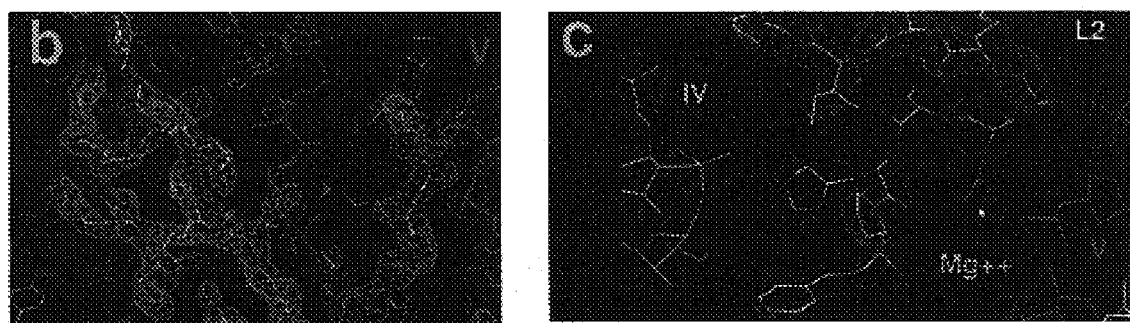
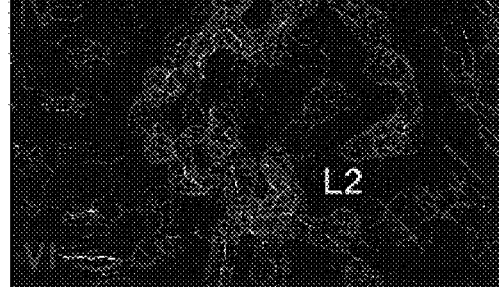
FIG. 1b
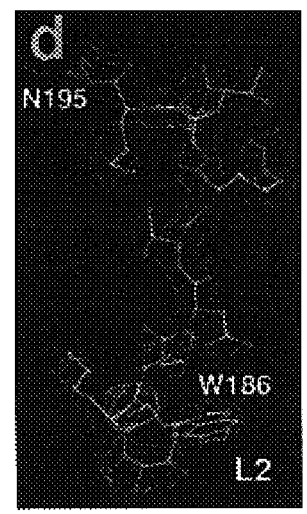
FIG. 1c
FIG. 1d

Secondary Structure: large subunit ribosomal RNA - 3' half

*Haloarcula marismortui* rrnB
(AF034620)
1.Archaea 2.Euryarchaeota 3.Halobacteriales
4.Halobacteriaceae 5.Haloarcula N-amino-acylated Minihelix Peptidyl-transferase Intermediate CCdAp-Puromycin

DETERMINATION AND USES OF THE ATOMIC STRUCTURES OF RIBOSOMES AND RIBOSOMAL SUBUNITS AND THEIR LIGAND COMPLEXES

RELATED APPLICATIONS

This application is a divisional of U.S. Serial No. 09/635,708, filed Aug. 9, 2000, which issued as U.S. Pat. No. 6,638,908 B1 on Oct. 28, 2003, the entire disclosure of which is incorporated by reference herein.

ACKNOWLEDGMENT OF FEDERAL SUPPORT

This work was at least partially funded by the following NIH grants: NIH-GM22778 and NIH-GM54216.

FIELD OF THE INVENTION

The present invention generally pertains to the fields of molecular biology, protein crystallization, x-ray diffraction analysis, three-dimensional structural determination, structure based rational drug design and molecular modeling of ribosomes and ribosomal subunits. The present invention provides crystallization methods as well as the crystallized ribosome and ribosomal subunits. The x-ray diffraction patterns of the crystals in question are of sufficient resolution so that the three-dimensional structure of ribosomes and ribosomal subunits can be determined at atomic resolution, ligand binding sites on ribosomes and ribosomal subunits can be identified, and the interactions of ligands with ribosomes and ribosomal subunits can be modeled in specific ways.

The high resolution ribosome and ribosomal subunit maps provided by the present invention and the models prepared using such maps permit the design of ligands which can function as active agents. Thus, the present invention has applications to the design of active agents which include, but are not limited to, those that find use as antifungals, insecticides, herbicides, miticides, antibacterials, antiprotozoals and rodenticides.

BACKGROUND

Ribosomes: Structures, Function, and Composition

Ribosomes are ribonucleoproteins which are present in both prokaryotes and eukaryotes. They consist of about two-thirds RNA and one-third protein. Ribosomes are essential for protein synthesis. In the last step of the gene expression pathway, ribosomes translate the genomic information encoded in a messenger RNA into protein (Garrett, et al., 2000).

Ribosomes are complexes of two nonequivalent ribonucleoprotein subunits. The larger subunit ("large ribosomal subunits") is about twice the size of the smaller ("small ribosomal subunits"). The small ribosomal subunit binds mRNA and mediates the interactions between mRNA and tRNA anticodons on which the fidelity of translation depends. The large ribosomal subunit catalyzes peptide bond formation—the peptidyl-transferase reaction of protein synthesis—and includes two different tRNA sites: the A site for the incoming aminoacyl-tRNA, which is to contribute its amino acid to the growing peptide chain, and the P site for peptidyl-tRNA complex, i.e. the tRNA linked to all the amino acids that have so far been added to the peptide chain. The large ribosomal subunit also includes a binding site for G-protein factors that assist in the initiation, elongation, and termination phases of protein synthesis. The large and small ribosomal subunits behave independently during the initiation phase of protein synthesis; however, they assemble into complete ribosomes when elongation is about to begin.

The molecular weight of the prokaryotic ribosome is about $2.6 \times 10^6$. In prokaryotes, the small ribosomal subunit contains a 16S (Svedberg units) rRNA having a molecular weight of about $5.0 \times 10^5$. The large ribosomal subunit contains a 23S rRNA having a molecular weight of about $1.0 \times 10^6$ and a 5S rRNA having a molecular weight of about $4.0 \times 10^5$. The prokaryotic small subunit contains 21 different proteins and its large subunit, 31 proteins. The large and small ribosomal subunits together make a 70S ribosome in procaryotes.

Eukaryotic ribosomes are bigger than their prokaryotic counterparts. The large and small subunits together make an 80S eukaryotic ribosome. The small subunit of an eukaryotic ribosome includes a single 18S rRNA, while the large subunit includes a 5S rRNA, a 5.8S rRNA, and a 28S rRNA. The 5.8S rRNA is structurally related to the 5' end of the prokaryotic 23S rRNA and the 28S rRNA is structurally related to the rest (Moore, 1998). Eukaryotic ribosomal proteins are qualitatively similar to the prokaryotic ribosomal proteins; however, the eukaryotic proteins are bigger and there are more of them (Moore, 1998).

Structural Conservation of the Large Ribosomal Subunit

While the chemical composition of large ribosomal subunits varies significantly from species to species, the sequences of their components provide unambiguous evidence that they are similar in three-dimensional structure, function in a similar manner, and are related evolutionarily. The evolutionary implications of the rRNA sequences data available is reviewed in the articles of Woese and others in part II of "*Ribosomal RNA. Structure, Evolution, processing and Function in Protein Biosynthesis*", Zimmermann and Dahlberg, eds, CRC Press, Boca Raton, Fla., 1996. The article by Garret and Rodriguez-Fonseca in part IV of the same volume discusses the unusually high level of sequence conservation observed in the peptidyl transferase region of the large ribosomal subunit. Archeal species like *H. marismortui* have ribosomes that resemble those obtained from eubacterial species like *E. coli* in size and complexity. However, the proteins in their ribosomes are more closely related to the ribosomal proteins found in eukaryotes (Wool, I., Chan, Y.-L., & Gluck, A., Biochem. Cell Biol. 73, 933-947 (1995)).

Because of the high level of sequence conservation that characterizes the active site regions of ribosomes from different species, knowledge of the three-dimensional structure of a large ribosomal subunit from a single species belonging to a single kingdom, e.g. that of *H. marismortui*, will enable those skilled in the art both to understand the function of the critical regions of ribosomes from other species, regardless of kingdom. Thus it should be possible to for such an individual to produce useful models for the functionally significant regions of the ribosomes of higher organisms like humans and of the ribosomes from the bacteria that are their pathogens, and to understand how they might differ.

Determination of the Structure of Ribosomes

Much is what is known about ribosome structure derives from physical and chemical methods that produce relatively low-resolution information. Electron microscopy (EM) has contributed to the understanding of ribosome structure ever since the ribosome was discovered. In the 1970s, low resolution EM revealed the shape and quaternary organization of the ribosome. By the end of 1980s, the positions of the surface epitopes of all the proteins in the *E. coli* small subunit, as well as many in the large subunit, had been mapped using immunoelectron microscopy techniques (Oakes et al., 1986; Stoeffler et al., 1986). In the last few years, advances in single-particle cryo-EM and image reconstruction have led to three dimensional reconstructions of the *E. coli* 70S ribosome and its complexes with tRNAs and elongation factors at resolutions between 15 Å and 25 Å (Stark et al., 1995; Frank et al., 1995; Stark et al., 1997a; Agrawal et al., 1996; Stark et al., 1997b). Additionally, three-dimensional, electron microscopic images of the ribosome have been produced at resolutions sufficiently high so that many of the proteins and nucleic acids that assist in protein synthesis can be visualized bound to the ribosome (Agrawal et al., 2000), and earlier this year an approximate model of the RNA structure in the large subunit was constructed to fit a 7.5 Å resolution electron microscopic map of the 50S subunit from *E. coli* as well as biochemical data (Mueller et al., 2000).

While the insights provided by electron microscopy have been useful, it has long been recognized that a full understanding of ribosome structure would derive only from X-ray crystallography. Crystallization studies of the ribosome began two decades ago by Ada Yonath and coworkers opened the possibility of using X-ray crystallography to determine the structure of the ribosome at atomic resolution. This was a challenging enterprise. Crystals of ribosomes have been especially difficult to obtain because of their huge size and their lack of internal symmetry. Moreover, since their surface is composed of highly degradable RNA and loosely held proteins, ribosomes exhibit inherent flexibility and instability. In 1979, Yonath and Wittman obtained potentially useful crystals of ribosomes and ribosomal subunits (Yonath et al., 1980). Ribosomal crystals proved to be extremely sensitive to radiation even at cryo-temperature when using bright Synchroton X-ray beam required for high resolution data collection (Weinstein et al., 1999). They are also characterized by low level isomorphism, fluctuations in the unit cell dimensions, deformed spot-shape, and nonisotropic mosaicity (Weinstein et al., 1999). By the mid 1980s, Trakanov et al. (1987), a group in Puschino, were also preparing ribosome crystals for X-ray crystallography. Maskowski et al. (1987) were the first to obtain crystals of 50S ribosomal subunit from *Haloarcula marismortui*. In 1991, van Bohlen et al. (1991) reported an important improvement in the resolution of the diffraction data obtainable from the crystals of the 50S ribosomal subunit of *H. marismortui*.

In 1995, Schlunzen et al. (1995) reported low resolution electron density maps for the large and small ribosomal subunits from halophilic and thermophilic sources. However, the low resolution electron density maps of Schlunzen et al. (1995) are incorrect (Ban et al., 1998).

The first electron density map of the ribosome that showed features recognizable as duplex RNA was a 9 Å resolution X-ray crystallographic map of the large subunit from *Haloarcula marismortui* published two years ago (Ban et al., 1998). A year later, extension of the phasing of that map to 5 Å resolution made it possible to locate several proteins and nucleic acid sequences the structures of which had been determined independently (Ban et al., 1999).

At about the same time, using similar crystallographic strategies, a 7.8 Å resolution map was generated of the entire *T. thermophilus* ribosome showing the positions of tRNA molecules bound to its A, P, and E (protein exit site) sites (Cate et al., 1999), and a 5.5 Å resolution map of the 30S subunit from *Thermus thermophilus* was obtained that allowed the fitting of solved protein structures and the interpretation of some of its RNA features (Clemons et al., 1999). Subsequently, an independently determined, 4.5 Å resolution map of the *T. thermophilus* 30S subunit was published, which was based in part on phases calculated from a model corresponding to 28% of the subunit mass that had been obtained using a 6 Å resolution experimental map (Tocilj et al., 1999). The subunit packing interpretation of the two 30S structures is not the same, even though the crystals used by the two groups appear to be identical.

The Need for Higher Resolution to Obtain the Atomic Structure for the 50S Ribosomal Subunit Although the prior art provides crystals of the 50S ribosomal subunit and 9 Å and 5 Å resolution X-ray crystallographic maps of the structure of the 50S ribosome, the prior art crystals and X-ray diffraction data are not sufficient to establish the 3D structures of all 31 proteins and 3,043 nucleotides of 50S. Thus, the prior art crystals and maps are inadequate for the structure-based design of active agents, such as herbicides, drugs, insecticides, animal poisons, etc.

More detailed, higher resolution X-ray crystallographic maps are necessary in order to determine the location and 3D structure of the proteins and nucleotides in ribosomes and ribosomal subunits, particularly for the 50S ribosomal subunit. Such high resolution maps would enable the design of various useful active agents, such as herbicides, drugs, insecticides, animal poisons, etc.

For example, an accurate molecular structure of the 50S ribosomal subunit will not only enable further investigation and understanding of the mechanism of protein synthesis, but also the development of effective therapeutic agents and drugs that modulate (i.e., promote or inhibit) protein synthesis.

Location of the Peptidyl Transferase Site in the Large Ribosomal Subunit

It has been known for thirty-five years that the peptidyl transferase activity responsible for the peptide bond formation that occurs during messenger RNA-directed protein synthesis is intrinsic to the large ribosomal subunit (Traut et al., 1964; Rychlik, 1966; Monro, 1967; Maden et al., 1968) and it has been understood for even longer that the ribosome contains proteins as well as RNA. In bacteria, for example, the large ribosomal subunit contains ~35 different proteins and two RNAs (Noller, 1984; Wittmann-Liebold et al., 1990). These findings posed three related questions. Which of the almost 40 macromolecular components of the large ribosomal subunit contribute to its peptidyl transferase site, where is that site located in the large subunit and how does it work?

By 1980, the list of components that might be part of the ribosome's peptidyl transferase had been reduced to about half a dozen proteins and 23S rRNA (for reviews see Ofenand, 1980; Cooperman, 1980), and following the discovery of catalytic RNAs (Guerrier-Takada et al., 1983; Kruger et al., 1982), the hypothesis that 23S rRNA might be its sole constituent, which had been proposed years earlier, began to gain favor. In 1984, Noller and colleagues published affinity labeling results which showed that U2619 and U2620 (in *E. coli*: U2584, U2585) are adjacent to the CCA-end of P site-bound tRNA (Barta et al., 1984; Vester et al., 1988). These nucleotides are part of a highly conserved internal loop in the center of domain V of 23S rRNA. The hypothesis that this loop is intimately involved in the peptidyl transferase activity was supported by the observation that mutations in that loop render cells resistant to many inhibitors of peptidyl transferase, and evidence implicating it in this activity has continued to mount (see Noller, 1991; Garrett et al., 1996).

Definitive proof that the central loop in domain V is the sole component of the ribosome involved in the peptidyl transferase activity has remained elusive, however. In the 1990s, Noller and his colleagues prepared particles that retain peptidyl transferase activity by increasingly vigorous deproteinizations of large ribosomal subunits, but active particles that were completely protein-free could not be produced (Noller et al., 1999; Khaitovich et al., 1999). Nevertheless, combined with earlier reconstitution results (Franceschi et al., 1990), this work reduced the number of proteins that might be involved to just two: L2 and L3 (see Green et al., 1997). More recently, Watanabe and coworkers reported success in eliciting peptidyl transferase activity from in vitro synthesized, protein-free 23S rRNA (Nitta et al., 1998; Nitta et al., 1998), but their observations have not withstood further scrutiny (Khaitovich et al., 1999). Thus the question still remains: is the ribosome a ribozyme or is it not?

Over the years, the location of the peptidyl transferase site in the ribosome has been approached almost exclusively by electron microscopy. In the mid-1980s evidence that there is a tunnel running through the large ribosomal subunit from the middle of its subunit interface side to its back (Milligan et al., 1986; Yonath et al., 1987) began to accumulate, and there was/is strong reason to believe that polypeptides pass through it as they are synthesized (Bemabeu et al., 1982; Ryabova et al., 1988; Beckmann et al., 1997). More recent cryo-electron microscopic investigations (Frank et al., 1995; Frank et al., 1995; Stark et al., 1997; Stark et al., 1995) confirmed the existence of the tunnel and demonstrated that the CCA-ends of ribosome-bound tRNAs bound to the A- and P-sites are found in the subunit interface end of the tunnel. Consequently, the peptidyl transferase site must be located at that same position, which is at the bottom of a deep cleft in the center of the subunit interface surface of the large subunit, immediately below its central protuberance.

The substrates of the reaction catalyzed by the large subunit are an aminoacyl-tRNA (aa-tRNA) and a peptidyl-tRNA. The former bind in the ribosome's A-site and the latter in its P-site. The α-amino group of the aa-tRNA attacks the carbon of the carbonyl acylating the 3' hydroxyl group of the peptidyl-tRNA, and a tetrahedral intermediate is formed at the carbonyl carbon (FIG. 1). The tetrahedral intermediate resolves to yield a peptide extended by one amino acid esterified to the A-site bound tRNA and a deacylated tRNA in the P-site.

This reaction scheme is supported by the observations of Yarus and colleagues (Welch et al., 1995) who synthesized an analogue of the tetrahedral intermediate by joining an oligonucleotide having the sequence CCdA to puromycin via a phosphoramide group (FIG. 9). The sequence CCA, which is the 3' terminal sequence of all tRNAs, binds to the large subunit by itself, consistent with the biochemical data showing that the interactions between tRNAs and the large subunit largely depend on their CCA sequences (Moazed et al., 1991). Puromycin is an aa-tRNA analogue that interacts with the ribosomal A-site, and the phosphoramide group of their compound mimics the tetrahedral carbon intermediate. This transition state analogue, CCdA-phosphate-puromycin (CCdA-p-Puro), binds tightly to the ribosome, and inhibits its peptidyl transferase activity (Welch et al., 1995).

Structure Determination of Macromolecules using X-Ray Crystallography

Each atom in a crystal scatters X-rays in all directions, but crystalline diffraction is observed only when the crystal is oriented relative to the X-ray beam so that the atomic scattering interferes constructively. The orientations that lead to diffraction may be computed if the wavelength of the X-rays used and the symmetry and dimensions of the crystal's unit cell are known (Blundell, T. L. and Johnson, L. N., *Protein Crystallography*, 1976, Academic Press, New York ). The result is that if a film is placed behind a crystal that is being irradiated with monochromatic X-rays of an appropriate wavelength, the diffraction pattern recorded will consist of spots, each spot representing one of the orientations that gives rise to constructive interference.

Each spot in such a pattern, however it is recorded, is characterized by an intensity—its blackness—, a location, which encodes the information about diffraction orientation, and a phase. If all of those things are known about each spot in a crystal diffraction pattern, the distribution of electrons in the unit cell of the crystal may be computed by Fourier transformation (Blundell, T. L. and Johnson, L. N., supra), and from that distribution or electron density map, atomic positions can be worked out.

Unfortunately, the phase information essential for computing electron distributions cannot be measured directly from diffraction patterns. One of the methods routinely used to determine the phases of macromolecules, such as proteins and nucleic acids, is called multiple isomorphous replacement (MIR) (including heavy metal scattering), which requires the introduction of new x-ray scatterers into the unit cell of the crystal. These additions are usually heavy atoms (so that they make a significant contribution to the diffraction pattern), such that there should not be too many of them (so that their positions can be located); and they should not change the structure of the molecule or of the crystal cell, i.e., the crystals should be isomorphous. Isomorphous replacement is usually done by diffusing different heavy-metal complexes into the channels of the preformed protein crystals. The protein molecules expose side chains (such as SH groups) into these solvent channels that are able to bind heavy metals. It is also possible to replace endogenous light metals in metalloproteins with heavier ones, e.g., zinc by mercury, or calcium by samarium. Alternatively, the isomorphous derivative can be obtained by covalently attaching a heavy metal to the macromolecular in solution and then to subject it to crystallization conditions.

Heavy metal atoms routinely used for isomorphous replacement include but are not limited to mercury, uranium, platinum, gold, lead, and selenium. Specific examples include mercury chloride, ethyl-mercury phosphate, and osmium pentamine, iridium pentamine.

Since such heavy metals contain many more electrons than the light atoms (H, N, C, O, and S) of the protein, they scatter x-rays more strongly. All diffracted beams would therefore increase in intensity after heavy-metal substitution if all interference were positive. In fact, however, some interference is negative; consequently, following heavy-metal substitution, some spots measurably increase in intensity, others decrease, and many show no detectable difference.

Phase differences between diffracted spots can be determined from intensity changes following heavy-metal substitution. First, the intensity differences are used to deduce the positions of the heavy atoms in the crystal unit cell. Fourier summations of these intensity differences give maps of the vectors between the heavy atoms, the so-called Patterson maps. From these vector maps the atomic arrangement of the heavy atoms is deduced. From the positions of the heavy metals in the unit cell, one can calculate the amplitudes and phases of their contribution to the diffracted beams of protein crystals containing heavy metals.

This knowledge is then used to find the phase of the contribution from the protein in the absence of the heavy-metal atoms. As both the phase and amplitude of the heavy metals and the amplitude of the protein alone is known, as well as the amplitude of the protein plus heavy metals (i.e., protein heavy-metal complex), one phase and three amplitudes are known. From this, the interference of the X-rays scattered by the heavy metals and protein can be calculated to see if it is constructive or destructive. The extent of positive or negative interference, with knowledge of the phase of the heavy metal, given an estimate of the phase of the protein. Because two different phase angles are determined and are equally good solutions, a second heavy-metal complex can be used which also gives two possible phase angles. Only one of these will have the same value as one of the two previous phase angles; it therefore represents the correct phase angle. In practice, more than two different heavy-metal complexes are usually made in order to give a reasonably good phase determination for all reflections. Each individual phase estimate contains experimental errors arising from errors in the measured amplitudes. Furthermore, for many reflections, the intensity differences are too small to measure after one particular isomorphous replacement, and others can be tried.

The amplitudes and the phases of the diffraction data from the protein crystals are used to calculate an electron-density map of the repeating unit of the crystal. This map then has to be interpreted as a polypeptide chain with a particular amino acid sequence. The interpretation of the electron-density map is made more complex by several limitations of the data. First of all, the map itself contains errors, mainly due to errors in the phase angles. In addition, the quality of the map depends on the resolution of the diffraction data, which in turn depends on how well-ordered the crystals are. This directly influences the image that can be produced. The resolution is measured in Å units; the smaller this number is, the higher the resolution and therefore the greater the amount of detail that can be seen.

Building the initial model is a trial-and-error process. First, one has to decide how the polypeptide chain weaves its way through the electron-density map. The resulting chain trace constitutes a hypothesis, by which one tries to match the density of the side chains to the known sequence of the polypeptide. When a reasonable chain trace has finally been obtained, an initial model is built to give the best fit of the atoms to the electron density. Computer graphics are used both for chain tracing and for model building to present the data and manipulated the models.

The initial model will contain some errors. Provided the protein crystals diffract to high enough resolution (e.g., better than 3.5 Å), most or substantially all of the errors can be removed by crystallographic refinement of the model using computer algorithms. In this process, the model is changed to minimize the difference between the experimentally observed diffraction amplitudes and those calculated for a hypothetical crystal containing the model (instead of the real molecule). This difference is expressed as an R factor (residual disagreement) which is 0.0 for exact agreement and about 0.59 for total disagreement.

In general, the R factor is preferably between 0.15 and 0.35 (such as less than about 0.24-0.28) for a well-determined protein structure. The residual difference is a consequence of errors and imperfections in the data. These derive from various sources, including slight variations in the conformation of the protein molecules, as well as inaccurate corrections both for the presence of solvent and for differences in the orientation of the microcrystals from which the crystal is built. This means that the final model represents an average of molecules that are slightly different both in conformation and orientation.

In refined structures at high resolution, there are usually no major errors in the orientation of individual residues, and the estimated errors in atomic positions are usually around 0.1-0.2 Å, provided the amino acid sequence is known. Hydrogen bonds, both within the protein and to bound ligands, can be identified with a high degree of confidence.

Most x-ray structures are determined to a resolution between 1.7 Å and 3.5 Å. Electron-density maps with this resolution range are preferably interpreted by fitting the known amino acid sequences into regions of electron density in which individual atoms are not resolved.

In summary, determining the structure of a macromolecule employs, but are not limited to the following steps (Cantor, C. R. and Schimmel, P. R., *Biophysical Chemistry*, Part II, Chapter 13, pages 763-764, 1980, Freeman and Company, San Francisco):

1. Prepare crystals of the native macromolecules. Using the crystals, determine the space group and unit-cell dimensions, and collect a set of scattering amplitude data.

2. Prepare heavy-atom isomorphous derivatives. For each derivative, collect a new set of scattering amplitude data.

3. Find the locations of the heavy atoms in the crystal. A routinely practiced method is the difference isomorphous Patterson synthesis.

4. Refine the positions assigned to heavy atoms using difference Fourier refinement techniques or other methods that are known to crystallographers.

5. Estimate the phases of the parent crystal(s) by comparing the structure factor data of the parent crystal with the corresponding data of one or more heavy-atom isomorphous derivatives. Generally, the more heavy-atom derivatives available, the more accurate the phase estimates will be.

6. Refine the positions of the heavy atoms further using least-square, difference Fourier techniques, or other methods known in the art.

7. Calculate an electron density map using the estimated phase and observed amplitude information.

8. Build a model based on the electron density map. Repeating steps 4-8 with data at higher resolution to construct a molecular model.

One can also attempt to refine the structure by calculating phases from the atom positions in the molecular model and use them in stead of the phases determined in steps 5 and 6. The refinement can involve Fourier transform or least-squares techniques, and can treat just the x-ray data or can also include information about known energetics of protein conformation.

SUMMARY OF THE INVENTION

The present invention is based on the determination of the atomic structure of ribosomes and ribosomal subunits. In particular, the present invention is based on the determination of the atomic structure of the large ribosomal subunits. More particularly, the present invention is based on the determination of the atomic structure of the 50S ribosomal subunits. Even more particularly, the present invention is based on the determination of the atomic structure of the 50S ribosomal subunit of archaebacteria. Most particularly, the present invention is based on the determination of the atomic structure of the 50S ribosomal subunit of *Haloarcula marismortui*.

The present invention provides crystals of ribosomes or ribosomal subunits wherein the crystals have an average thickness greater than about 15 μm.

The present invention also provides crystals of ribosomes or ribosomal subunits wherein the average thickness of the crystals is from about 16 μm to about 65 μm, or from about 66 μm to about 105 μm, or from about 104 μm to about 155 μm, or from about 156 μm to about 205 μm. In particular, the present invention provides such crystals wherein the average thickness is from about 100 μm to about 200 μm.

The present invention also provides untwinned crystals of ribosomes or ribosomal subunits.

The present invention provides crystals which have an average thickness greater than about 15 μm and/or are untwinned wherein the crystals are for either large ribosomal subunits or small ribosomal subunits. More particularly, the present invention provides such crystals wherein the large ribosomal subunit is a 50S or 60S ribosomal subunit.

The crystals of the present invention may be obtained using the ribosomes or ribosomal subunits from prokaryotes or from eukaryotes. In particular, the crystals of the present invention are obtained for ribosomes or ribosomal subunits obtained from bacteria or archaebacteria. Even more particularly, the crystals of the present invention are obtained for the ribosomes or ribosomal subunits of *Haloarcula marismortui*. However, the crystals of the present invention may be obtained using the ribosomes or ribosomal subunits from any organism, particularly from animals, more particularly from mammals, and even more particularly from humans.

The present invention provides crystals wherein the crystals effectively diffract X-rays for the determination of atomic coordinates to a resolution of at least about 3.0 Å. More particularly, the crystals of the present invention effectively diffract X-rays for determination of atomic coordinates to a resolution of about 2.4 Å.

The crystals of the present invention may also include a ligand, wherein the ligand is in crystal or non-crystal form.

The crystals of the present invention are of sufficient quality for the determination of the atomic coordinates of ribosomes or ribosomal subunits.

In particular, the present invention provides crystals of 50S ribosomal subunits whose atomic structure is characterized by the coordinates deposited at the Protein Data Bank ID: 1FFK. The present invention further provides the phases computed from the coordinates of the deposited coordinates and the uses of such phase information.

The present invention also provides methods of obtaining an electron density map of a selected ribosomal subunit, wherein the selected ribosomal subunit is only slightly different from the ribosomal subunit used to obtain the computed phases of the crystals provided herein, the method comprising: (a) producing a crystal of a selected ribosomal subunit, wherein the crystal is isomorphous; (b) obtaining diffraction amplitudes of the crystal produced in step (a); (c) combining the computed phases of the deposited coordinates with the diffraction amplitudes obtained in step (b) to produce a combined data set; and, (d) obtaining an electron density map of the selected ribosomal subunit based on the combined data set obtained in step (c).

The present invention further provides methods of obtaining an electron density map of a selected ribosomal subunit, wherein the selected ribosomal subunit is closely related to the ribosomal subunit used to obtain the computed phases, said method comprising: (a) producing a crystal of a selected ribosomal subunit, wherein the crystal crystallizes in a different unit cell with different symmetry than the crystal which was used to compute the phases; (b) obtaining atomic coordinates for the crystal produced in step (a); (c) obtaining phases of the selected ribosomal subunit by using the atomic coordinates obtained in step (b) and the computed phases in a molecular replacement technique; and (d) obtaining an electron density map of the selected ribosomal subunit from the phases obtained in step (c).

Alternatively, the present invention provides a method of obtaining a model of a selected ribosomal subunit, wherein the selected ribosomal subunit diverges significantly from but is still homologous to the ribosomal subunit used to obtain the computed phases, said method comprising: (a) producing a crystal of a selected ribosomal subunit; (b) obtaining atomic coordinates for the crystal produced in step (a);(c) obtaining a model for the selected ribosomal subunit by homology modeling using the atomic coordinates obtained in step (b) and the computed phases.

The present invention provides a method of growing a crystal of a ribosome or a ribosomal subunit comprising: (a) isolating a ribosome or a ribosomal subunit; (b) precipitating the ribosome or ribosomal subunit; (c) back-extracting the precipitated ribosome or ribosomal subunit to obtain a solution; (d) seeding the back-extracted solution; (e) growing a crystal of the ribosome or ribosomal subunit from the seeded solution by vapor diffusion at room temperature; and (f) harvesting the crystal. Alternatively, the method further comprises: (g) stabilizing the crystal by gradual transfer into a solution containing high salt concentration; (h) maintaining the crystal under high salt concentration; and (i) flash freezing the crystal. Preferably, the high salt concentration is from about 1.2 M salt to about 1.7 M salt.

The present invention contemplates a crystal produced by the method of growing the crystal comprising the steps as stated above.

The present invention discloses a method of obtaining X-ray diffraction data for a crystal of a ribosome or a ribosomal subunit comprising: (a) obtaining a crystal of a ribosome or a ribosomal subunit, wherein the crystal has one or more of the following characteristics: (1) an average thickness of greater than 15 μm; (2) untwinned; and (b) using X-ray crystallography to obtain X-ray diffraction data for the crystal of the ribosome or ribosomal subunit. The present invention also discloses a method of obtaining an electron density map of a ribosome or a ribosomal subunit comprising using the X-ray diffraction data obtained by the disclosed method to obtain an electron density map of the ribosome or ribosomal subunit.

In one aspect, the present invention provides a method of obtaining X-ray diffraction data for a complex of a ribosome and a ligand or a complex of a ribosomal subunit and a ligand comprising: (a) obtaining a crystal of a ribosome or a ribosomal subunit, wherein the crystal has one or more of the following characteristics: (1) an average thickness of greater than 15 μm; (2) untwinned; (b) diffusing a ligand through the crystal and permitting the ligand to attach to the crystal so as to form a complex; and (c) using X-ray crystallography to obtain X-ray diffraction data for the complex.

In an alternative aspect, the present invention provides a method of obtaining X-ray diffraction data for a complex of a ribosome and a ligand or for a ribosomal subunit and a ligand comprising: (a) obtaining a co-crystal for a complex of a ribosome and a ligand or for a complex of a ribosomal subunit and a ligand, wherein the co-crystal has one or more of the following characteristics: (1) an average thickness of greater than 15 μm; (2) untwinned; and (b) using X-ray crystallography to obtain X-ray diffraction data for the complex. Preferably, the present invention provides a method of obtaining an electron density map for a complex of a ribosome and a ligand or for a complex of a ribosomal subunit and a ligand comprising using the X-ray diffraction data obtained by the provided method to obtain an electron density map of the complex of the ribosome and the ligand or for the complex of the ribosomal subunit and the ligand.

In one embodiment, the present invention discloses a method of locating the attachment of a ligand to a ribosome or the attachment of a ligand to a ribosomal subunit comprising: (a) obtaining X-ray diffraction data for a ribosome or for a ribosomal subunit; (b) obtaining X-ray diffraction data for a complex of a ribosome and a ligand or for a complex of a ribosomal subunit and a ligand; (c) subtracting the X-ray diffraction data obtained in step (a) from the X-ray diffraction data obtained in step (b) to obtain the difference in the X-ray diffraction data; (d) obtaining phases that correspond to X-ray diffraction data obtained in step (a) using one or more of the techniques selected from the group consisting of MIR, MIRAS and SAD; (e) utilizing the phases obtained in step (d) and the difference in the X-ray diffraction data obtained in step (c) to compute a difference Fourier image of the ligand; and (f) locating the attachment of the ligand to a ribosome or the attachment of the ligand to a ribosomal subunit based on the computations obtained in step (e).

Alternatively, the present invention discloses a method of obtaining a map of a ligand attached to a ribosome or of a ligand attached to a ribosomal subunit comprising: (a) obtaining X-ray diffraction data for a ribosome or for a ribosomal subunit; b) obtaining X-ray diffraction data for a complex of a ribosome and a ligand or a complex of a ribosomal subunit and a ligand; (c) obtaining phases that correspond to X-ray diffraction data obtained in step (a) using one or more of the techniques selected from the group consisting of MIR, MIRAS and SAD; and (e) utilizing the phases obtained in step (c) and the X-ray diffraction data obtained in step (b) to compute a map of the ligand and the ribosome or of the ligand and the ribosomal subunit.

In one embodiment, the present invention provides a method of obtaining a modified agent comprising: (a) obtaining a crystal of a ribosome or of a ribosomal subunit; (b) obtaining the atomic coordinates of the crystal; (c) using the atomic coordinates and one or more molecular modeling techniques to determine how to modify the interaction of an agent with a ribosome or ribosomal subunit; and (d) modifying the agent based on the determinations obtained in step (c) to produce a modified agent. Alternatively, the method further comprises contacting the modified agent with a ribosome or ribosomal subunit and detecting the interaction of the agent to the ribosome or ribosomal subunit. In a preferred embodiment, the one or more molecular modeling techniques are selected from the group consisting of graphic molecular modeling and computational chemistry. The present invention also contemplates a modified agent produced by the method, wherein the modified agent binds differently to a ribosome or ribosomal subunit than does the agent from which the modified agent was derived. In a preferred embodiment, the modified agent is a therapeutic agent.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1A-E. Electron Density from the 2.4 Å Resolution Electron Density Map.

(A) stereo view of a junction between 23S rRNA domains II, III, and IV.

(B) The extended region of L2 interacting with surrounding RNA.

(C) Detail in the L2 region showing a bound $Mg^{2+}$ ion.

(D) Detail from L2 showing amino acid side chains.

(E) helices 94-97 from domain 6.

Figure 2:
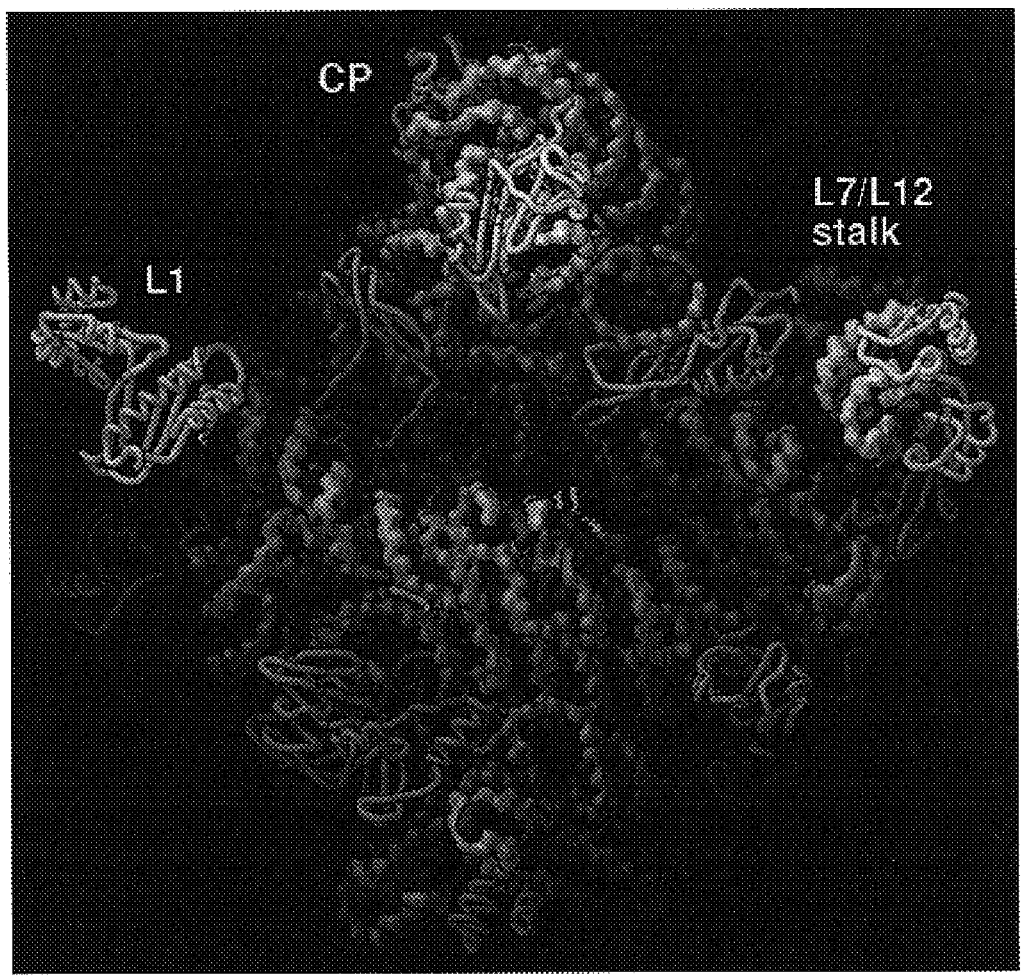

FIG. 2. The *H. Marismortui* Large Ribosomal Subunit in the Crown View.

The subunit is shown in the crown view, with its L7/L12 stalk to the right, its L1 stalk to the left, and its central protuberance (CP) up. In this view, the surface of the subunit that interacts with the small subunit faces the reader. RNA is shown in gray in a space-filling rendering. The backbones of the proteins visible are rendered in gold. A transition state analogue bound to the peptidyl transferase site of the subunit is indicated in green (Nissen et al., 2000). The particle is approximately 250 Å across.

Figure 3A:
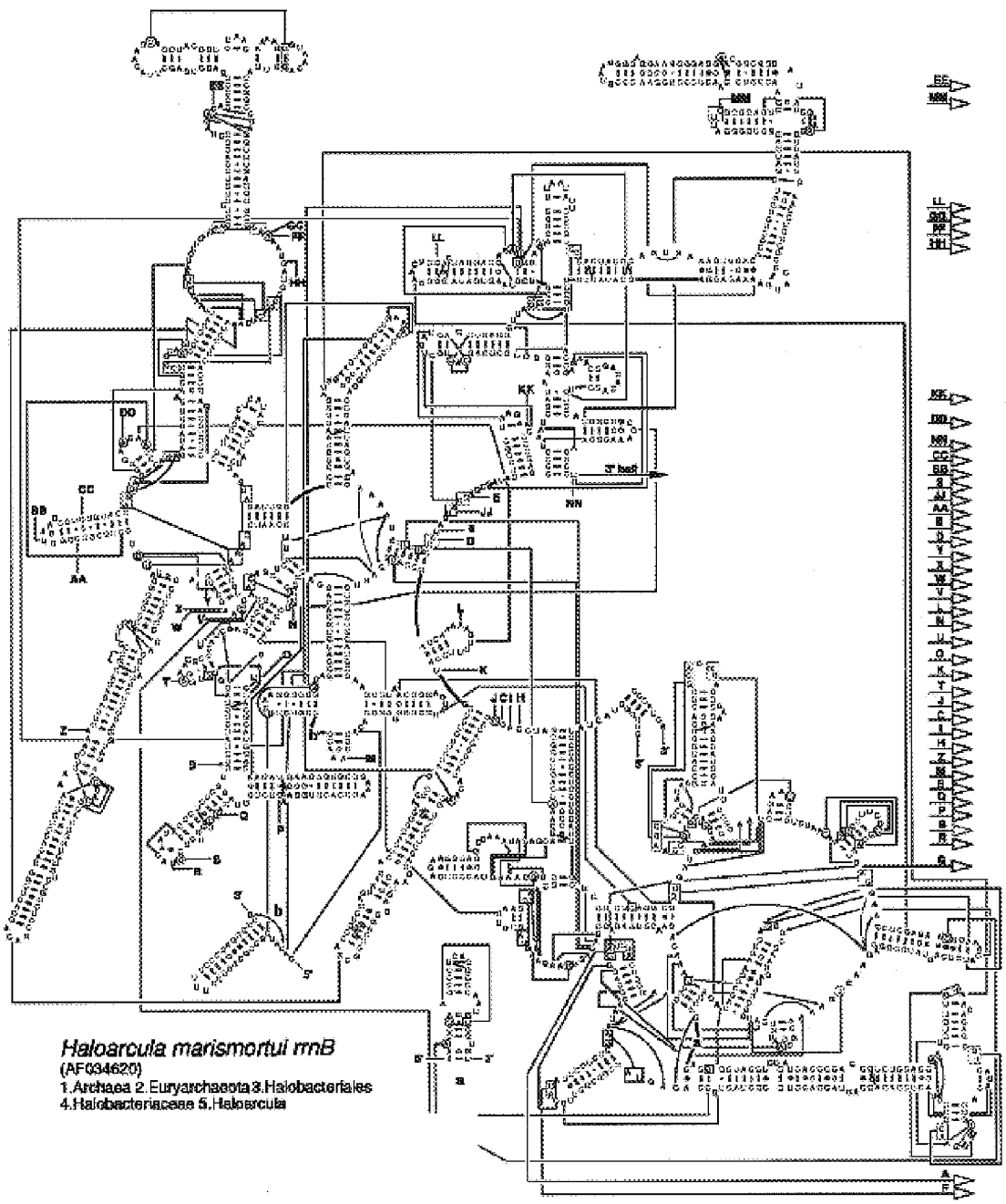
Figure 3B:
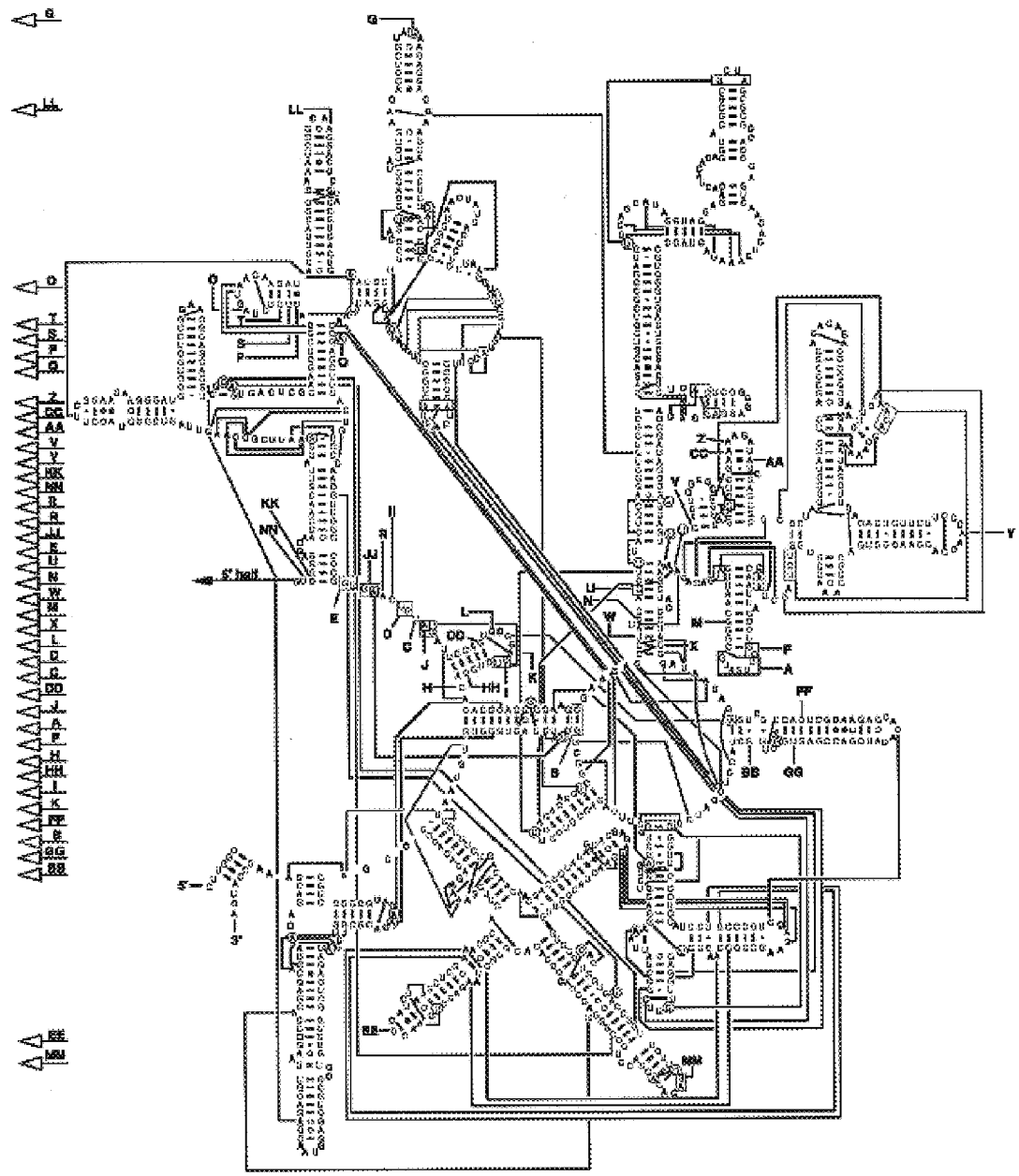

FIGS. 3A-B. The Secondary Structure of the 23S rRNA from *H. Marismortui*.

The secondary structure of this 23S rRNA is shown in format made standard by Robin Gutell and his colleagues (Gutell et al., 2000). This diagram shows all the base pairings seen in the crystal structure of the large subunit that are stabilized by at least 2 hydrogen bonds. Pairings shown in red were predicted and are observed. Those shown in green were predicted, but are not observed. Interactions shown in blue are observed, but were not predicted. Bases shown in black are not involved in pairing interactions. Sequences that cannot be visualized in the 2.4 Å resolution electron density map are depicted in gray with the secondary structures predicted for them. This figure is available on the web site, www.rna.icmb.utexas.edu/.

FIGS. 4A-L. The Tertiary Structures of the RNA Domains in the *H. Marismortui* Large Ribosomal Subunit, its RNA as a Whole, and Schematics of its RNAs.

(A and B) The RNA structure of the entire subunit. Domains are color coded as shown in the schematic (FIG. 5C). (A) the particle in the crown view.

(B) the image in (a) rotated 180° about an axis running vertically in the plane of the image.

(C and D). Schematic diagram of 23S rRNA and the secondary structure of 5S rRNA. (C) schematic of 23S rRNA secondary structure (FIG. 3) with helices numbered according to Leffers et al. (1987), and the domains of the molecule are indicated by color shading. (D) the secondary structure of 5S rRNA from *H. marismortui*. Thick lines joining bases represent Watson-Crick pairing. Bases joined by a lower case "o" indicate non-Watson-Crick pairing. Bases joined by thin lines interact via a single hydrogen bond. Bases shown in black don't pair. Base shown in red are phylogenetically predicted pairing that are now confirmed (Symanski et al., 1998). Pairs shown in blue are observed, but were not predicted, and pairs shown in green were predicted but are not observed.

(E through L) Stereo views of the RNA domains in the 23S rRNA and of 5S rRNA. Each domain is color-coded from its 5' end to its 3' end to help the viewer follow its trajectory in three dimensions. The surfaces where the most important inter-domain interactions occur are shown in mono. (E) domain I. (F) domain II. (G) domain III. (H) domain IV. (I) domain 5, crown view. (J) domain 5, back view. (K) domain VI. (L) 5S rRNA.

Figure 5A:
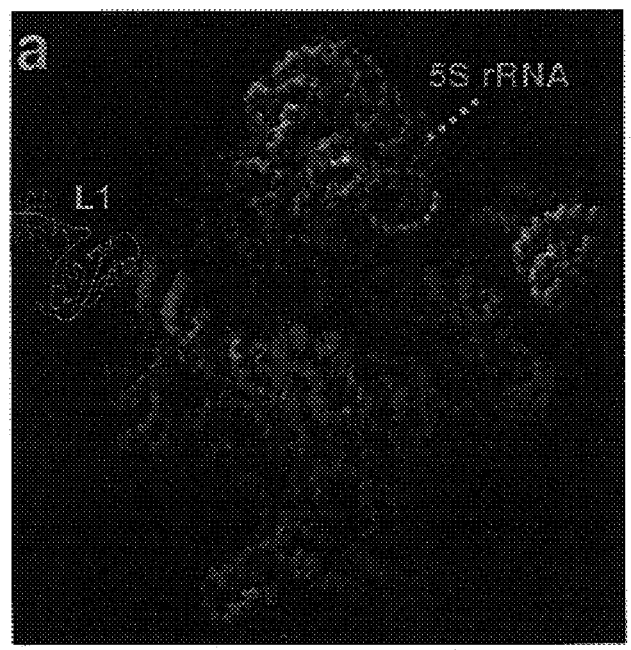
Figure 5B:
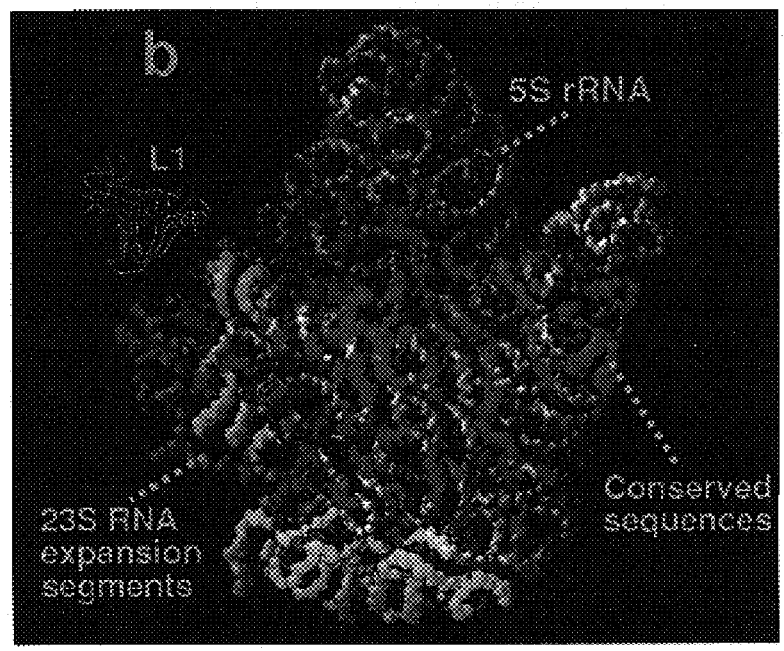
Figure 5C:
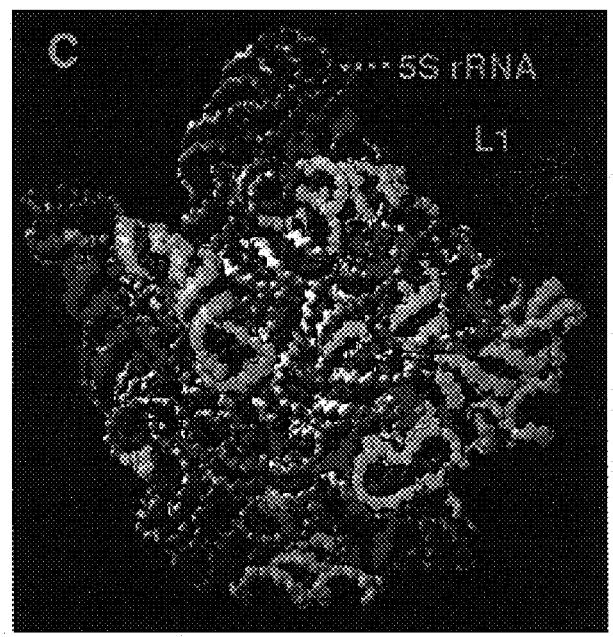

FIGS. 5(A-C). Conservations and Expansions in the 23S rRNA of *H. Marismortui*.

The generality of the RNA in these images is gray. Sequences that are found to be >95% conserved across the three phylogenetic kingdoms are shown in red. Sequences where expansion in the basic 23S structure is permitted are shown in green (Gutell et al., 2000). (A) the particle rotated with respect to the crown view so that its active site cleft can be seen. (B) the crown view. (C) the back view of the particle, i.e., the worn view rotated 180° about its vertical axis.

Figure 6:
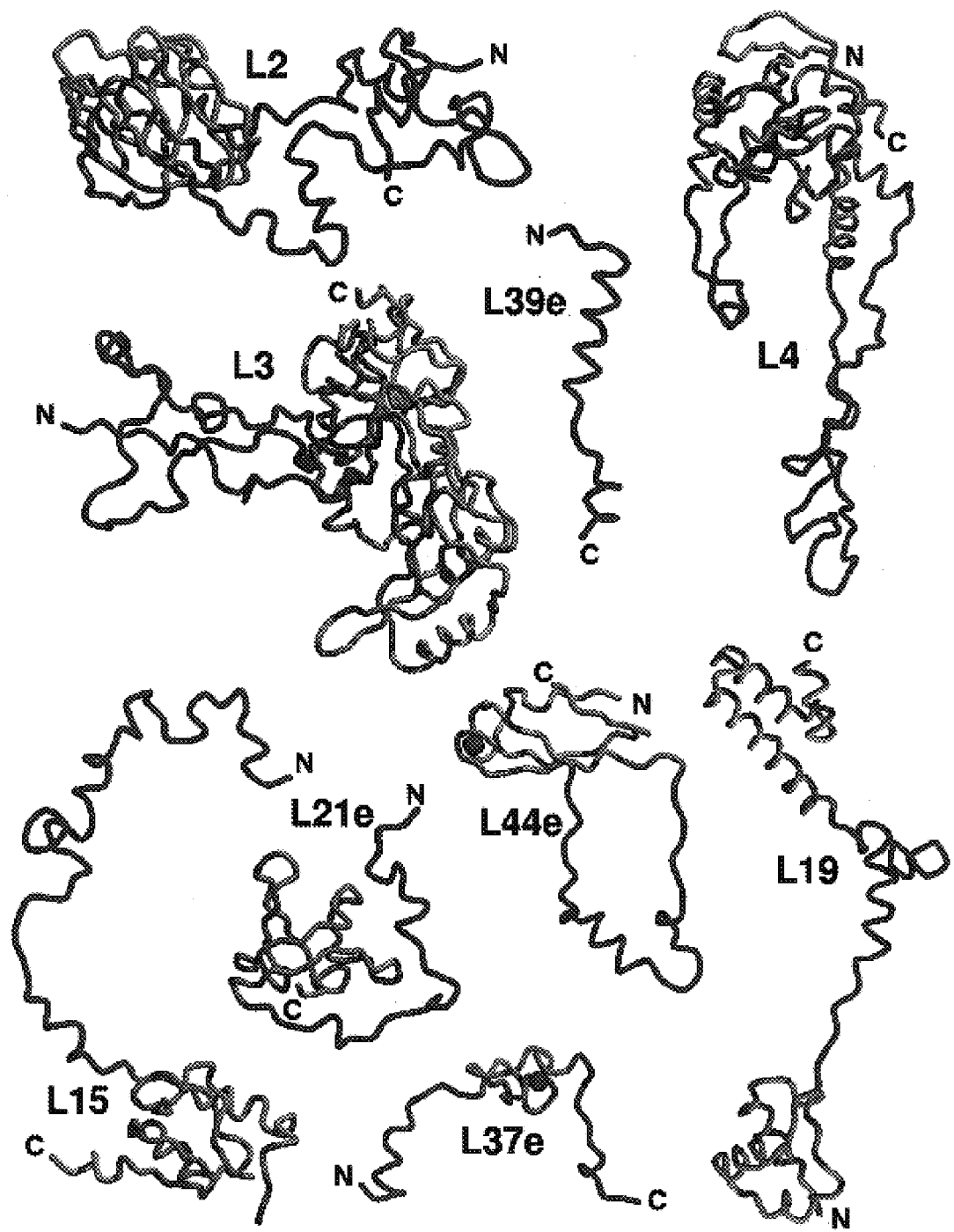

FIG. 6. Structures of Some Large Subunit Ribosomal Proteins that have Non-Globular Extensions.

Only the backbones of the proteins are shown. The globular domains of these proteins are shown in green, and their non-globular extensions are depicted in red. The positions of the zinc ions in L44e and L37e are also indicated.

Figure 7A:
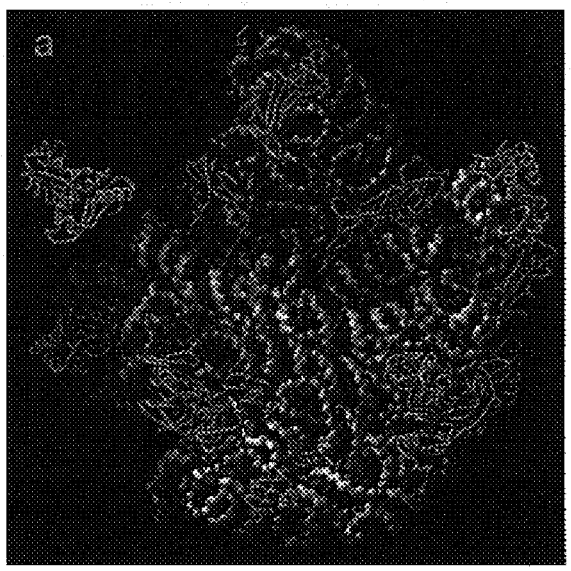
Figure 7B:
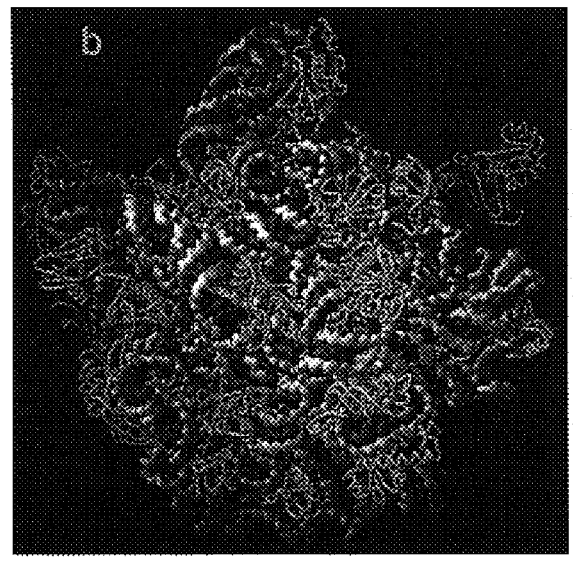
Figure 7C:
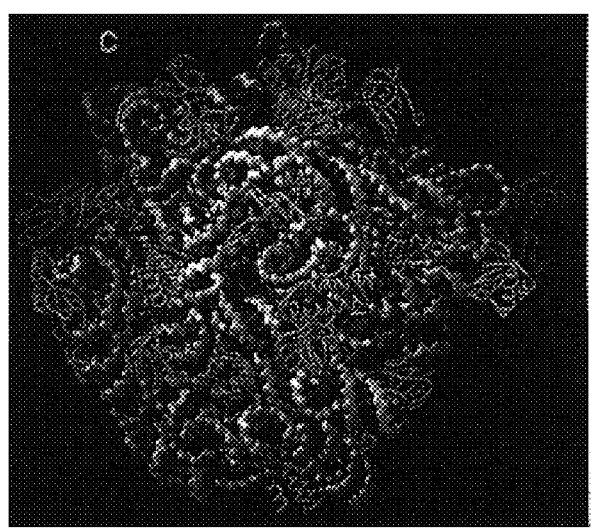

FIGS. 7A-C. Proteins that Appear on the Surface of the Large Ribosomal Subunit.

The RNA of the subunit is shown in gray, as in FIG. 2, and protein backbones are shown in gold. (A) the subunit in the crown view of the subunit. (B) back side of the subunit in the crown view orientation. (C) bottom view; the end of the peptide tunnel is obvious in the center of this image. The proteins visible in each image are identified in the small images at the lower left of the figure.

FIGS. 8A-E. The Protein Distribution and Protein-RNA Interactions in the Large Ribosomal Subunit.

(A) The structures of proteins in the neighborhood of the end of the peptide tunnel and how they relate to the RNA sequences with which they interact. Protein L22 extends a long β hairpin extension inside the 23S rRNA. L24 has a similar extension but the entire protein is on the surface of the particle. L39 is the only protein in the subunit that lacks tertiary structure, while L37e has both—and C-terminal extensions. L19 is unique in having two globular domains on the surface of the subunit connected by an extended sequence that weaves through the RNA. The end of L39 (green) actually enters the tunnel, while L37e (red) is entirely surrounded by RNA.

(B) The non-globular extensions of L2 and L3 reaching through the mass of 23S rRNA towards the peptidyl transferase site, which is marked by a CCdAp-puromycin molecule.

(C) L22 interacting with portions of all 6 of the domains of 23S rRNA.

(D) Schematic of 23S rRNA showing the locations of the sequences that make at least van der Waals contact with protein (red).

(E) Stereo view of the proteins of the large ribosomal subunit with all the RNA stripped away. Proteins are colored as an aid to visualization only.

Figure 9C:
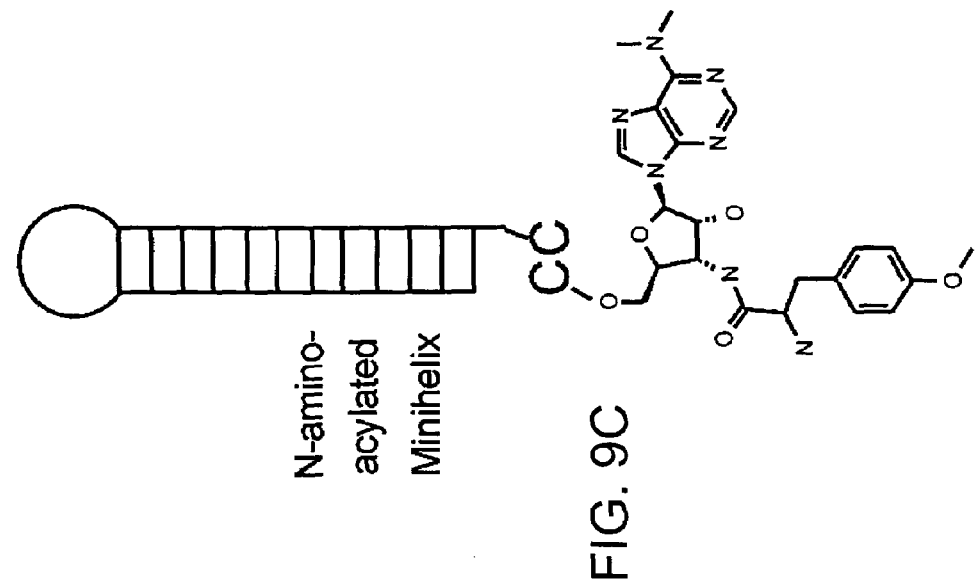
Figure 9A:
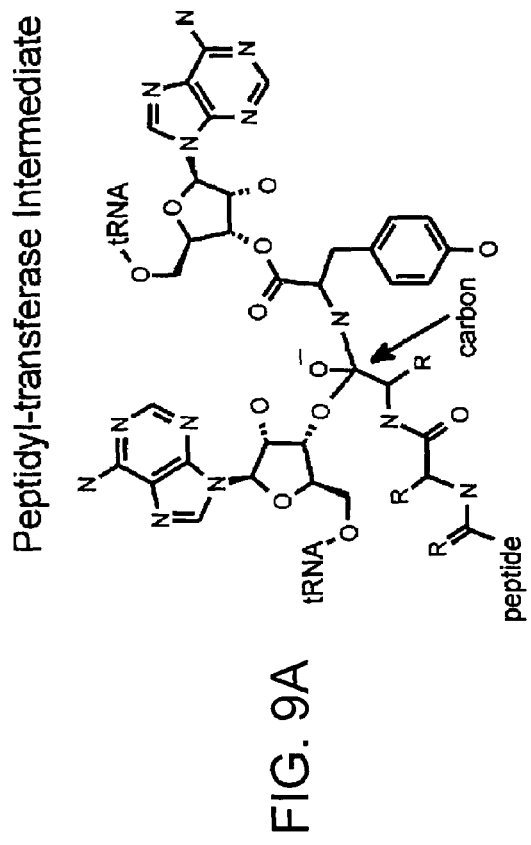
Figure 9B:
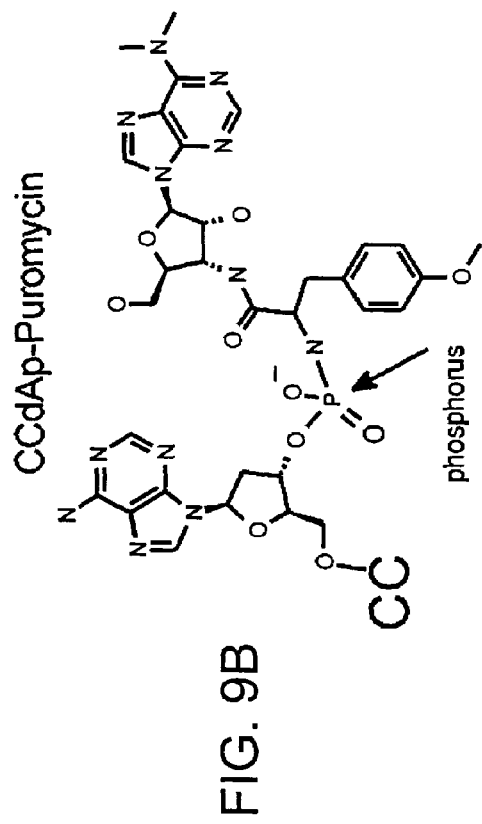

FIGS. 9A-C. Chemical Structures of Ribosome Peptidyl Transferase Substrates and Analogues.

(A) The tetrahedral carbon intermediate produced during peptide bond formation; the tetrahedral carbon is indicated by an arrow.

(B) The transition state analogue formed by coupling the 3' OH of CCdA to the amino group of the O-methyl tyrosine residue of puromycin via a phosphate group, CCdA-p-Puro (a gift of Michael Yarus) (Welch et al., 1995).

(C) An amino-N-acylated mini helix constructed to target the A-site. The oligonucleotide sequence 5' phosphate CCG-GCGGGCUGGUUCAAACCGGCCCGCCGGACC 3' (SEQ ID NO: 1) puromycin should form 12 base pairs. The construct was based on a mini helix which is a suitable substrate for amino-acylation by Tyr-tRNA synthetase. The 3' OH of its terminal C is coupled to the 5' OH of the N6-dimethyl A moiety of puromycin by a phosphodiester bond.

Figure 10A:
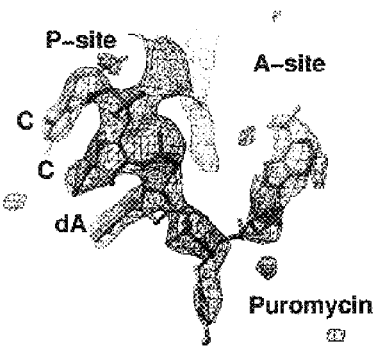
Figure 10B:
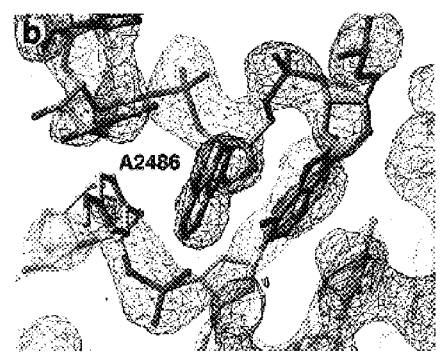
Figure 10C:
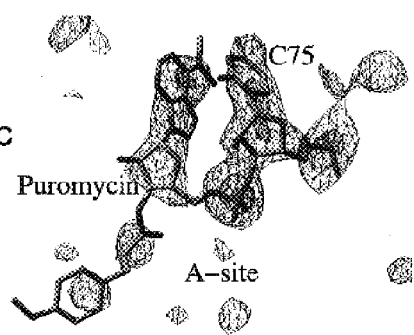

FIGS. 10A-C. Experimentally Phased Electron Density Maps of the Substrate Analogue Complexes at 3.2 Å Resolution, with Models Superimposed (oxygen, red; phosphorus, purple; nitrogen, blue and carbon, green for rRNA and yellow for substrate).

(A) An Fo (complex)-Fo(parent) difference electron density map with a skeletal model of CCdA-p-Puro superimposed.

(B) A 2Fo(complex)-Fo(parent) electron density map of the CCdA-p-Puro in the active site region with the structures of the ribosome and inhibitor superimposed showing the proximity of the N3 of A2486 (2451) to the phosphate, non-bridging oxygen in this complex.

(C) An Fo(complex)-Fo(parent) differences electron density map of the tRNA acceptor stem analogue with a skeletal model of CCpuro superimposed. There is density only for the ribose and phosphate of C74 and none for the rest of the RNA hairpin.

Figure 11A:
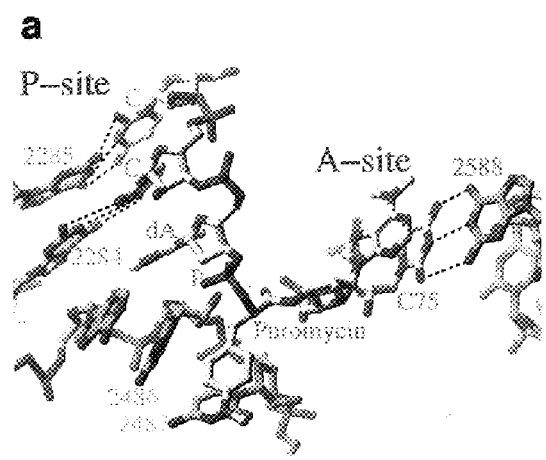
Figure 11B:
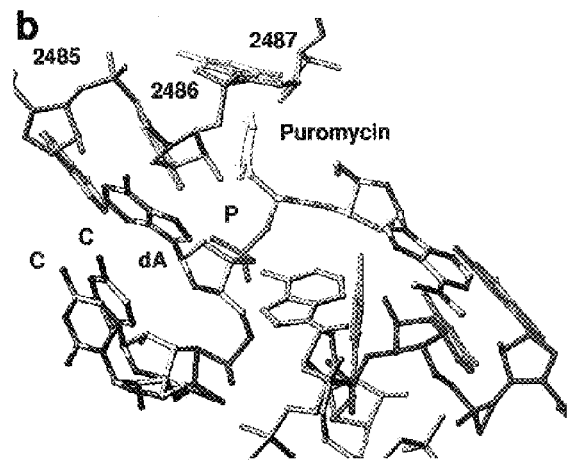

FIGS. 11A-B. A Combined Model of the CCA Portion of the Mini Helix Bound to the A-site and CCdA-p-Puro Bound to the A- and P-Sites Color Coded as in 2.

(A) The base-pairing interactions between the P-site C74 and C75 and the P loop of 23S rRNA on the left and the A-site C75 with the A loop of 23S rRNA on the right. The catalytic A2486 is near the phosphate oxygen (P) that is the analogue of the tetrahedral intermediate oxyanion.

(B) A view showing A2637 (in all blue) lying between the two CCA's and A2486 (green) whose N3 approaches a non-bridging phosphate oxygen. The N1 atoms of the A76 bases from the A- and P-site tRNAs are making nearly identical interactions with a ribose 2' OH in both the A- and P-loops, respectively, and an approximate 2-fold axis relates these residues.

Figure 12:
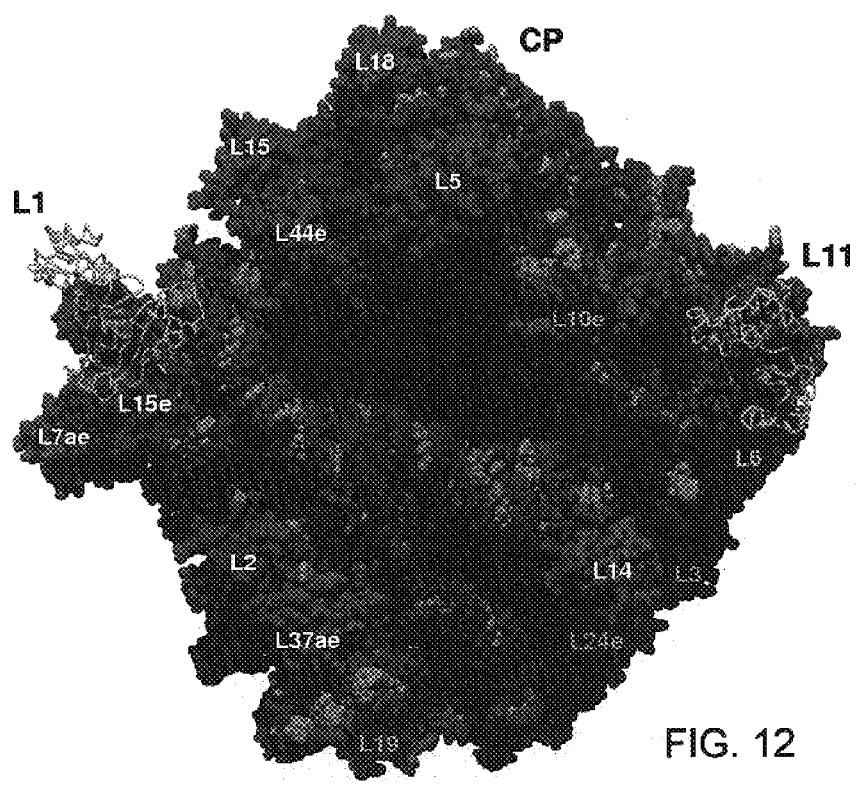

FIG. 12. A Space Filling Model of the 23S and 5S rRNA, the Proteins and the CCdA-p-Puro Inhibitor Viewed Down the Active Site Cleft in a Rotated "Crown View".

The bases are white and the sugar phosphate backbones are yellow. The inhibitor is red and the numbered proteins are blue. The L1 and L11 proteins positioned at lower resolution are in blue backbone. The central protuberance is labeled CP.

Figure 13A:
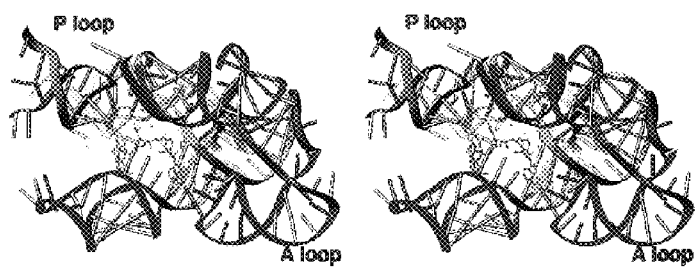
Figure 13B:
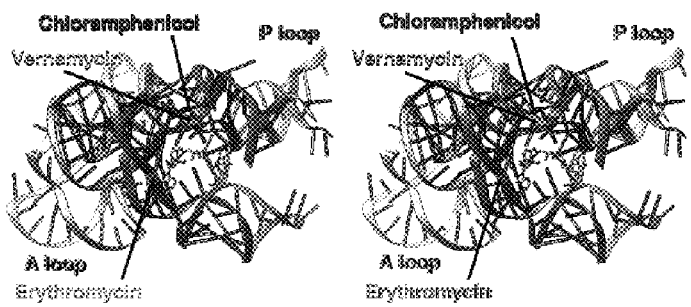
Figure 13C:
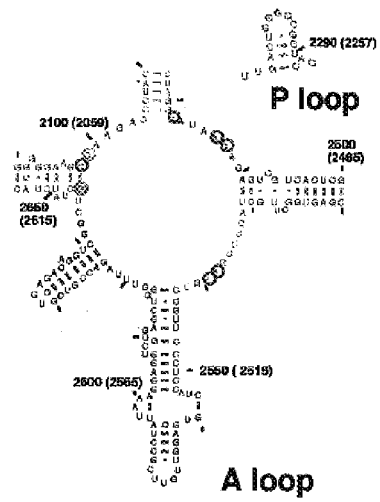

FIGS. 13A-C. Domain V Active Site with its Central Loop Shown as the Secondary Structure.

(A) Diagram showing the three dimensional distribution of the residues comprising the loops A and P and the peptidyl transferase loop.

(B) Stereo view of the central loop in domain V from the direction of the tunnel. The residues are color coded based on mutations which confer antibiotic resistance.

Figure 14A:
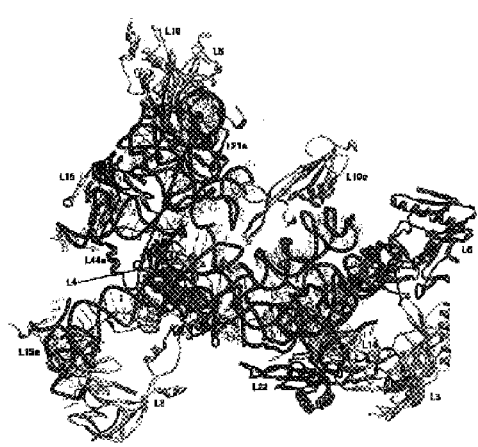
Figure 14B:
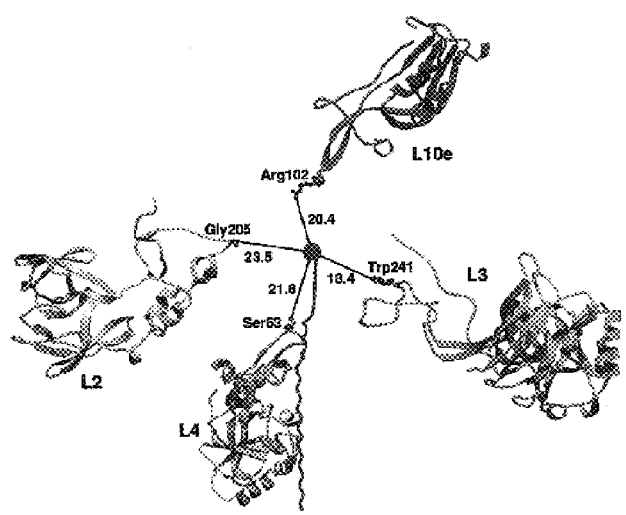

FIGS. 14A-B. The Closest Approach of Polypeptides to the Peptidyl Transferase Active Site Marked by a Ball and Stick Representation of the Yarus Inhibitor, CCdA-p-Puro.

(A) A coil representation of domain V RNA backbone in red and bases in gray and a ribbon backbone representation of all 13 proteins that interact with it.

(B) A closeup view of the active site with the RNA removed. The phosphate of the Yarus analogue and the proteins whose extensions are closest to the inhibitor are shown in ribbon with their closest side-chains in all atom representation. The distances between the closest protein atoms and the phosphorous analogue of the tetrahedral carbon (pink) are shown, as is a modeled peptide (pink).

Figure 15:
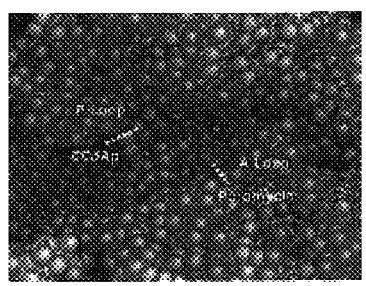

FIG. 15. Conserved Nucleotides in the Peptidyl Transferase Region that Binds CCdA-p-Puro.

A space filling representation of the active site region with the Yarus inhibitor viewed down the active site cleft. All atoms belonging to 23S rRNA nucleotides that are 95% conserved in all three kingdoms (Gutell et al., 2000) are colored red and all other nucleotides are white; the inhibitor is colored blue.

Figure 16A:
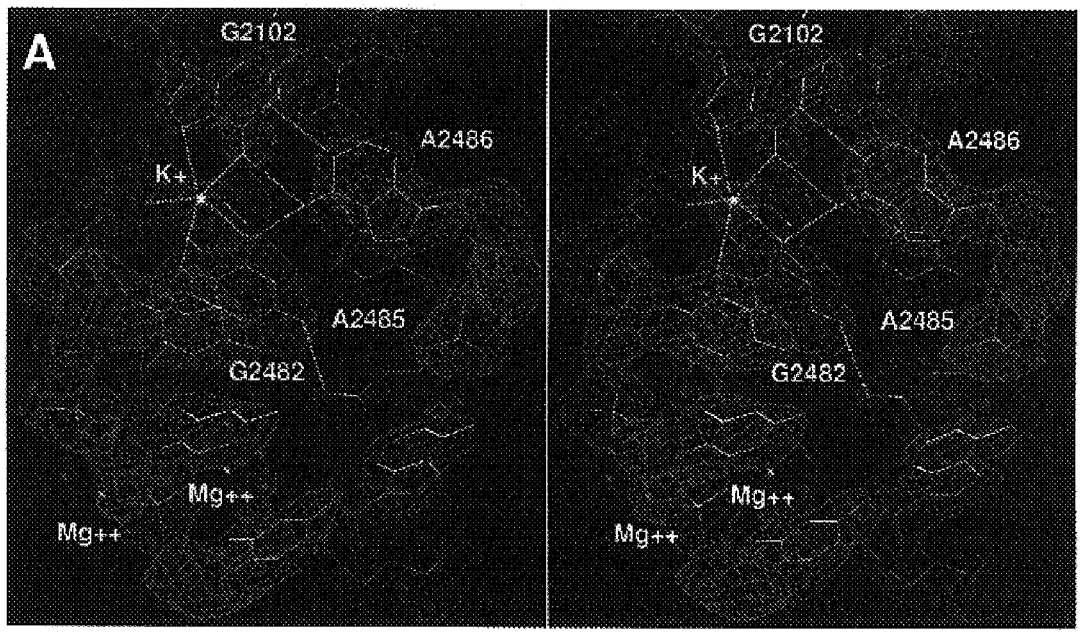
Figure 16B:
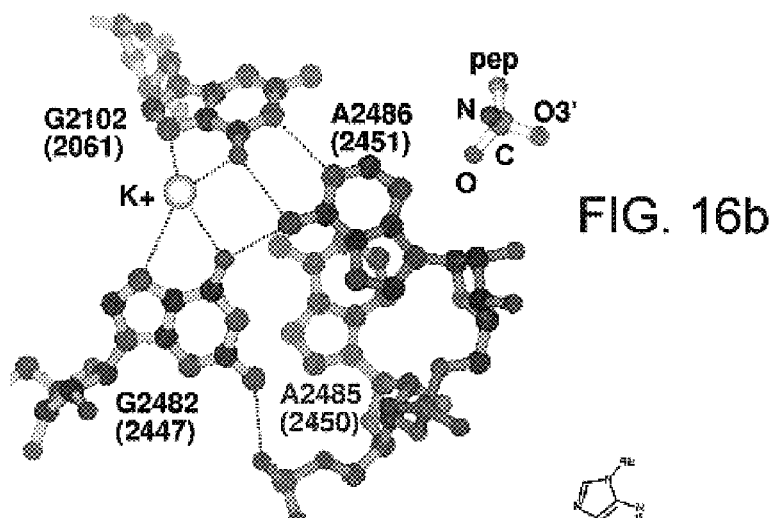
Figure 16C:
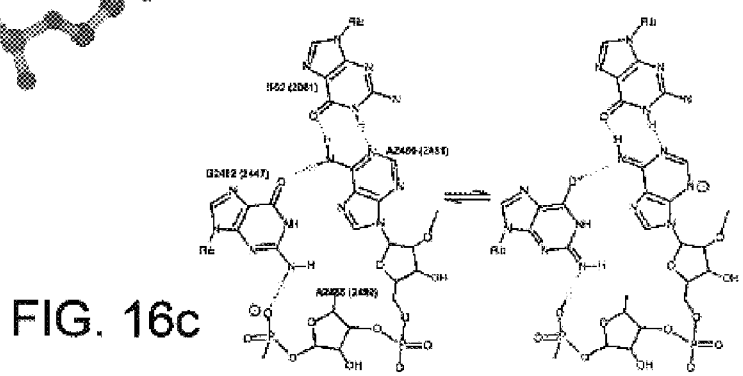

FIGS. 16A-C. The Catalytic Apparatus of the Peptidyl Transferase Active Site.

(A) A portion of the experimental 2.4 Å resolution electron density map (Ban et al, 2000) of the large subunit in the region of the catalytic site in stereo. The structure the RNA involved in interactions with A2486 is superimposed. Residues G2102 (2061) and G2482 (2447) are hydrogen bonded to the N6 of A2486 (2451) and G2482 which interacts with a neighboring phosphate group. (B) A skeletal representation with dashed hydrogen-bonds showing G2482, G2102, A2486 and the buried phosphate that is proposed to result in a charge relay through G2482 to the N3 of A2486.

(C) The normal and rarer imine tautomeric forms of G2482 and A2486 that are proposed to be stabilized by the buried phosphate of residue 2485.

Figure 17A:
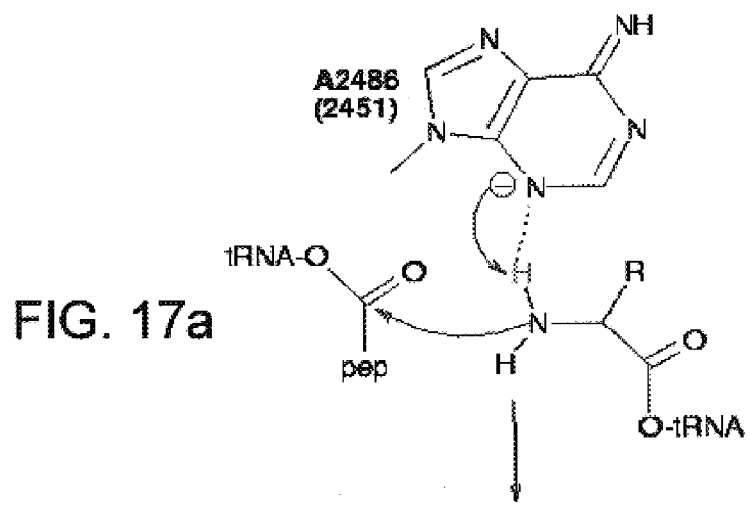
Figure 17B:
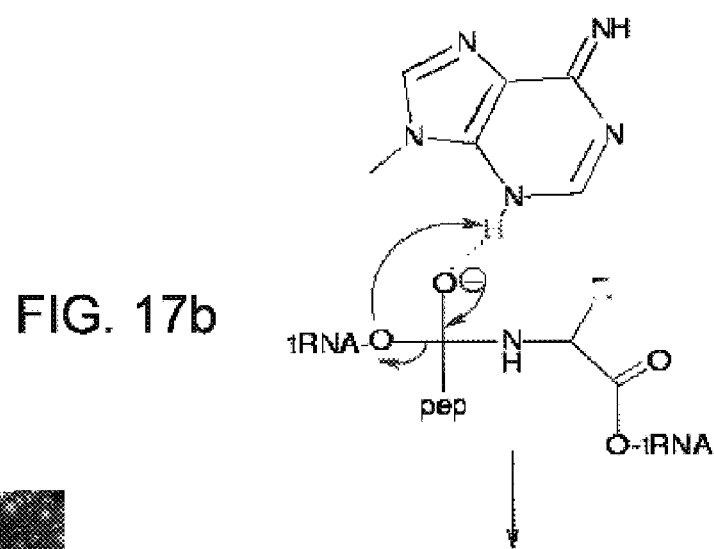
Figure 17C:
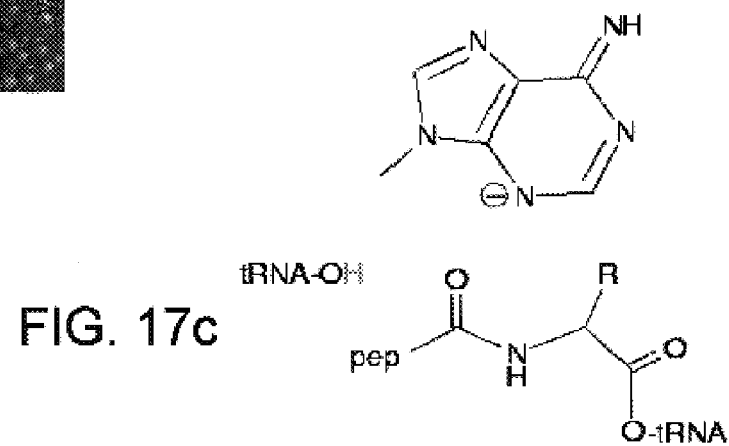

FIGS. 17A-C. The Proposed Mechanism of Peptide Synthesis Catalyzed by the Ribosome.

(A) The N3 of A2486 abstracts a proton from the αNH2 group as the latter attacks the carbonyl carbon of the peptidyl-tRNA.

(B) A protonated N3 stabilizes the tetrahedral carbon intermediate by hydrogen bonding to the oxyanion.

(C) The proton is transferred from the N3 to the peptidyl tRNA 3' OH as the newly formed peptide deacylates.

Figure 18A:
Figure 18B:
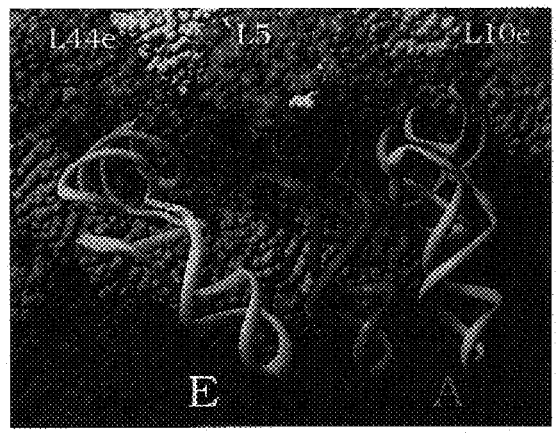

FIGS. 18A-B. A Space Filling Representations of the 50S Ribosomal Subunit with the 3 tRNA molecules, in the Same Relative Orientation that They are Found in the 70S Ribosome Structure by Noller and colleagues (Strobel, 2000), Docked onto the CCA's Bound in the A-Site and P-Site.

(A) The whole subunit in rotated crown view with the rRNA in yellow, proteins in pink and tRNAs in orange.

(B) A closeup showing the numbered proteins are in pink and the rRNA in blue. A backbone ribbon representation of the A-, P-, and E-sites are shown in yellow, red and white, respectively.

FIGS. 19A-F. The Polypeptide Exit Tunnel.

(A) The subunit has been cut in half roughly bisecting its central protuberance and its peptide tunnel along the entire length. The two halves have been opened like the pates of a book. All ribosome atoms are shown in CPK representation, with all RNA atoms that do not contact solvent shown in white and all protein atoms that do not contact solvent shown in green. Surface atoms of both protein and RNA are color-coded with carbon yellow, oxygen red, and nitrogen blue. A possible trajectory for a polypeptide passing through the tunnel is shown as a white ribbon. PT: peptidyl transferase site.

(B) Detail of the polypeptide exit tunnel showing distribution of polar and non-polar groups, with atoms colored as in (A), the constriction in the tunnel formed by proteins L22 and L4 (green patches close to PT), and the relatively wide exit of the tunnel. A modeled polypeptide is in white.

(C) The tunnel surface is shown with backbone atoms of the RNA color coded by domain. Domains I (white), II (light blue), III (gold), IV (green), V (orange), 5S (pink) and proteins are blue.

(D) A space filling representation of the large subunit surface at the tunnel exit showing the arrangement of proteins, some of which might play roles in protein secretion. The RNA is in white (bases) and yellow (backbone) and the numbered proteins are blue. A modeled polypeptide is exiting the tunnel in red.

(E) A closeup view of the half of the exit tunnel showing the relationship of the peptidyl transferase center (PTC) to proteins L4 (yellow) and L22 (blue). The Yarus inhibitor and a modeled peptide are purple and the 23S rRNA is in red and white.

(F) Secondary structure schematic of 23S rRNA identifying the sequences that contact the tunnel in red.

DETAILED DESCRIPTION OF THE INVENTION

Definitions

As used herein, "archaebacteria" refers to the kingdom of monerans that includes methane producers, sulfur-dependent species, and many species that tolerate very salty or hot environments.

As used herein, the term "atomic coordinates" or "structure coordinates" refers to mathematical coordinates that describe the positions of atoms in crystals of the ribosome or ribosomal subunit. The diffraction data obtained from crystals are used to calculate an electronic density map of the repeating unit of the crystal. The electron density maps are used to establish the positions (i.e. coordinates X, Y, and Z) of the individual atoms within a single ribosomal subunit in the crystal. Those of skill in the art understand that a set of structure coordinates determined by X-ray crystallography is not without standard error. For the purpose of this invention, any set of structure coordinates for a ribosome or ribosomal subunit from any source has a root mean square deviation of non-hydrogen atoms of less than 0.75 Å when superimposed on the nonhydrogen atom positions of the said atomic coordinates deposited at the Research Collaboratory for Structural Bioinformatics (RCSB) Protein Data Bank (PDB) (Berman et al., 2000, Nucleic Acids Research, 28, 235-242 with the accession numbers PDB ID: 1FFK, PDB ID: 1FFZ, and PDB ID: 1FGO.

In the list of atomic coordinates deposited at the RCSB Protein Data Bank, the term "atomic coordinate" refers to the measured position of an atom in the structure in Protein Data Bank (PDB) format, including X, Y, Z and B, for each. The assembly of "atomic coordinate" also refers to "atomic coordinates" or "structure coordinates". The term "atom type" refers to the element whose coordinates are measured. The first letter in the column defines the element. The term "X,Y, Z" refers to the crystallographically defined atomic position of the element measured with respect to the chosen crystallographic origin. The term "B" refers to a thermal factor that measures the mean variation of an atom's position with respect to its average position.

As used herein, the term "crystal" refers to any three-dimensional ordered array of molecules that diffracts X-rays.

As used herein, the term "untwinned" refers to a crystal cell the domains of which are aligned. The domains are also known as the "mosaic blocks". Most crystals diffract as though they were assemblies of mosaic blocks. One can think of them as small, perfectly ordered regions within the larger crystal, which, overall, is not so well ordered. Each block has the same symmetry and unit cell packing as all the others.

As used herein, the term "twinned" refers to a single microscopic crystal that contains microscopic domains of the same symmetry that differ significantly in orientation in such a way that the diffraction patterns of all are superimposed. In a twinned crystal the mosaic blocks, or domains, are not quite orientated so that some point in one direction and others point in a second, distinctly different direction, and the directions are such that the diffraction pattern generated by one group of blocks falls exactly on top of the diffraction pattern of the other group.

As used herein, the term "complex" refers to the assembly of two or more molecules to yield a higher order structure as with the 50S ribosomal subunit bound to CCdA-p-Puro or aminoacyl t-RNA analogue.

As used herein, the term "carrier" in a composition refers to a diluent, adjuvant, excipient, or vehicle with which the product is mixed.

As used herein, the term "composition" refers to the combining of distinct elements or ingredients to form a whole. A composition comprises more than one element or ingredient. For the purposes of this invention, a composition will often, but not always, comprise a carrier.

As used herein, the term "crystallographic origin" refers to a reference point in the unit cell with respect to the crystallographic symmetry operation.

As used herein, the term "unit cell" refers to a basic parallelpiped shaped block. The entire volume of crystal may be constructed by regular assembly of such blocks. Each unit cell comprises a complete representation of the unit of pattern, the repetition of which builds up the crystal.

As used herein, the term "space group" refers to the arrangement of symmetry elements of a crystal.

As used herein, the term "symmetry operation" refers to an operation in the given space group to place the same atom in one asymmetric unit cell to another.

As used herein, the term "asymmetric unit" refers to a minimal set of atomic coordinates that can be used to generate the entire repetition in a crystal.

As used herein, the term "heavy atom derivatization" refers to the method of producing a chemically modified form, also known as "heavy atom derivatives", of crystals of the ribosome and the ribosomal subunit and its complexes. In practice, a crystal is soaked in a solution containing heavy atom metal atom salts or organometallic compounds, e.g., mercury chlorides, ethyl-mercury phosphate, osmium pentamine, or iridium pentamine, which can diffuse through the crystal and bind to the ribosome or ribosomal subunit. The location(s) of the bound heavy metal atom(s) can be determined by X-ray diffraction analysis of the soaked crystal. This information, in turn, is used to generate the phase information used to construct three-dimensional structure of the complex (Blundel, T. L., and Johnson, N. L., Protein Crystallography, Academic Press, 1976).

As used herein, the term "SAR", an abbreviation for Structure-Activity Relationships, collectively refers to the structure-activity/structure property relationships pertaining to the relationship(s) between a compound's activity/properties and its chemical structure.

As used herein, the term "molecular structure" refers to the three dimensional arrangement of molecules of a particular thing (e.g., the three dimensional structure of the molecules that make up a ribosome or ribosomal subunit and ligands that interact with ribosomes and ribosomal subunits, particularly with the large ribosomal subunits, more particularly with the 50S ribosomal subunits).

As used herein, the term "molecular modeling" refers to the use of computers to draw realistic models of what molecules look like and to make predictions about structure activity relationships of ligands. The methods used in molecular modeling range from molecular graphics to computational chemistry.

As used herein, the term "molecular model" refers to the three dimensional arrangement of the atoms of a molecule connected by covalent bonds.

As used herein, the term "molecular graphics" refers to 3D representations of the molecules, preferably on a computer screen.

As used herein, the term "computational chemistry" refers to calculations of the physical and chemical properties of the molecules.

As used herein, the term "MIR" refers to multiple isomorphous replacement, a technique used for deriving phase information from crystals treated with heavy atom compounds.

As used herein, the term "MAD" refers to the multiple-wavelength anomalous dispersion method for determining the phases of X-ray diffraction patterns. X-ray diffraction experiments are carried out using the tunable X-ray sources at-several wavelengths, and depend on the presence of atoms in the crystal in question, the scattering properties of which depend significantly on X-ray wavelength.

As used herein, the term "molecular replacement" refers to a method that involves generating a preliminary model of a crystal of the ribosome or ribosomal subunit whose coordinates are unknown, by orienting and positioning the said atomic coordinates described in the present invention so as best to account for the observed diffraction pattern of the unknown crystal. Phases can then be calculated from this model and combined with the observed amplitudes to give an approximate Fourier synthesis of the structure whose coordinates are unknown. (Rossmann, M. G., ed., "The Molecular Replacement Method", Gordon & Breach, New York, 1972).

As used herein, the term "homologue" refers to the RNA or protein of a ribosome, ribosomal subunit, or a functional domain from a ribosome or ribosomal subunit from a first source having at least 25% sequence identity, or at least 30% sequence identity, or at least 35% sequence identity, or at least 40% sequence identity, or at least 45% sequence identity, or at least 50% sequence identity, or at least 55% sequence identity, or at least 60% sequence identity, or at least 65% sequence identity, or at least 70% sequence identity, or at least 75% sequence identity, or at least 80% sequence identity, or more preferably at least 85% sequence identity, or even more preferably at least 90% sequence identity, and most preferably at least 95% sequence identity, with the RNA or protein from a corresponding ribosome, ribosomal subunit or any functional domain thereof, from a second source. The second source may be from the same or a different species than that of the first source.

As used herein, the term "active site" refers to regions on a ribosome or ribosomal subunit that are directly involved in protein synthesis, e.g. the peptidyl transferase site, the factor binding site, and other similar sites.

As used herein, the term "naturally occurring amino acids" refers to the L-isomers of the naturally occurring amino acids. The naturally occurring amino acids are glycine, alanine, valine, leucine, isoleucine, serine, methionine, threonine, phenylalanine, tyrosine, tryptophan, cysteine, proline, histidine, aspartic acid, asparagine, glutamic acid, glutamine, γ-carboxylglutamic acid, arginine, omithine, and lysine. Unless specifically, indicated, all amino acids are referred to in this application are in the L-form.

As used herein, the term "unnatural amino acids" refers to amino acids that are not naturally found in proteins. For example, selenomethionine.

As used herein, the term "positively charged amino acid" includes any amino acids having a positively charged side chain under normal physiological conditions. Examples of positively charged naturally occurring amino acids are arginine, lysine, and histidine.

As used herein, the term "negatively charged amino acid" includes any amino acids having a negatively charged side chains under normal physiological conditions. Examples of negatively charged naturally occurring amino acids are aspartic acid and glutamic acid.

As used herein, the term "hydrophobic amino acid" includes any amino acids having an uncharged, nonpolar side chain that is relatively insoluble in water. Examples of naturally occurring hydrophobic amino acids are alanine, leucine, isoleucine; valine, proline, phenylalanine, tryptophan, and methionine.

As used herein, the term "hydrophilic amino acid" refers to any amino acids having an uncharged, polar side chain that is relatively soluble in water. Examples of naturally occurring hydrophilic amino acids are serine, threonine, tyrosine, asparagine, glutamine and cysteine.

As used herein, the term "hydrogen bond" refers to two hydrophilic atoms (either O or N), which share a hydrogen that is covalently bonded to only one atom, while interacting with the other.

As used herein, the term "hydrophobic interaction" refers to interactions made by two hydrophobic residues or atoms (such as C).

As used herein, the term "conjugated system" refers to more than two double bonds are adjacent to each other, in which electrons are completely delocalized with the entire system. This also includes and aromatic residues.

As used herein, the term "aromatic residue" refers to amino acids which side chains have delocalized conjugated system. Examples of aromatic residues are phenylalanine, tryptophan, and tyrosine.

As used herein, the term "active form" of a ribosome or ribosomal subunit refers to the ribosome or ribosomal subunit in a state that renders it capable of protein synthesis.

As used herein, the term "competitive inhibitor" refers to inhibitors that bind to the active form of ribosome or ribosomal subunit at the same sites as its substrate(s) or tRNA(s), thus directly competing with them. Competitive inhibition can be reversed completely by increasing the substrate or tRNA concentration.

As used herein, the term "uncompetitive inhibitor" refers to one that inhibits the functional activity of a ribosome or ribosomal subunit by binding to a different site on the ribosome or ribosomal subunit than does its substrates, or tRNA. Such inhibitors can often bind to the ribosome or ribosomal subunit with the substrate or tRNA and not to the ribosome or ribosomal subunit by itself. Uncompetitive inhibition cannot be reversed completely by increasing the substrate concentration.

As used herein, the term "non-competitive inhibitor" refers to one that can bind to either the free or substrate or tRNA bound form of the ribosome or ribosomal subunit.

Those of skill in the art may identify inhibitors as competitive, uncompetitive, or non-competitive by computer fitting enzyme kinetic data using standard equation according to Segel, I. H., Enzyme Kinetics, J. Willey & Sons, (1975). It should also be understood that uncompetitive or non-competitive inhibitors according to the present invention may bind the same or different binding site of puromycin.

As used herein, the term "R or S-isomer" refers to two possible stereoisomers of a chiral carbon according to the Cahn-Ingold-Prelog system adopted by International Union of Pure and Applied Chemistry (IUPAC). Each group attached to the chiral carbon is first assigned to a preference or priority a, b, c, or d on the basis of the atomic number of the atom that is directly attached to the chiral carbon. The group with the highest atomic number is given the highest preference a, the group with next highest atomic number is given the next highest preference b; and so on. The group with the lowest preference (d) is then directed away from the viewer. If the trace of a path from a to b to c is counter clockwise, the isomer is designated (S); in the opposite direction, clockwise, the isomer is designated (R).

As used herein, the term "ribosome" refers to an assembled ribosome comprising the large and small subunit.

As used herein, the term "ribosomal subunit" refers to one of the two portions of the ribosome that functions independently during the initiation phase of protein synthesis. For example, a prokaryotic ribosome comprises a 50S subunit and a 30S subunit.

Ribosomal proteins are designated "SX" or "LX", where S stands for "small subunit", X is an integer, and L stands for "large subunit", and X is an integer.

As used herein, the term "ligand" refers to any atom, molecule, or chemical group which binds with a ribosome, ribosomal subunit or ribosome fragment. Thus, ligands include, but are not limited to, a single heavy atom, an antibiotic, a tRNA, a peptidyl transferase, or a signal recognition particle ("SRP").

As used herein the terms "bind", "binding", "bond", "bonded", when used in reference to the association of atoms, molecules, or chemical groups, refer to any physical contact or association of two or more atoms, molecules, or chemical groups (e.g., the binding of a ligand with a ribosomal subunit refers to the physical contact between the ligand and the ribosomal subunit). Such contacts and associations include covalent and non-covalent types of interactions.

As used herein, the terms "covalent bond" or "valence bond" refer to a chemical bond between two atoms in a molecule created by the sharing of electrons, usually in pairs, by the bonded atoms.

As used herein, "noncovalent bond" refers to an interaction between atoms and/or molecules that does not involve the formation of a covalent bond between them.

Specific Embodiments

A. Atomic Structure of the Large Ribosomal Subunit at 2.4 Å Resolution

The present invention is based in part on the development of a novel method for preparing crystals of ribosomes. The novel method provides crystals of the 50S ribosomal subunit that are much thicker than those available earlier and that can diffract X-rays to about 2.4 Å resolution. The newly developed method eliminates the twinning of crystals that obstructed progress in determining the crystal structure of the 50S ribosomal subunit from H. marismortui for many years. The method of preparing the crystals of the 50S ribosomal subunit is discussed below.

The present invention is also based in part on the atomic structure of the crystal of the 50S ribosomal subunit from H. marismortui that has been derived from a 2.4 Å resolution electron density map that was experimentally phased using heavy atom derivatives. The atomic coordinates of the structure were deposited on Jul. 10, 2000, at Research Collaboratory for Structural Bioinformatics (RCSB) Protein Data Bank (PDB) (Berman et al., 2000, Nucleic Acid Research, 28, 235-242; available at the web site,—www.rcsb.org/pdb/) with accession number PDB ID: 1FFK.

Moreover, the present invention is based on the derivation from the atomic coordinates of the following model which is briefly summarized here and discussed in detail in the following sections of the specification. The model includes 2,811 of the 2,923 nucleotides of 23S rRNA, all 122 nucleotides of its 5S rRNA, and structures for the 27 proteins that are well-ordered in the subunit.

The secondary structures of both 5S and 23S rRNA are remarkably close to those deduced for them by phylogenetic comparison. The secondary structure of the 23S rRNA divides it into 6 large domains, each of which has a highly asymmetric tertiary structure. The irregularities of their shapes notwithstanding, the domains fit together in an interlocking manner to yield a compact mass of RNA that is almost isometric. The proteins are dispersed throughout the structure, concentrated largely on its surface, but they are not found in the regions of the subunit that are of primary functional significance to protein syntheses—the 30S subunit interface, the binding regions for tRNA and the peptidyl transferase active site. The most surprising feature of many of these proteins are the extended, irregular structures of their loops and termini, which penetrate between RNA helices. The primary role of most of the proteins in the subunit appears to be stabilization of the three-dimensional structure of its rRNA.

1. Preparation of the Crystal for the 50S Ribosomal Subunit and Structure Determination Several experimental approaches were used to extend the resolution of the electron density maps of the H. marismortui 50S ribosomal subunit from 5 Å to 2.4 Å including improvements in the crystals. A back-extraction procedure was developed for reproducibly growing crystals that are much thicker than those available earlier and can diffract to 2.2 Å resolution (See Example 1). Briefly, the crystals were grown at room temperature in hanging drops by vapor diffusion from seeded solutions back-extracted from precipitated subunits. The crystals that resulted had maximum dimensions of 0.5×0.5× 0.2 mm and were harvested after three weeks. The twinning of crystals that obstructed progress for many years (Ban et al., 1999) was eliminated by adjusting crystal stabilization conditions (See Example 1). Crystals were stabilized by gradual transfer into a solution containing 12%, PEG 6000, 22% ethylene glycol, 1.7 M NaCl, 0.5 M $NH_4Cl$, 100 mM potassium acetate, 30 mM $MgCl_2$ and 1 mM $CdCl_2$, pH 6.2, and flash frozen in liquid propane. Reducing the salt concentration below 1.7 M NaCl (KCl) increased the tendency of crystals to become twinned. At salt concentrations as low as 1.2 M nearly all of the crystals were twinned.

All the X-ray data used for high resolution phasing were collected at the Brookhaven National Synchrotron Light Source except for two native data sets used, which were collected at the Advanced Photon Source at Argonne (See Example 2) (Table 1). Osmium pentamine (132 sites) and Iridium hexamine (84 sites) derivatives proved to be the most effective in producing both isomorphous replacement and anomalous scattering phase information to 3.2 Å resolution (See Example 2). Inter-crystal density averaging which had contributed significantly at lower resolution, was not helpful beyond about 5 Å resolution. Electron density maps were dramatically improved and their resolutions extended, eventually to 2.4 Å, using the solvent flipping procedure in CNS (Abrahams et al., 1996; Brunger et al., 1998).

TABLE 1

Statistics for Data Collection, Phase Determination, and Model Construction.

Data statistics

| | MIRAS1 | | | MIRAS2 | | | |
|---|---|---|---|---|---|---|---|
| | Native1 | $Os(NH_3)_5^{2+}$ | $UO_2F_5^{3-}$ | Native2 | $Ir(NH_3)_6^{3+}$ | $Os(NH_3)_6^{3+}$ | $Ta_6Br_{12}^{2+}$ |
| Heavy atom conc. (mM) | — | 30.0 | 0.5 | — | 20.0 | 4.5 | 3.0 |
| Soaking time (hrs) | — | 1.5 | 4 | — | 24 hrs | 24 hrs | 24 hrs |
| Sites no. | — | 132 | 20 | — | 84 | 38 | 9 |
| Resolution (A) | 90-2.4 | 40-3.5 | 40-3.8 | 30-2.9 | 30-3.2 | 30-3.5 | 30-3.8 |
| (*) | (2.5-2.4) | (3.6-3.5) | (3.9-3.8) | (3.0-2.9)(3.32-3.22) | (3.27-3.20) | (3.6-3.5) | (3.97-3.80) |
| λ(Å) | 1.00 | 1.14 | 1.30 | 1.00 | 1.075 | 1.14 | 1.255 |
| Observations | 6,089,802 | 1,308,703 | 596,166 | 2,832,360 | 1,823,861 | 1,646,468 | 1,288,524 |
| Unique | 665,928 | 429,761 | 313,863 | 390,770 | 541,488 | 488,275 | 346,745 |
| Redun. (*) | 9.1(6.5) | 3.0(2.5) | 1.9(1.6) | 7.2 | 3.4 | 4.3(4.2) | 3.7 |
| Completeness(*) | 95.6(71.0) | 99.4(96.8) | 92.0(54.1) | 97.1 | 93.8 | 98.1(99.0) | 99.5 |
| I/σI(Last bin) | 25.5(1:9) | 13.5(3.3) | 8.9(1.6) | 18.0(6.4) | 12.0(2.6) | 10.6(2.7) | 10.8(3.2) |
| $R_{merge}$(*) | 8.6(69.1) | 7.2(32.0) | 9.1(37.9) | 11.2(36.9) | 8.5(29.5) | 12.1(46.0) | 12.1(40.5) |
| $\chi^2$(ano)(*) | — | 2.8(1.0) | 1.5(1.0) | — | 2.63(1.48) | 1.8(1.0) | 2.42(1.18) |
| $R_{merge}$(ano) | — | — | 6.2 | 8.0 | — | 6.7 | 6.9 |
| $R_{iso}$ | — | 14.1(22.7) | 26.4(47.0) | — | 12.9(28.1) | 19.5(39.4) | — |

Phasing Statistics

Resolution shells (Å): ~73,200 reflections per bin

| | 30.0 | 5.1 | 4.0 | 3.5 | 3.2 | Total |
|---|---|---|---|---|---|---|
| MIRAS1 (FOM) | | 0.52 | 0.31 | 0.14 | — | 0.32 |
| $Os(NH_3)_5^{2+}$ | | | | | | |
| Phasing power | | 0.87 | 0.72 | 0.66 | — | 0.75 |
| Phasing power (SAD) | | 1.40 | 0.58 | 0.26 | — | 0.75 |
| $R_{cullis}$(centric) | | 0.62 | 0.65 | 0.67 | — | 0.65 |
| $UO_2F_5^{3+}$ | | | | | | |
| Phasing Power | | 0.47 | 0.33 | 0.28 | — | 0.36 |
| Phasing power (SAD) | | 0.46 | 0.25 | — | — | 0.36 |
| $R_{cullis}$(centric) | | 0.72 | 0.77 | 0.75 | — | 0.75 |
| MIRAS2 (FOM) | | 0.48 | 0.40 | 0.28 | 0.12 | 0.33 |
| $Ir(NH_3)_6^{3+}$ | | | | | | |
| Phasing power | | 1.02 | 0.92 | 0.78 | 0.66 | 0.89 |
| Phasing power (SAD) | | 2.02 | 1.60 | 1.22 | 0.83 | 1.47 |
| $R_{cullis}$ (centric) | | 0.58 | 0.63 | 0.70 | 0.74 | 0.63 |
| $Os(NH_3)_6^{3+}$ | | | | | | |
| Phasing power | | 0.62 | 0.57 | 0.58 | 0.58 | 0.59 |
| Phasing power (SAD) | | 0.47 | 0.39 | — | — | 0.42 |
| $R_{cullis}$(centric) | | 0.78 | 0.78 | 0.78 | 0.76 | 0.78 |
| $Ta_6Br_{12}^{2+}$(Used for SAD phasing only) | | | | | | |
| Phasing Power (SAD) | | 2.77 | 0.35 | 0.13 | — | 1.19 |
| $FOM_{(MIRAS1+MIRAS2+SAD)}$ | | 0.76 | 0.51 | 0.31 | 0.14 | 0.37 |

Model Statistics

| Resolution range (Å) | 90.0-2.4 | ms deviations: | | Average B factors (Å$^2$) | |
|---|---|---|---|---|---|
| Reflections | 577,304 | Bonds (Å) | 0.0064 | All atoms | 37.4 |
| $R_{cryst}$(%) | 25.2 | Angles(°) | 1.19 | 23S rRNA | 32.3 |
| $R_{free}$(%) | 26.1 | Dihedrals(°) | 28.8 | 5S rRNA | 43.2 |
| | | Impropers(°) | 1.68 | Minimum/Max B factors (Å$^2$) | 70/107.9 |

HA, heavy-atom concentrations; ST, soaking time; Res, resolution; λ, wavelength; Obs, observations; Redun., redundancy; Compl., completeness; (*) last-resolution shell. $R_{iso}$: $\Sigma|F_{PH} - F_P|/\Sigma F_{PH}$, where $F_{PH}$ and $F_P$ are the native structure factor amplitudes, respectively. $R_{sym}$: $\Sigma\Sigma_i|I_{(h)} - I_{(h)i}|/\Sigma\Sigma:I_{(h)i}$, where I(h) is the mean intensity after reflections. Phasing power: r.m.s. isomorphous difference divided by the r.m.s. residual lack of closure $R_{cullis}$: $\Sigma(||F_{PH} - F_P| - |F_H$ $_{(calc)}||)/\Sigma|F_{PH} - F_{P|, where\ FPH}$ is the structure factor of the derivative and $F_P$ is that of the native data. The summation is valid only for centric reflection. FOM (Figure of merit): mean value of the cosine of the error in phase angles. Abbreviations: MIRAS: multiple isomorphous replacement, anomalous scattering; SAD: single wavelength anomalous diffraction; FOM: figure of merit.

Figure 1E:
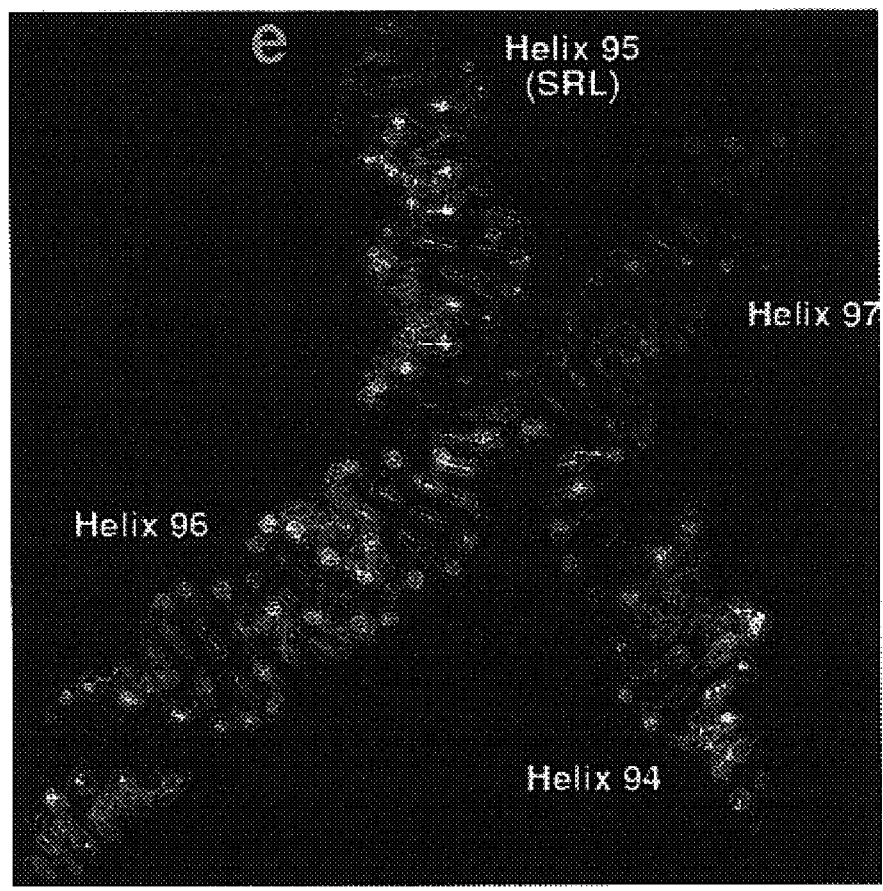

Except for regions obscured by disorder, the experimentally-phased, 2.4 Å resolution electron density map was of sufficient quality so that both protein and nucleic acid sequencing errors could be identified and corrected. Each nucleotide could be fitted individually and the difference between A and G was usually clear without reference to the chemical sequence, as was the distinction between purines and pyrimidines (FIG. 1). Only a few of the many water molecules and metal ions evident in the electron density have been positioned so far.

Subtraction of the atomic model from the experimental electron density map leaves no significant density except for water and ions, showing that the model accounts for all the macromolecular density. Preliminary refinement of the model was achieved using a mixed target in the program CNS (Brunger et al., 1998). The model was further refined in real space against the 2.4 Å electron density map using the program TNT (Tronrud et al., 1997), which yielded a model with a free R-factor of 0.33. One additional round of mixed target refinement of both atomic positions and B-factors using CNS led to the structure described below. Its free R-factor is 0.27 (Table 1).

The atomic coordinates derived from the electron density map were deposited on Jul. 10, 2000, at RCSB Protein Data Bank with an accession code PDB ID: 1FFK.

2. Sequence Fitting and Protein Identification

The sequence of 23S rRNA was fit into the electron density map nucleotide by nucleotide starting from its sarcin/ricin loop sequence (A2691-A2702 (*E. coli* numbers A2654 to A2665), whose position had been determined at 5 Å resolution (Ban et al., 1999). Guided by the information available about the secondary structures of 23S rRNAs (Gutell, 1996), the remaining RNA electron density neatly accommodated the sequence of 5S rRNA. The interpretation of protein electron density corresponding to the protein was more complicated because each protein region had to be identified chemically before the appropriate sequence could be fit into it, but with the assistance of Daniel Kline, Lu Min, Snjezana Antolic, and Martin Schmeing, ~4,000 amino acid residues were fit into electron density.

The *H. marismortui* 50S subunit appears to contain 31 proteins, and there are sequences in the Swiss-Prot data bank for 28 of them, including one, HMS6 or L7ae, that was originally assigned to the small ribosomal subunit (Whittmann-Liebold et al., 1990) The three remaining proteins were identified using the sequences of the ribosomal proteins from eukaryotes and other archeal species as guides. No electron density was found for one of the *H. marismortui* large ribosomal subunit proteins in the sequence database, LX. Either the assignment of LX to the large subunit is in error, or LX is associated with a disordered region of the subunit, or LX is absent from the subunits examined altogether.

The 2.4 Å resolution electron density map lacks clear electron density for proteins L1, L10, L11 and L12, the positions of which are known from earlier low resolution X-ray and/or electron microscopic studies. These proteins are components of the two lateral protuberances of the subunit, which are both poorly ordered in these crystals. L1 is the sole protein component of one of them (Oakes et al., 1986) and is evident in 9 Å resolution density maps of the subunit (Ban et al., 1998), but not at higher resolutions. L10, L11 and L12 are components of the other protuberance, which is often referred to as the L7/L12 "stalk" (Oakes et al., 1986). L11 and the RNA to which it binds were located in the 5 Å resolution electron density map of the *H. marismortui* large subunit (Ban et al., 1999) using the independently determined crystal structures of that complex (Conn et al., 1999; Wimberly et al., 1999). A protein fragment (~100 residues) that is associated with the RNA stalk that supports the L11 complex can be seen in the 2.4 Å resolution map. Based on location, it must be part of L10. There is no electron density corresponding to L12 seen at any resolution, but the L12 tetramer is known to be attached to the ribosome through L10, and the L10/L12 assembly is known to be flexible under some circumstances (Moller et al., 1986), which may explain its invisibility here.

The structures of eubacterial homologues of proteins L2, L4, L6, L14, and L22 have previously been determined in whole or in part (see Table 2). L2, L6 and L14 were initially located in the 5 Å resolution map (Ban et al., 1999). L4 and L22 have now been identified and positioned the same way. Electron density corresponding to most of the remaining proteins was assigned by comparing chain lengths and sequence motifs deduced from the electron density map with known sequence lengths, guided by the information available about relative protein positions (Walleczek et al., 1988) and protein interactions with 23S rRNA and 5S rRNA (Ostergaard et al., 1998). Each of the protein electron density regions so identified is well accounted for by its amino acid sequence.

The most interesting of the proteins identified by sequence similarity was L7ae, which first appeared to be L30e. The L30e identification seemed plausible because the structure of yeast L30 superimposes neatly on the electron density of L7ae, and the structure of the RNA to which L7ae binds closely resembles that of the RNA to which yeast L30 binds (Mao et al., 1999). Nevertheless, the sequence of HMS6, which by sequence similarity is a member of the L7ae protein family, fits the electron density better. Four of the other proteins identified by sequence similarity, L24e, L37e, L37ae, and L44e, contain zinc finger motifs. The rat homologues of L37e and L37ae were predicted to be zinc finger proteins on the basis of their sequences (Wool et al., 1995), and this prediction helped identify their homologues in *H. marismortui*.

TABLE 2

Large Subunit Proteins from *Haloarcula Marismortui*

| Name[1] | Hmlg[2] | Lgth[3] | Conf[4] | Interactions[5] | | | | | | 5S Proteins |
|---|---|---|---|---|---|---|---|---|---|---|
| | | | | 1 | 2 | 3 | 4 | 5 | 6 | |
| L1* | | 211 | glb. | | | | | + | | none |
| L2† | RL8 | 239 | glb + ext | | + | + | + | + | | (L37ae) |
| L3 | RL3 | 337 | glb + ext | | ± | | + | + | + | L14, L24e, (L13) |
| L4† | RL4 | 246 | glb + ext | + | + | | | ± | | (L18e), (L24), (L37e) |
| L5 | RL11 | 176 | glb | | | | | + | | + L18 |
| L6 | RL9 | 177 | glb | | ± | | | ± | + | (L13) |
| L10* | RP0 | 348 | glb? | | + | | | | | L12 |

TABLE 2-continued

Large Subunit Proteins from *Haloarcula Marismortui*

| Name[1] | Hmlg[2] | Lgth[3] | Conf[4] | 1 | 2 | 3 | 4 | 5 | 6 | 5S | Proteins |
|---|---|---|---|---|---|---|---|---|---|---|---|
| L11* | RL12 | 161 | glb | | + | | | | | | none |
| L12* | RL1/2 | 115 | glb | | | | | | | | L10 |
| L13 | RL13a | 145 | glb | | + | | | ± | ± | | (L3),(L6) |
| L14 | RL23 | 132 | glb | | | | + | + | + | | L3,L24e |
| L15 | RL27a | 164 | glb + ext | + | + | | | + | | | (L18e), (L32e) |
| L18 | RL5 | 186 | glb + ext | | ± | | | + | | + | L5,L21e |
| L19 | RL19 | 148 | glb + ext | | + | + | + | | ± | | none |
| L22 | RL17 | 154 | glb + ext | + | ± | + | + | + | + | | none |
| L23 | RL23a | 84 | glb | ± | + | | | | | | L29, (L39e) |
| L24 | RL26 | 119 | glb + ext | + | | | | | | | (L4) |
| L29 | RL35 | 70 | glb | + | | | | | | | L23 |
| L30 | RL7 | 154 | glb | | + | | | | | + | none |
| L18e | RL18 | 115 | glb | | + | | | | | | (L4),(L15) |
| L21e | RL21 | 95 | glb | | + | | | + | | ± | L18 |
| L24e | RL24 | 66 | glb | | | | ± | | + | | L3,L14 |
| L31e | RL31 | 91 | glb | | | + | + | + | | | none |
| L32e | RL32 | 240 | glb | ± | + | | | | | | (L15) |
| L37e | R137 | 56 | glb + ext | + | + | + | ± | | | | (L4) |
| L39e | RL39 | 49 | ext | + | | + | | | | | (L23) |
| L44e | RL36a | 92 | glb + ext | + | | | ± | + | | | (L15e) |
| L7ae | R27a | 110 | glb | + | | | | | | | L15e |
| L10e | RL10 | 163 | glb | | + | | | + | | ± | none |
| L15e | RL15 | 184 | glb + ext | + | ± | ± | ± | + | | | (L44e), L7ae |
| L37ae | RL37a | 72 | glb + ext | | + | + | | | | | L2 |

The top block of proteins include all those known to have eubacterial homologs of the same name. The second block lists proteins found in the *H. marismortui* large ribosomal subunit that have only eukaryotic homologs (Whitiman-Liebold et al., 1990). Their names are all followed by the letter "e" to distinguish them from eubacterial proteins that would otherwise have the same name. The third block are large subunit proteins for which no *H. marismortui* sequence yet exists. They are identified by sequence homology using standard L names.

[1] The structures of all or part of homologs of the following proteins were previously determined: L1 (Nevskaya et al., 2000), L2 (Nakagawa et al, 1999), L4 (Wahl, et al., 2000), L6 (Golden et al., 1993), L11 (Conn et al., 1999; Wimberly et al., 1999; Markus et al., 1997), L12 (Leijonmarck et al., 1980), L14 (Davies et al., 1996), L22 (Unge et al., 1998), L30 (Wilson et al., 1986). All other structures, except 10, have been newly determined in this study.
[2] Rat homolog. Rat equivalents to *H. marismortui* proteins are from (Mao et al., 1999).
[3] Sequence chain length
[4] Conformation: glb = g lobular; ext = extension
[5] The protein interactions with the 6 domains of 23S rRNA, 5S rRNA and other proteins are specified. (+) implies that the interaction is substantial. (±) implies a weak, tangential interaction. Protein names are shown in parentheses implies that the interactions are weak; otherwise, the interaction is substantial.
*All entries so designated describe proteins that are not fully represented in the electron density maps described here. The summary information provided is derived from literature sources and is included here for completeness only.
†The structure available for this protein in isolation does not include the extension(s) reported here.

3. General Appearance of the Subunit

In its crown view (FIG. 2), the large ribosomal subunit, which is about 250 Å across, presents its surface that interacts with the small subunit to the viewer with the three projections that radiate from that surface pointed up. Although the protuberance that includes L1 is not visible in the 2.4 Å resolution electron density map, the structure of L1, which has been determined independently (Nikonov et al., 1996), has been positioned approximately in lower resolution maps (Ban et al., 1998) and is included here to orient the reader. It is evident that, except for its two lateral protuberances, the large ribosomal subunit is monolithic. There is no hint of a division of its structure into topologically separate domains. In addition, partly because it lacks obvious domain substructure but also because it is so large, it is impossible to comprehend looking at it as a whole. In order to convey to the reader a sense of how it is put together, the subunit must be dissected into its chemical components.

4. RNA Secondary Structure

All the base pairs in *H. marismortui* 23S rRNA stabilized by at least 2 hydrogen bonds were identified using a computer program that searched the structure for hydrogen bond donors and acceptors separated by less than 3.2 Å. Bases linked by at least two such bonds were considered paired if the angle between their normals was less than 45° and the angle between bonds and base normals was less than 45° also. Based on the results of this analysis, a secondary structure diagram has been prepared in the format standard for 23S/28S rRNAs (FIG. 3). Clearly the secondary structure predicted for this molecule by phylogenetic comparison was remarkably accurate, but it did not find all of the tertiary pairings and failed to identify interactions involving conserved bases. In addition to base pairs of nearly every type, the RNA contains numerous examples of well-known secondary structure motifs such as base triples, tetraloops, and cross-strand purine stacks, but no dramatically new secondary structure motifs have been identified so far.

The secondary structure of this 23S rRNA consists of a central loop that is closed by a terminal stem, from which 11 more or less complicated stem/loops radiate. It is customary to describe the molecule as consisting of 6 domains, and to number its helical stems sequentially starting from the 5' end (FIG. 4) (Leffers et al., 1987). The division of the molecule into domains shown in FIG. 4 deviates from standard practice with respect to helix 25, which is usually considered to be part of domain I. It is placed in domain II because it interacts more strongly with domain II than it does with the other elements of domain I.

There are five sequences longer than 10 nucleotides in 23S rRNA whose structures cannot be determined from the 2.4 Å resolution map due to disorder. Altogether they account for 207 out of the 232 nucleotides missing from the final model. The disordered regions are: (1) all of helix 1, (2) the distal end of helix 38, (3) helix 43/44 to which ribosomal protein L11 binds, (4) the loop end of stem/loop 69, and (5) helix 76/77/78, which is the RNA structure to which L1 binds. For completeness, these regions are included in FIG. 3 (in gray) with the secondary structures determined for them phylogenetically.

5. Overall Architecture of rRNA

Figure 4A:
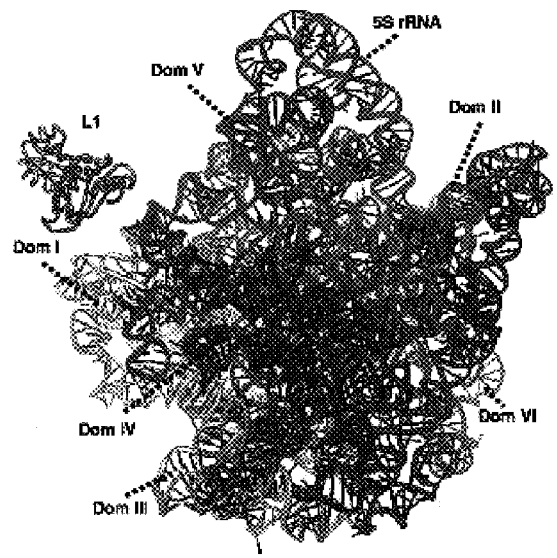
Figure 4B:
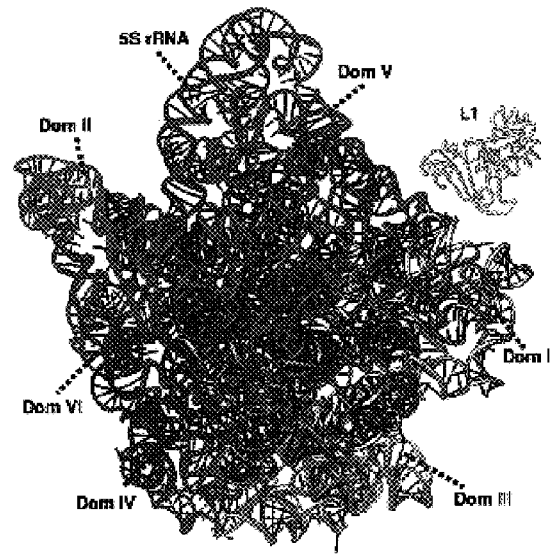
Figure 4C:
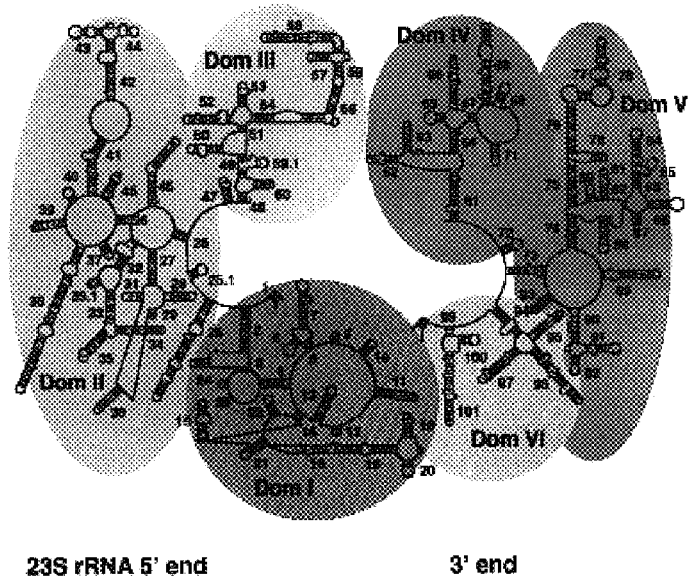

The six domains of 23S rRNA and 5S rRNA all have complicated, convoluted shapes that nevertheless fit together to produce a compact, monolithic RNA mass (FIG. 4A, B). Thus despite the organization of its RNAs at the secondary structure level, in three dimensions, the large subunit is a single, gigantic domain. In this respect it is quite different from the small subunit, which is a flatter object that is not at all monolithic. Even in low resolution electron micrographs the small subunit consists of three structural domains, each of which, it turns out, contains one of the three secondary structure domain of its RNA (Noller et al., 1990). This qualitative difference between the two subunits may reflect a requirement for conformational flexibility that is greater for the small subunit.

Domain I, which looks like a mushroom (FIG. 4E), lies in the back of the particle, behind and below the L1 region. The thin part of the domain starts in the vicinity of domain VI, which is where its first and last residues are located. Helices 1 and 25 span the particle in the back and then the domain expands into a larger, more globular structure below and behind the L1 region.

Figure 4D:
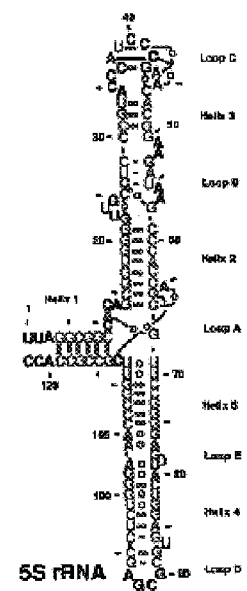
Figure 4E:
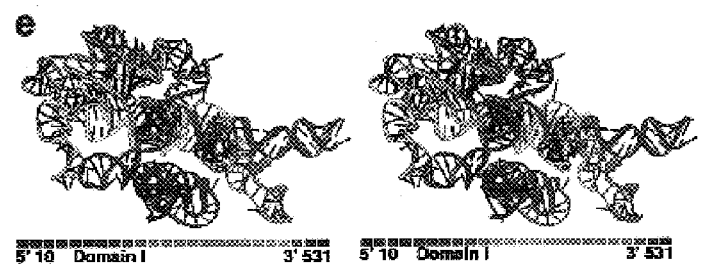
Figure 4F:
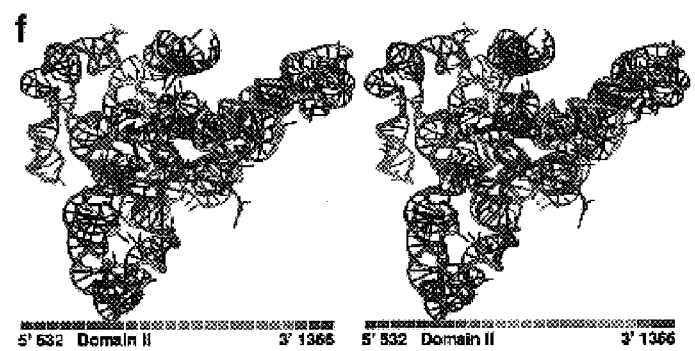

The largest of the six 23S rRNA domains, domain II, which accounts for most of the back of the particle, has three protrusions that reach towards the subunit interface side of the particle (FIG. 4F). One of them (helix 42-44) is the RNA portion of the L7/L12 stalk, which is known to interact with elongation factors, is not well-ordered in these crystals. The second domain II protrusion is helix 38, which is the longest, unbranched stem in the particle. It starts in the back of the particle, bends by about 90 degrees and protrudes towards the small subunit between domains V and 5S rRNA. The third region, helix 32-35.1, points directly towards the small subunit and its terminus, the loop of stem/loop 34, interacts directly with the small ribosomal subunit (Culver et al., 1999). This loop emerges at the subunit interface between domains III and IV.

Figure 4G:
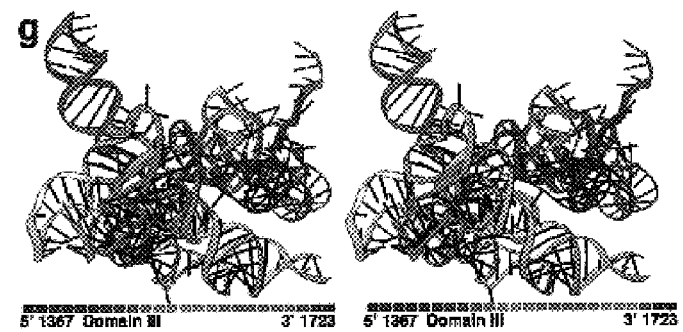

Domain III is a compact globular domain that occupies the bottom left region of the subunit in the crown view (FIG. 4G). It looks like a four pointed star with the origin of the domain (stem/loop 48) and stem/loops 52, 57, and 58 forming the points. The most extensive contacts of domain III are with domain II, but it also interacts with domains I, IV and VI. Unlike all the other domains, domain III hardly interacts with domain V at all; the sole contact is a single van der Waals contact involving a single base from each domain.

Figure 4H:
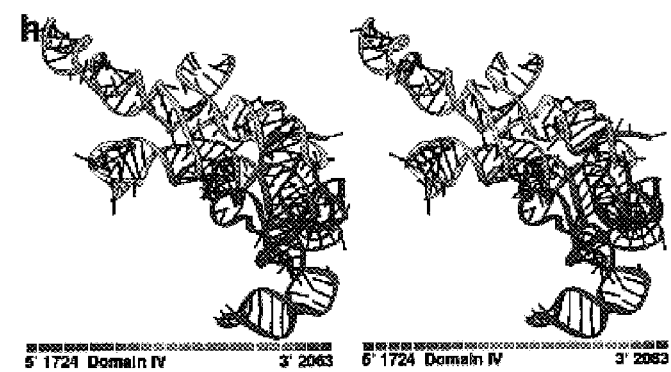

Domain IV accounts for most of the interface surface of the 50S subunit that contacts the 30S subunit (FIG. 4H). It forms a large diagonal patch of flat surface on that side of the subunit, and connects to domains III and V in the back of the particle. Helices 67-71 are the most prominent feature of domain IV, and form the front rim of the active site cleft, which is clearly visible at low resolution (FIG. 2). This is one of the few regions of the 23S rRNA that is not extensively stabilized by ribosomal proteins. Helix 69 in the middle of this ridge interacts with the long penultimate stem of 16S rRNA in the small ribosomal subunit and could be viewed as a divider separating A-site bound tRNAs from P-site bound tRNAs.

Figure 4I:
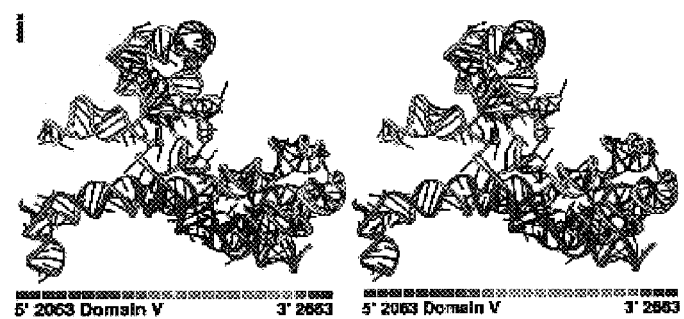
Figure 4J:
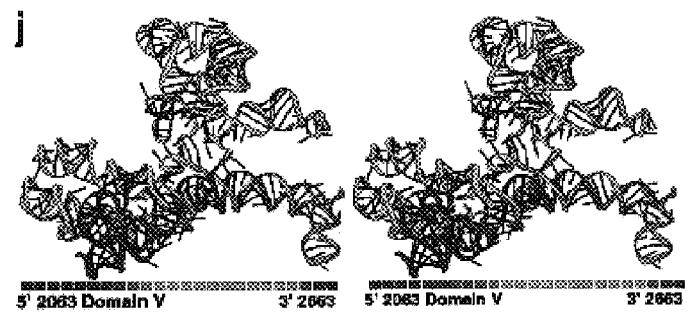

Domain V, which is sandwiched between domains IV and II in the middle of the subunit, is known to be intimately involved in the peptidyl transferase activity of the ribosome. Structurally the domain can be divided into three regions (FIGS. 4I, J). The first starts with helix 75 and ultimately forms the binding site for protein L1. The second, which consists of helices 80-88, forms the bulk of the central protuberance region, and is supported in the back by the 5S rRNA and domain II. The third region, which includes helices 89-93, extends towards domain VI and helps stabilize the elongation factor binding region of the ribosome.

Figure 4K:
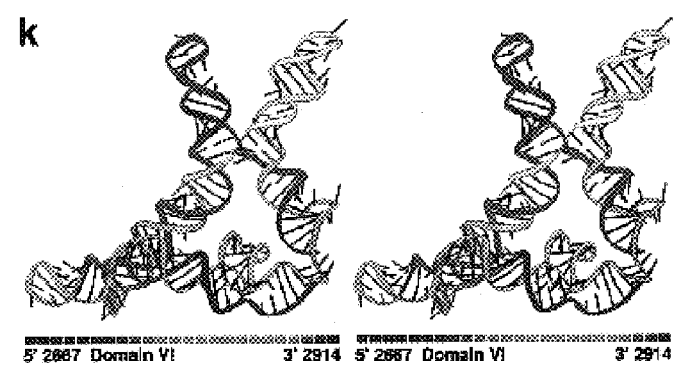

The smallest domain in 23S rRNA, domain VI, which forms a large part of the surface of the subunit immediately below the L7/L12 stalk, resembles a letter X with a horizontal bar at the bottom (FIG. 4K). The most interesting region of this domain is the sarcin-ricin loop (SRL) (stem/loop 95), the structure of which has been extensively studied in isolation (Szewczak et al., 1995). The SRL is essential for factor binding, and ribosomes can be inactivated by the cleavage of single covalent bonds in this loop (Wool et al., 1992). As suggested by nucleotide protection data, the major groove of this loop is exposed to solvent (Moazed et al., 1988), and its conformation is stabilized by proteins and through interaction with domain V that involves two bases on the minor grove side. The nucleotides involved are A 2699 and G 2700 in domain VI, and A 2566 and G 2567 in domain V.

Figure 4L:
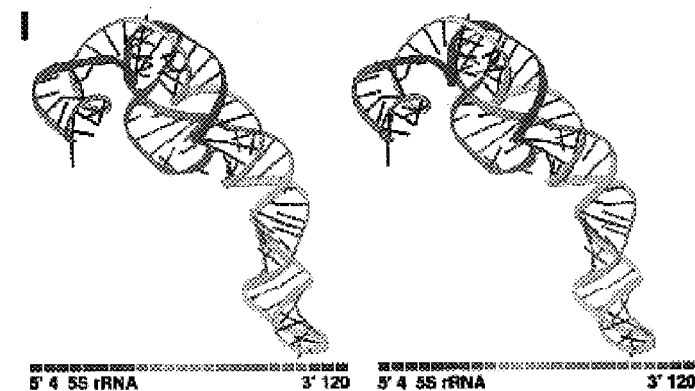

5S ribosomal RNA, which is effectively the seventh RNA domain in the subunit, consists of three stems radiating out from a common junction called loop A (FIG. 4D). In contrast to what is seen in the crystal structure of fragment 1 from *E. coli* 5S rRNA (Correll et al., 1997), the helix 2/3 arm of the molecule stacks on its helix 4/5 arm, not helix 1 (FIG. 4L). This arrangement results from a contorted conformation of loop A residues that involves two stacked base triples. Indeed, from the secondary structure point of view, the loop A-helix 2,3 arm of 5S rRNA is quite remarkable. Nowhere else in the subunit is there a higher concentration of unusual pairings and of convoluted RNA secondary structure.

6. Sequence Conservation and Interactions in 23S rRNA

While 23S/28S rRNAs contain many conserved sequences, they also vary substantially in chain length. Shorter 23S/28S rRNAs are distinguished from their longer homologues by the truncation of, or even the elimination of entire stem/loops, and by comparing sequences, one can identify a minimal structure that is shared by all (Gerbi et al., 1995). The expansion sequences in the 23S rRNA of *H. marismortui*, i.e. the sequences it contains that are larger than the minimum, are shown in FIG. 5 in green. They are largely absent from the subunit interface surface of the particle, but they are abundant on its back surface, far from its active sites. This is consistent with low resolution electron microscopic observations suggesting that the region of the large subunit whose structure is most conserved is the surface that interacts with the small subunit (Dube et al., 1998).

There are two classes of conserved sequences in 23S rRNA. One contains residues concentrated in the active site regions of the large subunit. The second class consists of much shorter sequences scattered throughout the particle (FIG. 5; red sequences). The SRL sequence in domain VI and the cluster of conserved residues belonging to domain V that are located at the bottom of the peptidyl transferase cleft are members of the first class. They are conserved because they are essential for substrate binding, factor binding and catalytic activity. Most of the residues in the second class of conserved residues are involved in the inter- and intra-domain interactions that stabilize the tertiary structure of 23S rRNA. Adenosines are disproportionately represented in this class. The predominance of A's among the conserved residues in rRNAs has been pointed out in the past (Ware et al., 1983). A manuscript is in preparation that describes these A-dependent interactions at greater length.

In addition to its reliance on A-dependent motifs, the tertiary structure of the domains of 23S rRNA and their relative positions are stabilized by familiar tertiary structure elements like RNA zippers and tetraloop/tetraloop receptor motifs (Moore et al. 1999), and in many places, base pairs and triples stabilize the interactions of sequences belonging to different components of the secondary structure of 23S rRNA.

Interestingly, 5S rRNA and 23S rRNA do not interact extensively with each other. The few RNA/RNA interactions there are involve the backbones of the helix 4/5 arm of 5S rRNA and the backbone of helix 38 of 23S rRNA. Most of the free energy and all of the specificity of 5S rRNA binding to the large ribosomal subunit appears to depend on its extensive interactions with proteins that act as modeling clay sticking it to the rest of ribosome.

7. Proteins in the 50S Ribosomal Subunit

We have determined the structures of 27 proteins found in the large ribosomal subunit of *H. marismortui* (Table 2). Twenty-one of these protein structures have not been previously established for any homologues, and the structures of the six that do have homologues of known structure have been rebuilt into the electron density map using their *H. marismortui* sequences. In addition, there are structures available for homologues of *H. marismortui* L1, L11 and L12, which cannot be visualized in the 2.4 Å resolution electron density map. Only the structure of L10 is still unknown among the 31 proteins known to be present.

Not every one of these structures is complete. For example, an entire domain of L5 is missing from the electron density, presumably because of disorder. L32e is also noteworthy in this regard. About 20 residues from its N-terminus are not seen in the electron density map, and the electron density map suggests that its C-terminal residue is covalently bound to the most N-terminal of its visible residues.

Of the 30 large subunit ribosomal proteins whose structures are known, 17 are globular proteins, similar in character to thousands whose structures are in the Protein Data Bank (Table 2). The remaining 13 proteins either have globular bodies with extensions protruding from them ("glb+ext") or are entirely extended ("ext"). Their extensions often lack obvious tertiary structure and in many regions are devoid of secondary structure as well (FIG. 6). These extensions may explain why many ribosomal proteins have resisted crystallization in isolation. The exceptions that prove the rule are L2 and L4, both of which are proteins belonging to the "glb+ext" class. Protein L2 was crystallized and its structure solved only after its extensions had been removed (Nakagawa et al., 1999), and one of the two regions of L4 that are extended in the ribosome is disordered in the crystal structure of intact L4 (Wahl et al., 2000).

Except for proteins L1, L7, L10 and L11, which form the tips of the two lateral protuberances, the proteins of the 50S subunit do not extend significantly beyond the envelope defined by the RNA (FIG. 7). Their globular domains are found largely on the particle's exterior, often nestled in the gaps and crevices formed by the folding of the RNA. Thus, unlike the proteins in spherical viruses, the proteins of the large ribosomal subunit do not form a shell around the nucleic acid with which they associate, and unlike the proteins in nucleosomes, they do not become surrounded by nucleic acid either. Instead, the proteins act like mortar filling the gaps and cracks between "RNA bricks".

The distribution of proteins on the subunit surface is nearly uniform, except for the active site cleft and the flat surface that interacts with the 30S subunit. In the crown view the proteins lie around at the periphery of the subunit (FIG. 7A), but when viewed from the side opposite the 30S subunit binding site (the "back side"), they appear to form an almost uniform lattice over its entire surface (FIG. 7B). Similarly, the bottom surface of the subunit, which includes the exit of polypeptide tunnel, is studded with proteins (FIG. 7C). Indeed the 5 proteins that surround the tunnel exit may play a role in protein secretion since they are part of the surface that faces the membrane and the translocon when membrane and secreted proteins are being synthesized.

Although FIG. 7 shows protein chains disappearing into the ribosome interior, the degree to which proteins penetrate the body of the particle can only be fully appreciated when the RNA is stripped away. The interior of the particle is not protein-free, but it is protein-poor compared to the surface of the particle. Extended tentacles of polypeptide, many of which emanate from globular domains on the surface, penetrate into the interior, filling the gaps between neighboring elements of RNA secondary structure (FIG. 8E). The bizarre structures of these extensions are explained by their interactions with RNA. A detailed analysis of these proteins and their interactions with RNA will be presented elsewhere.

Although extended, non-globular structures are rare in the protein data base, they are not unknown. Extended protein termini often form inter-protein contacts, e.g. in viral capsids, presumably adopting fixed structures only upon capsid formation. The basic "tails" of histones may behave the same way when nucleosomes form. The N-terminal sequences of capsid proteins are often positively charged, and in virus crystal structures, the electron density for these sequences often disappears into the interior of the virus where these sequences presumably interact with asymmetrically arranged nucleic acid. The interactions observed in the ribosome could be useful models for these viral interactions.

Figure 8A:
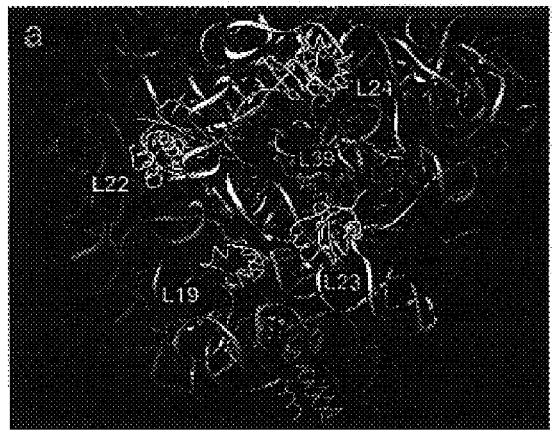
Figure 8B:
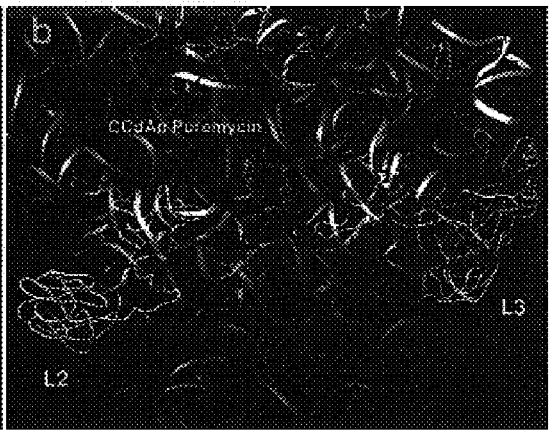

The interactions of extended polypeptides and RNA in the large subunit, which stabilizes its massive nucleic acid structure, result in a tangle of RNA and protein in the center of the subunit (FIG. 8A, B). It is hard to imagine such an object assembling from its components efficiently in anything other than a highly ordered manner. Chaperones may well be required to prevent the aggregation of the extended regions of these proteins, which are likely to be disordered outside the context provided by rRNA, and to manage the folding of rRNA.

8. Protein and RNA Interactions

Because protein permeates the large subunit to a surprising degree, there are only a few segments of the 23S rRNA that do not interact with protein at all. 1157 of the 2923 nucleotides in 23S rRNA make at least van der Waals contact with protein (FIG. 8D), and there are only 10 sequences longer than 20 nucleotides in which no nucleotide contacts protein. The longest such sequence contains 47 nucleotides, and is the part of domain IV that forms the ridge of the active site cleft.

The extent of the interactions between RNA and protein that occur when the large subunit assembles can estimated quantitatively. Using the Richards algorithm (Lee et al., 1971) and a 1.7 Å radius probe to compute accessible surface areas, it can be shown that 180,000 Å$^2$ of surface becomes buried when the subunit forms from its isolated, but fully structured components. This is about half their total surface area. The average is about 6,000 Å$^2$ per protein. While this is an enormous amount compared to the surface buried when most protein oligomers form, it should be recognized that ribosome assembly must be accompanied by a large loss in conformational entropy that does not occur when most proteins oligomerize. The extended protein termini and loops of the ribosomal proteins are almost certainly flexible in isolation, and in the absence of protein, the RNA is probably quite flexible as well. Thus the burial of a large amount of surface area may be required to provide the energy necessary to fix of the structures of these molecules.

Figure 8C:
Figure 8D:
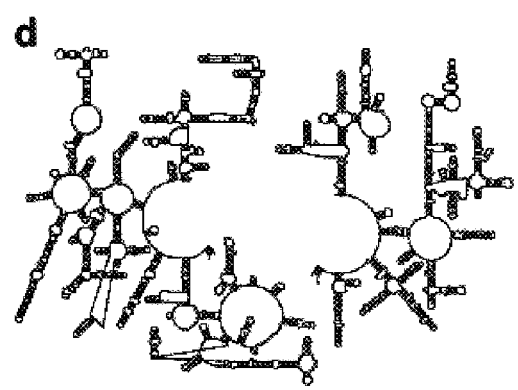
Figure 8E:
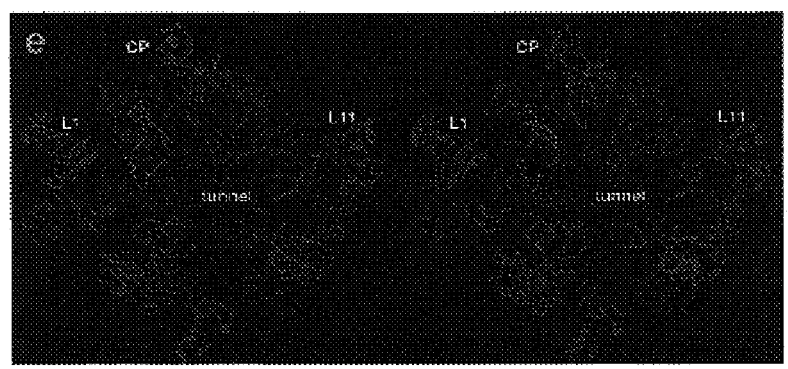

All of the proteins in the particle except L12, interact directly with RNA and all but 7 of the remaining 30 proteins interact with two rRNA domains or more (Table 2). The "champion" in this regard is L22, which is the only protein that interacts with RNA sequences belonging to all 6 domains of the 23S rRNA (FIG. 8C). The protein-mediated interactions between 5S rRNA and 23S rRNA are particularly extensive. Protein L18 attaches helix 1 and helix 2/3 of 5S rRNA to helix 87 of 23S rRNA. Protein L31e mediates an interaction between the same part of 5S rRNA and domains II and V. Loop C is linked to domain V by protein L5 and loop D is attached to domains II and V by protein L10e. Whatever else they may do, it is evident that an important function of these proteins is stabilization of the relative orientations of adjacent RNA domains. Several also help secure the tertiary structures of the domains with which they interact.

Since most ribosomal proteins interact with many RNA sequences and the number of proteins greatly exceeds the number of RNA domains, it can hardly come as a surprise that every rRNA domain interacts with multiple proteins (Table 2). Domain 5, for example, interacts with 13 proteins, some intimately and a few in passing.

It is clear that the oligonucleotide binding experiments long relied on for information about the RNA binding properties of ribosomal proteins have underestimated their potential for interacting with RNA. The high-affinity, RNA binding site identified on a protein by such an experiment may indeed be important for ribosome assembly, but its many, weaker interactions with other sequences are likely to be missed, and they too may be vital for ribosome function. Most ribosomal proteins crosslink RNA and crosslinking is impossible without multiple interactions. Similar considerations may apply to proteins that are components of other ribonucleoproteins such as the sliceosome.

Of the seven proteins that interact with only one domain, three (L1, L10, L11) participate directly in the protein synthesis process. Rather than being included in the ribosome to ensure that the RNA adopts the proper conformation, it seems more appropriate to view the RNA as being structured to ensure their correct placement. Another three (L24, L29, L18e) interact with several secondary structure elements within the domains to which they bind, and presumably function to stabilize the tertiary structures of their domains. The last of the single RNA domain proteins, L7ae, is puzzling. On the one hand, it cannot function as an RNA stabilizing protein because it interacts with only a single, short sequence in domain I, and on the other hand, it is far from the important functional sites in the subunit, the peptidyl transferase site and factor binding site. It is quite close to L1, however, which appears to be important for E-site function (Agrawal et al., 1999), and maybe it is involved in that activity.

While many ribosomal proteins interact primarily with RNA, a few interact significantly with other proteins. The most striking structure generated by protein-protein interactions is the protein cluster composed of L3, L6, L14, L19 and L24e that is found close to the factor binding site. The protein surface they provide may be important for factor interactions.

The structure presented above illuminates both the strengths and weaknesses of approaches to complex assemblies that depend on determining the structures of components in isolation. The structures of the globular domains of homologues of the proteins in large ribosomal subunit from *H. marismortui* are largely the same as those of the corresponding domains in the intact subunit, though adjustments in domain positions are sometimes required. Consequently, these structures were very useful for locating proteins and interpreting lower resolution electron density maps. However, for obvious reasons, the structures of the extended tails and loops of ribosomal proteins cannot be determined in the absence of the RNAs that give them structure, and the feasibility of strategies that depend on producing low molecular weight RNA-protein complexes that have all the RNA contacts required to fix the structures of such proteins seems remote. RNA is also a problem. While the sarcin/ricin loop has much the same structure in isolation as it does in the ribosome, the structure of 5S rRNA in isolation differs in some respects from what is seen in the ribosome, and the structure of the isolated P-loop (Puglisi et al., 1997) does not-resemblance to the structure of the P-loop in the ribosome at all. Clearly a "structural genomics" approach to the ribosome, which would have entailed determining the structures of all its proteins and all possible rRNA fragments, would not have worked. It may not be successful for other macromolecular assemblies either.

B. The Structural Basis of Ribosome Activity in Peptide Bond Synthesis

The present invention is also based on the crystals of *Haloarcula marismortui* 50S ribosomal subunit complexed either with the Yarus transition state analogue, CCdA-p-Puro, or with a mini-helix analogue of an aminoacyl-tRNA. The present invention provides the structures of both complexes. The atomic coordinates of the structure of both complexes were deposited on Jul. 26, 2000, at Research Collaboratory for Structural Bioinformatics (RCSB) Protein Data Bank (PDB) (Berman et al., 2000, Nucleic Acid Research, 28, 235-242; www.rcsb.org/pdb/) with accession numbers PDB ID: 1FFZ (50S ribosome/CCdA-p-Puro complex) and PDB ID: 1FG0 (50S ribosome/aa-tRNA analogue).

As discussed below, the complete atomic structures of the large ribosomal subunit and its complexes with two substrate analogues show that the ribosome is a ribozyme. The complete atomic structures also provide information regarding the catalytic properties of its all-RNA active site. Both substrate analogues are contacted exclusively by conserved rRNA residues from domain V of 23S rRNA; there are no protein side-chains closer than about 18 Å to the peptide bond being synthesized. The mechanism of peptide bond synthesis appears to resemble the reverse of the deacylation step in serine proteases, with the base of A2486 (A2451) in *E. coli* playing the same general base role as His57 in chymotrypsin. The unusual pKa that A2486 must possess to perform this function probably derives from its hydrogen bonding to G2482 (G2447) which interacts with a buried phosphate that could stabilize the unusual tautomers of two bases which is required for catalysis. The polypeptide exit tunnel is largely formed by RNA but has significant contributions from proteins L22, L39 and L4 and its exit is encircled by proteins L19, L22, L23a, L24 and L29.

The CCdA from the Yarus analogue binds to the so-called P-loop (Moazed, et al., 1989), and hence must be in the P-site. Only the terminal-CCA of the aa-tRNA analogue is visible, but since it interacts appropriately with the A-loop (Kim et al., 1999), it must be in the A-site. The puromycin group occupies the same location in both structures, and there are no proteins near that site. Hence, the catalytic activity of the active site must depend entirely on RNA. The N3 of A2486 (*E. coli* A2451) is the titratable group nearest to the peptide bond being synthesized and is likely functioning as a general base to facilitate the nucleophilic attack by the α-amino group of the A-site substrate. In order to function in this capacity, the pKa of this base has to be roughly 5 units higher than normal.

1. Structures of Substrate Analogue Complexes

In order to establish how substrates interact at the A-site and P-site of the large subunit, two substrate analogues were used. One of the analogues, which was designed to mimic the acceptor stem of an aa-tRNA and bind to the A-site, was a 12 base-pair RNA hairpin with an aminoacylated, four-nucleotide extension on its 3' end (FIG. 9). The sequence used was that of the tRNA tyr acceptor stem and it is terminated with puromycin, which itself is an analogue of tyrosyl-A76. The second analogue used was the Yarus transition state analogue, CCdA-p-puromycin. As in the case of the A-site substrate analogue, the puromycin of the Yarus inhibitor is expected to bind at the A-site, while its CCdA moiety should bind at the P-site.

The positions of the Yarus inhibitor and the tRNA acceptor stem analogue were determined by soaking these molecules into crystals of the *Haloarcula marismortui* 50S ribosomal subunit, measuring diffraction data to 3.2 Å resolution and calculating difference electron density maps (Welch et al., 1997). Maps of the complexes were also calculated using 2 Fo(complexed)-Fo(uncomplexed) as coefficients, to examine the shifts in the positions of ribosome residues that occur when these analogues bind (FIG. 10B, Table 3).

TABLE 3

Statistics for Data Collection and Scaling.

| Crystal | Native A | Native B | CCdAp-Puro | Mini-helix |
|---|---|---|---|---|
| Soak time (hours) | — | — | 24 | 24 |
| Soak concentration (μM) | — | — | 100 | 100 |
| Wavelength (Å) | 1.0 | 1.0 | 1.0 | 1.0 |
| Observations | 1,571,171 | 1,344,877 | 2,590,726 | 2,712,813 |
| Unique | 284,533 | 369,167 | 367,284 | 447,121 |
| Redundancy | 5.5 | 3.6 | 7.0 | 6.0 |
| Resolution limits (Å) | 70.0-3.2 | 70.0-3.0 | 70.0-3.0 | 70.0-2.8 |
| (High-resolution bin)* | (3.26-3.20) | (3.05-3.00) | (3.23-3.17) | (3.08-3.02) |
| Completeness | 94.1 (96.0) | 98.9 (99.3) | 98.6 (99.9) | 99.6 (100) |
| I/σI | 14.6 (4.0) | 10.8 (3.1) | 11.0 (2.8) | 10.7 (2.9) |
| $R_{merge}$† | 10.2 (40) | 11.5 (38) | 18.8 (84) | 14.3 (72) |
| $R_{iso}$ Native A‡ | — | — | 6.8 (20.8) | 14.4 (25.2) |
| $R_{iso}$ Native B‡ | — | — | 12.6 (27.4) | 17.5 (31.0) |

*Statistics in parenthesis are calculated for the high-resolution bin used in map calculations, which, as indicated was sometimes lower in resolution than the high-resolution bin used in data reduction.
†$R_{merge}$: $\Sigma\Sigma_i |I_{(h)} - I_{(h)i}|/\Sigma\Sigma I_{(h)i}$ where $I_{(h)}$ is the mean intensity after reflection.
‡$R_{iso}$: $\Sigma |F_{PH} - F_P|/\Sigma F_{PH}$, where $F_{PH}$ and $F_P$ are the soaked and the native crystal structure factor amplitudes respectively.

A model for the entire Yarus inhibitor could be fitted into the difference density (FIG. 10A), and the electron density map of the complex shows the N3 of A2486 (2451) within hydrogen bonding distance of a non-bridging oxygen of the phosphoramide (FIG. 10B). The inhibitor's two C's, which correspond to C74 and C75 of peptidyl-tRNA, are Watson-Crick base-paired with G2285 (2252) and G2284 (2251) in the P-loop, respectively (FIG. 11A). The C74-G2285 (2252) interaction was predicted by the results of Noller and coworkers (Noller et al., 1992). The dA, which corresponds to A76 of a tRNA in the P-site, is not base-paired, but rather stacks on the ribose of A2486 and hydrogen bonds to the 2' OH of nucleotide A2485 (FIG. 12B).

Only the CC-puromycin moiety of the mini-helix acceptor stem analogue showed ordered electron density in its difference electron density map (FIG. 10C). The C75 of the acceptor stem CCA is Watson-Crick base-paired with G2588 (2553) of the A-loop, whereas the C74 is more disordered and not base-paired but appears to stack on a ribosome base. The dimethyl A of the A-site inhibitor puromycin is positioned identically to the dimethyl A of the Yarus inhibitor. Further, the dimethyl A of puromycin, which is the A76 equivalent of an A-site tRNA, interacts with the A-loop in much the same way that the A76 from the P-site CCA interacts with the P-loop (FIG. 11B).

The most notable of the several conformational changes in the ribosome induced by the binding of the transition state analogue is the ordering of base A2637 (2602), which is disordered in the unliganded enzyme (FIG. 11B). It becomes positioned between the CCA bound at the A-site and the CCA bound at the P-site. The base of U2620 (2585) also moves so that it can make a hydrogen bond with the 2' hydroxyl of the ribose of A76 in the A-site, and U2619 and G2618 shift to allow the A76 to be positioned. Smaller shifts in positions are observed in the positions of A2486, whose N3 is near to the non-bridging oxygen of the phosphate, and one of the G residues with which it interacts, G2102 (2482).

2. Location and Chemical Composition of the Peptidyl Transferase Site

The inhibitors are bound to a site made entirely of 23S rRNA with no proteins nearby, proving that the ribosome is a ribozyme. Both the Yarus inhibitor and the A-site analogue of aa-tRNA bind to the large subunit at the bottom of a large and deep cleft at the entrance to the 100 Å long polypeptide exit tunnel that runs through to the back of the subunit (FIG. 12). This site is surrounded by nucleotides belonging to the central loop of 23S RNA domain V, the "peptidyl transferase loop". Nucleotides from the single stranded portions of this loop make the closest approach to the phosphate that mimics the tetrahedral carbon intermediate. In general, the helices that extend from the peptidyl transferase loop in 2 secondary structure diagrams of 23S rRNA also extend away from the active site in the tertiary structure (FIG. 13). Although there are 13 proteins that interact with domain V (FIG. 14A), there are no globular proteins in the vicinity of the inhibitor. The closest polypeptides are the non-globular extensions of several proteins (L2, L3, L4, L10e) that penetrate deeply into domain V and approach the active site (FIG. 14B). These extensions fill many of the voids between the RNA helices of domain V, neutralize phosphate backbone charge, and presumably stabilize the structure of the domain and its association with other RNA regions. However, none of their side chain atoms is closer than about 18 Å to the phosphorus of the inhibitor's phosphate group, which marks the site where peptide bonds form. Furthermore, the substrate analogue is completely enclosed in an rRNA cavity that is so tightly packed that there is no possibility that an unidentified peptide could be lurking nearby (FIG. 15). Thus, the catalytic entity in the ribosome must be RNA.

Two of the proteins with long termini or loops penetrating the rRNA scaffold of domain V are proteins that could not previously be excluded from involvement in the peptidyl transferase reaction L2 and L3 (Noller, 1991). Noller and colleagues (Noller et al., 1992) found that under conditions which prevent RNA denaturation, extensive digestion of Thermus thermophilus 50S subunits with proteases followed by extraction with phenol and other agents that disrupt protein-RNA interactions did not remove several peptides from the subunit that were less than 10,000 in molecular weight. The structure makes it clear why these protein fragments were particularly resistant to protease treatments. While protease treatment could digest the globular protein domains on the surface of the large subunit, it could not remove the long termini or loops that penetrate deeply in the 23S rRNA because they are sequestered within the rRNA and thus protected from cleavage, independently of the globular domains.

3. Peptidyl Transferase Active Site

The RNA that surrounds the substrate analogues is closely packed, much like the active site region of a protein enzyme and the nucleotides in contact with the inhibitor are greater than 95% conserved in all three kingdoms of life (FIG. 15). Thus, it is clear that the ribosome is a ribozyme, but what gives the RNA its catalytic power?

The residue most likely to be involved in catalysis, presumably as a general base, is A2486, whose N3 is about 3 Å from the phosphoramide oxygen of the Yarus inhibitor that is the analogue of the carbonyl oxygen of a nascent peptide bond and about 4 Å from the amide that corresponds to the amide nitrogen of the peptide bond being synthesized. Ordinarily, the pKa of the N1 of adenosine monophosphate is about 3.5 and that of its N3 is perhaps 2 pH units lower (Saenger, 1984), and in order for A2486 to function as a general base, its pKa would have to be raised to 7 or higher. The crystal structure itself suggests that its pKa is, in fact, quite unusual. The N3 of A2486 can only hydrogen bond to the phosphate oxygen, as observed, if it (or the phosphate oxygen) is protonated. The distance between these two atoms is about 3 Å indicating that a hydrogen bond does, indeed, exist between them. Since the crystal is at pH 5.8, this implies that the pKa of the N3 is greater than 6. Muth and Strobel have measured the pKa of the corresponding A in *E. coli* 23S RNA by examining its dimethyl sulphate reactivity as a function of pH and have concluded that it is 7.6, though they cannot be sure from their experiments whether it is the N3 or Ni whose pKa they have measured (Muth et al., 2000). Because there is no other available, titratable RNA functional group closer than X Å to the nascent peptide bond, there is not other group available to function as a general base.

There are several features of environment of A2486 (2451) that might affect its pKa. The pKa of the N3 of A2486 (2451) may be increased significantly in part by a charge relay mechanism, analogous to that which occurs in the active site of the serine proteases, with the buried phosphate of A2485 (2450) performing a similar function as the buried carboxylate of Asp102 of chymotrypsin. The experimental 2.4 Å electron density map unambiguously establishes the hydrogen bonding interactions in this most critical region of the active site (FIG. 16A). The N6 of A2486 interacts with the O6 atoms of G2482 (2447) and G2102 (2061) (FIG. 16B). The N2 of G2482 is also interacting with a non-bridging oxygen of the phosphate group of A2485 (2450) that is among the total of 3 most solvent inaccessible phosphate groups (826, 1497 and 2485) in the large ribosomal subunit for which we do not see any neutralizing counterion in the 2.4 Å resolution map. Weak density that may correspond to a water molecule is hydrogen bonded to the other non-bridging oxygen. A neutralizing counterion is not apparent at this time. The buried phosphate of A2485 could abstract the proton from the exocyclic N2 of G2482 in order to neutralize its energetically unfavorable buried negative charge. This, in turn, would stabilize the otherwise rare imino tautomer of that base. The interaction of an imino of G2482 with A2486 likewise can stabilize the imino tautomer of A2486 that would result in a negative charge on its N3 were it unprotonated (FIG. 16C). In this way, some of the negative electrostatic charge originating on the buried phosphate of A2485 could be relayed to the N3 of A2486, thereby increasing its pKa.

A second feature of the environment of the catalytic site that may affect its stability, tautomeric state and electrostatic charge distribution is a bound monovalent cation. A potassium or a sodium ion is interacting with the O6 of G2482 and G2102 as well as with three other bases. Its identity as a potassium ion is established by its observed continuation and by an independent experiment showing that a rubidium ion can bind to this site. The monovalent ion might also stabilize non-standard tautomers, but its expected influence on the pKa of A2486 is less obvious. Early biochemical experiments have shown the importance of potassium for peptidyl transferase activity (Monro, 1967; Maden et al., 1968) and this binding site could be responsible for that affect.

It may also be the case that stabilization of an imino tautomer by a buried phosphate explains the expected higher pKa of a catalytic cytosine in the active site of the hepatitis delta virus ribozyme (Ferre-D'Amare et al., 1998; Naharo et al., 2000). In this case, a backbone phosphate, whose solvent accessibility is similar to that of A2485 in the ribosome, is observed to hydrogen bond to the N4 of C, and the protonated form of the imino tautomer of that C would neutralize the phosphate, promoting the function of its N3 as a general acid (Naharo et al., 2000).

4. Catalytic Mechanism of Peptide Bond Formation

The proximity of the N3 of A2486 (2451) to the peptide bond being synthesized and the nature of the reaction catalyzed suggest a chemical mechanism of peptide synthesis that is analogous to the reverse of the deacylation step seen in serine proteases during peptide hydrolysis (Blow et al., 1969; Steitz et al., 1982). In that mechanism, the basic form of His57 abstracts a proton from the α-amino group of the peptide product as it attacks the acyl-Ser195. Formation of the tetrahedral carbonyl carbon intermediate is stabilized by interaction of the oxyanion formed with backbone amides (the "oxyanion hole"); His57 shuttles the proton acquired from the α-NH2 to Ser195 as the tetrahedral intermediate breaks down.

We suggest that A2486 (2451) is the analogue of His57 in chymotrypsin and that the peptidyl-tRNA is analogous to acyl-Ser195. Thus, the N3 of A2486, with its greatly elevated pKa, abstracts a proton from the a-amino group of the A-site bound aminoacyl-tRNA facilitating the nucleophilic attack of that amino group on the carbonyl carbon that acylates the 3' OH of the tRNA in the P-site (FIG. 17A). In contrast to the serine proteases, however, the oxyanion of the tetrahedral intermediate is near to the protonated N3 of A2486 (A2451) rather than being proximal to a separate oxyanion binding site. Thus, it could be that the protonated N3 of A2486 stabilizes the formation of the oxyanion by hydrogen bonding to it, as we observe in the Yarus inhibitor complex (FIG. 17B). The N3 of A2486 could then subsequently transfer its proton to the 3' hydroxyl of the P-site bound tRNA, which is liberated as the peptide shifts to the A-site bound tRNA (FIG. 17C).

How is the catalyzed hydrolysis of the peptidyl tRNA in the P-site prevented prior to the delivery of the next appropriate aa-tRNA to the A-site? It appears from this complex that water would not be excluded from access to the peptidyl link to the P-site tRNA if the A-site were vacant. An analogous problem was discussed by Koshland in the 1960s (Koshland, Jr., 1963): he asked why hexokinase does not hydrolyze ATP in the absence of glucose, since water should bind perfectly well to the binding site used by the 6-hydroxyl of glucose. The answer he proposed was induced fit; hexokinase is not catalytically competent until the glucose binds and produces a conformational change that orients substrates and catalytic groups optimally. This is indeed the case (Bennett, Jr. et al., 1978). Similarly, it could be that the catalytic A2486 and/or the peptidyl substrate are not properly oriented or that the binding site for the α-NH2 group is blocked by a reoriented ribosome base in the absence of aa-tRNA in the A-site. We do observe that the base of U2620 is close to A2486 in the ligand free structure, and it may serve as the appropriate plug that prevents spontaneous hydrolysis of peptidyl-tRNA. The structure of an analogue of peptidyl-tRNA bound to the P-site of the large ribosomal subunit will have to be determined in order to answer this question.

Thus, it appears that this RNA enzyme uses the same principles of catalysis as a protein enzyme. First, a large catalytic enhancement is achieved by precisely orienting the two reactants, the αNH2 from the A-site aminoacyl-tRNA and the carbonyl carbon from the P-site peptidyl-tRNA. This is accomplished, in part, by the interactions of the CCA ends of the A-site and P-site tRNAs with the A-loop and P-loop respectively. Secondly, acid-base catalysis and transition state stabilization are achieved by an enzyme functional group (A2486 (2451) in this case) whose chemical properties are altered appropriately by the active site environment. Third, similar chemical principles may be used by RNA and protein enzymes to alter the pKa's of functional groups. A buried carboxylate of Asp102 acting through His57 alters the nucleophilicity of Ser195 in chymotrypsin (Blow et al., 1969). In the ribosome a solvent inaccessible phosphate may act through G2482 (2447) alters the nucleophilicity of the N3 of A2486 (2451). It could be that RNA molecules "learned" how to use the chemical principles of catalysis significantly before protein molecules did.

5. tRNA Binding

While it is not possible to bind tRNA molecules to either the A-or P-sites in these crystals for steric reasons, it is possible to place the A-, P- and E-site tRNA molecules on the large ribosomal subunit in the same relative orientation that Cate et al. observed in their crystallographic study of the *Thermus aquaticus* 70S ribosome (Strobel et al., 2000). The coordinates of the three tRNA molecules in the relative positions seen in the 70S ribosome can be docked on the *Haloarcula marismortui* large ribosomal subunit in a way that avoids steric clashes and places the acceptor stems of the A-site and P-site tRNAs near to the positions of the CCAs we have observed bound to the A-loop and P-loop (FIG. 18). Although Cate et al. (Strobel et al., 2000) modeled nucleotides C74 and C75 in a different conformation in their 7.8 Å ribosome map, the C74 residues from the CCAs in both the A- and P-sites can be connected to residue 72 of the docked A-site and P-site tRNAs through a modeled residue 73, and it appears that the tRNA molecules fit well onto the surface of the subunit. Unexpectedly, this modeling places the E-site, P-site and A-site bound tRNA molecules in close proximity to three ribosomal proteins. Proteins L5 and L10e are near tRNAs in the P-site and A-site. Since both of these proteins also interact with 5S rRNA, this observation raises the possibility that 5S rRNA and some of its associated proteins might help stabilize the positioning of ribosome bound tRNAs and is consistent with the fact that 5S rRNA enhances ribosomal activity, but is not absolutely essential for it (Moore, 1995). Protein L44e appears to interact with the E-site tRNA and may contribute to E-site activity. According to this docking experiment the A-site tRNA interacts with the highly conserved stem-loop 2502-2518 (2467-2483) which together with L10e forms a large concave surface that contacts the tRNA on the T-stem, utilizing the exact same binding site exploited by EF-Tu (Gutell et al., 2000).

Examination of the relationships between the CCAs bound in the A- and P-sites and the tRNAs to which they are connected as well as their interactions with the ribosome also leads to some insights into translocation. Immediately after formation of the new peptide bond and deacylation of the P-site tRNA, the acceptor end of the P-site tRNA is known to move to the E-side and that of the A-site tRNA moves to the P-site (Blobel et al, 1970). The approximate modeling of the 3 tRNA molecules on the large subunit suggests some possible contributions to this process. First, there are two base-pairs between the P-site tRNA and the P-loop and only one between the A-site and the A-loop. Moving from the A to the P site increases base-pairing, though there must be a concomitant attraction of the deacylated P-site tRNA to an E-site. Further, the CCAs bound to the A and P loops are related by 180° rotation, whereas the tRNAs to which they are attached are not. Thus, the relationships of the CCAs to the acceptor stems cannot be the same in both sites and may not be equally stable. If the conformation of the A-site tRNA is less stable, then moving a tRNA from the A to the P site might be energetically favored.

6. Polypeptide Exit Tunnel

It appears very likely from the structure that all nascent polypeptides pass through the exit tunnel before emerging from the ribosome, since there appears to be no other way out. We are now able to address two important questions about the functioning of the polypeptide exit tunnel: (1) Why do nascent proteins not stick to its walls? Teflon has the marvelous property of not sticking to denatured egg proteins, so how has the ribosome achieved a similar non-stick surface for the denatured proteins that must pass through the tunnel? (2) Do proteins fold to any degree in the tunnel giving the ribosome a chaperon-like function?

The length of the tunnel from the site of peptide synthesis to its exit is about 100 Å, broadly consistent with the length of nascent polypeptide that is protected from proteolytic cleavage by the ribosome (Moazed et al., 1989) and the minimum length required for antibody recognition at the exit (Picking et al., 1992). The tunnel is largely straight, except for a bend 20 to 35 Å from the peptidyl transferase center (FIG. 19). Its diameter varies from about 20 Å at its widest to a narrow point of about 10 Å at the very beginning and at a position 28 Å from the tunnel exit with an average diameter of about 15 Å. Since the smallest orifice through which the polypeptide product must pass only barely accommodates the diameter of an α-helix diameter, it seems unlikely that significant protein folding beyond the formation of α-helix could occur within the ribosome.

The majority of the tunnel surface is formed by domains I-V of 23S rRNA, but significant contributions are also made by the non-globular regions of proteins L22, L4 and L39 which not only fill some of the voids in the RNA scaffold, but also form significant portions of the tunnel wall (FIG. 19). The largest protein contributor to the surface of the tunnel is L22 whose long α-hairpin loop lies between RNA segments of domains I through IV and is approximately parallel with the axis of the tunnel. Unlike the other tunnel proteins, protein L39 does not have a globular domain at the surface of the particle and is almost entirely buried in domains I and III underneath protein L23. Interestingly, the nucleotides of 23S rRNA that form the tunnel wall are predominantly from loops in the 23S rRNA secondary structure (FIG. 19). As it progresses through the tunnel from the active site, a nascent polypeptide first encounters domain V followed 20 Å further along by domains II and IV and proteins L4 and L22. The last half of the tunnel is formed by domains I and III and the protein L39e.

Figure 19A:
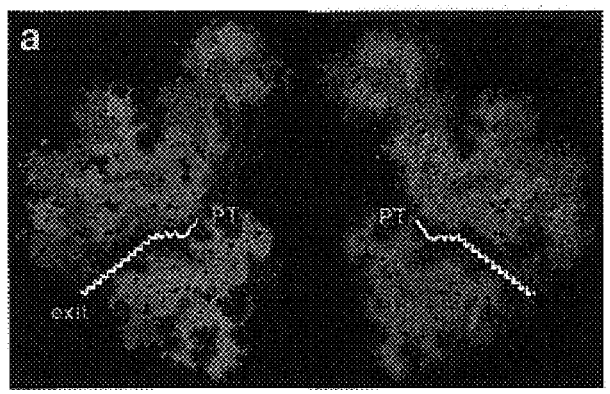
Figure 19B:
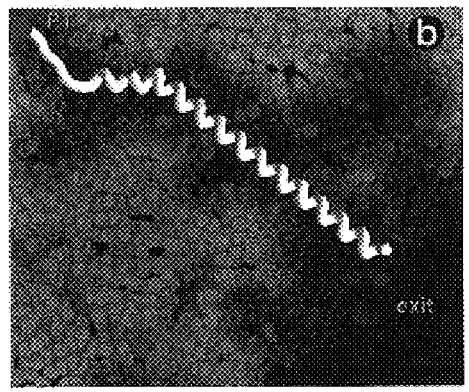
Figure 19C:
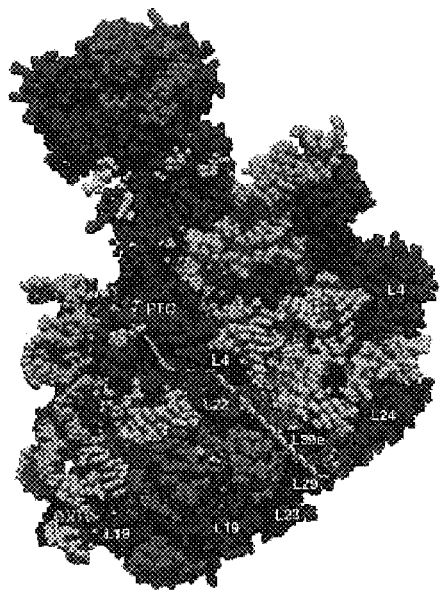
Figure 19D:
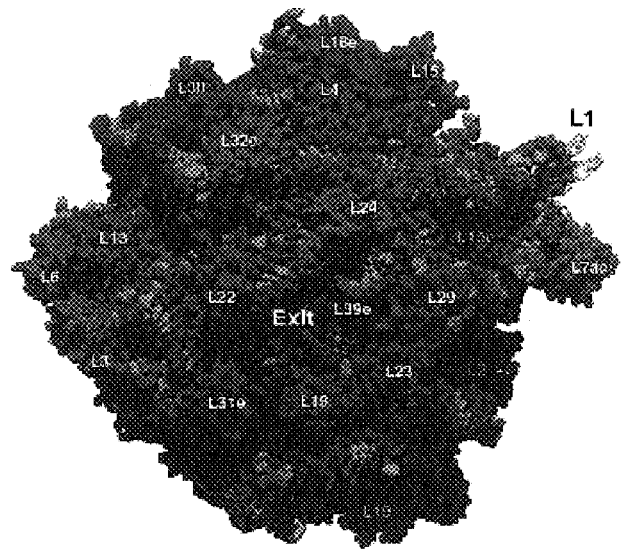
Figure 19E:
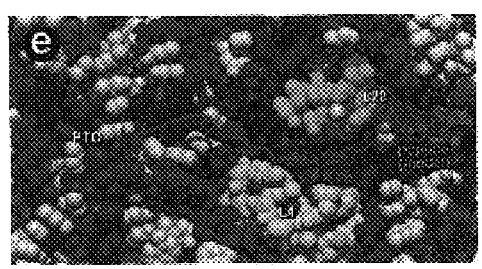
Figure 19F:
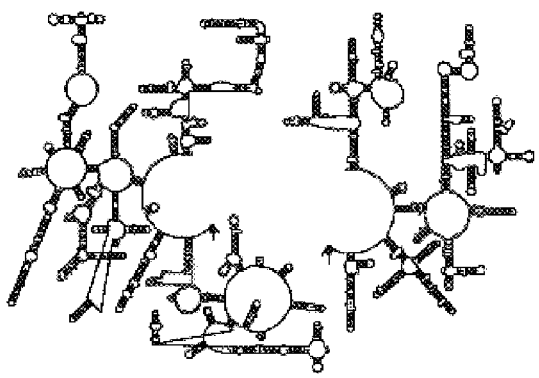

The narrowest part of the tunnel is formed by proteins L22 and L4 which approach the tunnel from opposite sides forming what appears to be a gated opening (FIG. 19C). The function of this constriction, if any, is not obvious. It might be the place where the nature of the nascent chain is sensed and the information transmitted to the surface of the particle, perhaps through L22 or L4. The β-hairpin of L22 at the site of this orifice and the 23S rRNA interacting with it are highly conserved; its globular portion is located adjacent to the tunnel exit on the surface that must face the translocon during protein secretion (FIG. 19).

The "non-stick" character of the tunnel wall must reflect a lack of structural and polarity complementarity to any protein sequence or conformation that it encounters. The tunnel surface is largely hydrophilic and includes exposed hydrogen bonding groups from bases, backbone phosphates and polar protein side-chains (FIG. 19). While there are many hydrophobic groups (sugars, bases, protein side-chains) facing the tunnel as well, there are no patches of hydrophobic surface large enough to form a significant binding site for hydrophobic sequences in the nascent polypeptide. As the tunnel is some 20 Å in diameter and filled with water and the newly synthesized polypeptide is presumably freely mobile, the binding of a peptide to the tunnel wall would result in a large loss of entropy that would have to be compensated for by a large complementary interaction surface that is larger than 700 Å (Chothia et al., 1975). Similarly, while Arg and Lys side-chains from a nascent peptide may indeed interact with the phosphates exposed in the tunnel, the degree of structural complementarity and the net binding energy obtained after displacing bound counterions must be too small to overcome the large unfavorable entropy of immobilization that would result from peptide binding. Thus, although the ribosome tunnel is made primarily of RNA, the nature of its surface is reminiscent of the interior surface of the chaperonin, GroEl (Xu et al., 1998) in its non-binding conformation. Only in the conformation that exposes a large hydrophobic surface does GroEL bind a denatured protein.

There are six proteins (L19, L22, L23, L24, L29 and L31e) located at the exit from the tunnel, facing the translocon onto which the ribosome docks during protein secretion. There is good evidence that the ribosome binds to the translocon even after extensive digestion of its protein by protease implying that interaction between the translocon and the ribosome is mediated by RNA (Rapoport et al., 2000). The proximity of these proteins to the translocon, however, leads us to wonder what role, if any, they might play in the protein secretion process. Recent data from the Dobberstein laboratory shows that the N-terminal domain of SRP54, the G-protein from the signal recognition particle involved in signal peptide binding, can be crosslinked to ribosomal proteins L23 and L29 (Dobberstein). These two proteins are adjacent to each other and at the tunnel exit (FIG. 19).

7. Evolution

In vitro evolution of RNA oligonucleotides has produced small RNA molecules that can bind molecules like the Yarus inhibitor effectively or catalyze the peptidyl transfer reaction (Zaug et al., 1998; Welch et al., 1997). The sequence and secondary structure of one of these selected RNAs is reminiscent of the peptidyl transferase loop in domain V of 23S rRNA (Zhaug et al., 1998). The most striking similarity is a five nucleotide sequence that is identical to a sequence in domain V that includes the catalytic A2486, G2482 and the buried phosphate of A2485. Remarkably, all of the groups involved in the proposed charge relay system for activating A2486 in the ribosome, are present in the in vitro selected ribozyme. Thus, though the surrounding structural context is likely to be different, it seems plausible that this artificially evolved ribozyme uses the same mechanisms as the ribosome for shifting the pKa of an adenine and likewise uses it as a base for peptide synthesis. The second RNA (Welch et al., 1997) contains a 12 nucleotide loop that includes a 9-base sequence identical to that found in the same region of the peptidyl transferase loop.

The striking similarities between the sequences containing the key catalytic elements found in the peptidyl-transferase active site of the ribosome and sequences of in vitro selected RNAs having related activities make it clear that the appearance of a small RNA domain capable of catalyzing peptidyl transferase was a plausible first step in the evolution of protein synthesis on the ribosome. The first peptides synthesized by this primordial peptide synthesizing enzyme might have been random polymers or copolymers, and it may have functioned with substrates as simple as an aminoacylated CCA. Basic peptides of the types observed to form the non-globular extensions that co-fold with the 23S rRNA might have been among the first peptides synthesized that were functionally useful. Such peptides could have enhanced the stability of the protoribosome and other early ribozymes as the more sophisticated peptides of the present day ribosome appear to do. The evolution of this simple peptide synthesizing domain into a ribonucleoprotein many times larger and capable of messenger directed synthesis required many additional steps that are not yet obvious.

C. Experimental Techniques which Exploit X-Ray Diffraction Data

Based on the X-ray diffraction pattern obtained from the assemblage of the molecules or atoms in a crystalline solid, the electron density of that solid may be reconstructed using tools well known to those skilled in the art of crystallography and X-ray diffraction techniques. Additional phase information extracted either from the diffraction data and available in the published literature and/or from supplementing experiments may then used to complete the reconstruction.

For basic concepts and procedures of collecting, analyzing, and utilizing X-ray diffraction data for the construction of electron densities see, for example, Campbell et al., 1984, Biological Spectroscopy, The Benjamin/Cummings Publishing Co., Inc., Menlo Park, Calif.; Cantor et al., 1980, Biophysical Chemistry, Part II: Techniques for the study of biological structure and function, W. H. Freeman and Co., San Francisco, Calif.; A. T. Brunger, 1993, X-Flor Version 3.1: A system for X-ray crystallography and NMR, Yale Univ. Pr., New Haven, Conn.; M. M. Woolfson, 1997, An Introduction to X-ray Crystallography, Cambridge Univ. Pr., Cambridge, UK; J. Drenth, 1999, Principles of Protein X-ray Crystallography (Springer Advanced Texts in Chemistry), Springer Verlag; Berlin; Tsirelson et al., 1996, Electron Density and Bonding in Crystals: Principles, Theory and X-ray Diffraction Experiments in Solid State Physics and Chemistry, Inst. of Physics Pub.; U.S. Pat. Nos. 5,942,428; 6,037,117; 5,200,910 and 5,365,456 ("Method for Modeling the Electron Density of a Crystal"), each of which is specifically and totally incorporated by reference herein.

As explained below, a molecular model may then progressively be built using the experimental electron density information and further refined against the data resulting in an accurate molecular structure of the solid.

D. Methods of Using the Atomic Coordinates of the 50S Ribosomal Subunit to Identify and Design Ligands of Interest Three-dimensional modeling is performed using the experimentally determined coordinates derived from these x-ray diffraction patterns, wherein such modeling includes, but is not limited to, drawing pictures of the actual structures, building physical models of the actual structures, and determining the structures of related ribosomes, ribosomal subunits and ribosome/ligand and ribosomal subunit/ligand complexes using the known coordinates. The coordinates are entered into one or more computer programs for molecular modeling, as known in the art. Such molecular modeling can utilize known x-ray diffraction molecular modeling algorithms or molecular modeling software to generate atomic coordinates corresponding to the three-dimensional structure of the large ribosomal subunit alone or the large subunit component of the full ribosome.

Molecular modeling involves the use of computers to build realistic models of molecules that are identifiably related in sequence to the known crystal structure. It also involves modeling new smaller molecule ligands bound to the large subunit starting with the structures of complexes with known ligands. The methods utilized in molecular modeling range from molecular graphics (i.e., 3D representations) to computational chemistry (i.e., calculations of the physical and chemical properties) to make predictions about the binding of ligands or activities of ligands; to design new ligands; and to predict novel molecules, including ligands such as drugs, for chemical synthesis.

One approach to rational drug design is to search for known molecular structures that might bind to an active site. Using molecular modeling, rational drug design programs can look at a range of different molecular structures of drugs that may fit into the active site of an enzyme, and by moving them on the computer screen it can be decided which structures actually fit the site well (William Bains, Biotechnology from A to Z, second edition, 1998, Oxford University Press, page 259).

For basic information on molecular modeling, see, for example, M. Schlecht, Molecular Modeling on the PC, 1998, John Wiley & Sons; Gans et al., Fundamental Principals of Molecular Modeling, 1996, Plenum Pub. Corp.; N. C. Cohen (editor), Guidebook on Molecular Modeling in Drug Design, 1996, Academic Press; and W. B. Smith, Introduction to Theoretical Organic Chemistry and Molecular Modeling, 1996. U.S. patents which provide detailed information on molecular modeling include U.S. Pat. Nos. 6,093,573; 6,080,576; 6,075,014; 6,075,123; 6,071,700; 5,994,503; 5,612,894; 5,583,973; 5,030,103; 4,906,122; and 4,812,12, each of which are incorporated by reference in their entirety.

An alternative but related approach starts with the known structure of a complex with a small molecule ligand and models modifications of that small molecule in an effort to make additional favorable interactions with a ribosome or ribosomal subunit.

The present invention permits the use of molecular and computer modeling techniques to design and select novel ligands, such as antibiotics or other therapeutic agents, that interact with ribosomes and ribosomal subunits. Such antibiotics and other types of therapeutic agents include, but are not limited to, antifungals, antivirals, antibacterials, insecticides, herbicides, miticides, rodentcides, etc.

The invention enables the use of atomic coordinates deposited at the RCSB Protein Data Bank with the accession numbers PDB ID: 1FFK, PDB ID: 1FFZ, and PDB ID: 1FG0 for the 50S ribosomal subunit, 50S ribosomal subunit/CCdA-p-Puro complex 50S ribosomal subunit/aa-tRNA analogue complex, respectively, to design ligands that interact with the large ribosomal subunit and affect protein synthesis. For example, this invention enables the design of ligands that act as competitive inhibitors of protein synthesis by binding to, all or a portion of, the active sites, or other regions of the large ribosomal subunit.

This invention also enables the design of compounds that act as uncompetitive inhibitors of protein synthesis. These inhibitors may bind to, all or a portion of, the active sites or other regions of the large ribosomal subunit already bound to its substrate and may be more potent and less non-specific than known competitive inhibitors that compete for large ribosomal subunit active sites or for binding to large ribosomal subunit. Similarly, non-competitive inhibitors that bind to and inhibit protein synthesis whether or not it is bound to another chemical entity may be designed using the atomic coordinates of the large ribosomal subunits or complexes comprising large ribosomal subunit of this invention. Alternatively, the atomic coordinates provided by the present invention are useful in designing improved analogues of known protein synthesis inhibitors or to design novel classes of inhibitors based on the atomic structures and coordinates of the crystals of the 50S ribosomal subunit/CCdA-p-Puro complex and the 50S ribosomal subunit/aa-tRNA analogue complex. This provides a novel route for designing inhibitors of protein synthesis with both high specificity, stability and other drug-like qualities (Lipinski et al., 1997, Adv. Drug Deliv. Rev., 23:3).

The atomic coordinates of the present invention also enables probing a crystal of a ribosome or ribosomal subunit with molecules composed of a variety of different chemical features to determine optimal sites for interaction between candidate inhibitors and/or activators and the ribosome or ribosomal subunit. For example, high resolution X-ray diffraction data collected from crystals saturated with solvent allows the determination of where each type of solvent molecule sticks. Small molecules that bind to those sites can then be designed and synthesized and tested for their inhibitory activity (Travis, J., Science, 262, p. 1374 (1993)).

Moreover, the present invention enables screening computationally small molecule databases and libraries for chemical entities, agents, ligands, or compounds that can bind in whole, or in part, to ribosomes and ribosomal subunits, more preferably to large ribosomal subunits, and even more preferably to 50S ribosomal subunits. In this screening, the quality of fit of such entities or compounds to the binding site or sites may be judged either by shape complementarity or by estimated interaction energy (Meng, E. C. et al., J. Coma. Chem., 13, pp. 505-524 (1992)).

The design of compounds that bind to or inhibit the functional activity of ribosomes or ribosomal subunits according to this invention generally involves consideration of two factors. First, the compound must be capable of physically and structurally associating with the large ribosomal subunit. Non-covalent molecular interactions important in the association of ribosomes and ribosomal subunits with the compound, include hydrogen bonding, van der Waals and hydrophobic interactions. Second, the compound must be able to assume a conformation that allows it to associate with the ribosomes or ribosomal subunits, more preferably with the large ribosomal subunits, and even more preferably with the 50S ribosomal subunit. Although certain portions of the compound will not directly participate in this association with ribosomes or ribosomal subunits, those portions may still influence the overall conformation of the molecule. This, in turn, may have a significant impact on binding affinities, therapeutic efficacy, drug-like qualities and potency. Such conformational requirements include the overall three-dimensional structure and orientation of the chemical entity or compound in relation to all or a portion of the active site or other region of the ribosomes or ribosomal subunits, or the spacing between functional groups of a compound comprising several chemical entities that directly interact with the ribosomes or ribosomal subunits, more preferably with the large ribosomal subunits, and even more preferably with the 50S ribosomal subunit.

The potential, predicted, inhibitory or binding effect of a ligand or other compound on ribosomes and ribosomal subunits may be analyzed prior to its actual synthesis and testing by the use of computer modeling techniques. If the theoretical structure of the given compound suggests insufficient interaction and association between it and ribosomes or ribosomal subunits, synthesis and testing of the compound is obviated. However, if computer modeling indicates a strong interaction, the molecule may then be synthesized and tested for its ability to interact with the ribosomes or ribosomal subunits and inhibit protein synthesis. In this manner, synthesis of inoperative compounds may be avoided. In some cases, inactive compounds are synthesized predicted on modeling and then tested to develop a SAR (structure-activity relationship) for compounds interacting with a specific region of the ribosome or ribosomal subunit, more preferably of the large ribosomal subunit, and even more preferably of the 50S ribosomal subunit.

One skilled in the art may use one of several methods to screen chemical entities fragments, compounds, or agents for their ability to associate with ribosomes or ribosomal subunits and more particularly with the individual binding pockets of a ribosomal active site or accessory binding sites. This process may begin by visual inspection of, for example, the active site on the computer screen based on the atomic coordinates of the 50S ribosomal subunit and/or its complexes with two substrate analogues, deposited in the RCSB Protein Data Bank with the accession numbers PDB ID: 1FFK, PDB ID: 1FFZ, or PDB ID: 1FG0. Selected chemical entities, compounds, or agents may then be positioned in a variety of orientations, or docked, within an individual binding pocket of a ribosome or ribosomal subunit, more preferably of a large ribosomal subunit, and even more preferably of a 50S ribosomal subunit. Docking may be accomplished using software such as Quanta and Sybyl, followed by energy minimization and molecular dynamics with standard molecular mechanics forcefields, such as CHARMM and AMBER.

Specialized computer programs may also assist in the process of selecting chemical entities. These include but are not limited to:

1. GRID (Goodford, P. J., "A Computational Procedure for Determining Energetically Favorable Binding Sites on Biologically Important Macromolecules" J. Med. Chem., 28, pp. 849-857 (1985)).

The use of software such as GRID, a program that determines probable interaction sites between probes with various functional group characteristics and the macromolecular surface, is used to analyze the surface sites to determine structures of similar inhibiting proteins or compounds. The GRID calculations, with suitable inhibiting groups on molecules (e.g., protonated primary amines) as the probe, are used to identify potential hotspots around accessible positions at suitable energy contour levels. GRID is available from Oxford University, Oxford, UK.

2. MCSS (Miranker, A. and M. Karplus, "Functionality Maps of Binding Sites: A Multiple Copy Simultaneous Search Method." Proteins: Structure, Function and Genetics, 11, pp. 29-34 (1991)). MCSS is available from Molecular Simulations, Burlington, Mass.

3. AUTODOCK (Goodsell, D. S. and A. J. Olsen, "Automated Docking of Substrates to Proteins by Simulated Annealing" Proteins: Structure. Function, and Genetics, 8, pp. 195-202 (1990)). AUTODOCK is available from Scripps Research Institute, La Jolla, Calif.

4. DOCK (Kuntz, I. D. et al., "A Geometric Approach to Macromolecule-Ligand Interactions" J. Mol. Biol., 161, pp. 269-288 (1982)).

The program DOCK may be used to analyze an active site or ligand binding site and suggest ligands with complementary steric properties. DOCK is available from University of California, San Francisco, Calif.

Once suitable chemical entities, compounds, or agents have been selected, they can be assembled into a single ligand or compound or inhibitor or activator. Assembly may proceed by visual inspection of the relationship of the fragments to each other on the three-dimensional image displayed on a computer screen in relation to the atomic coordinates of the large ribosomal subunit and/or its complexes with analogues. This would be followed by manual model building using software such as Quanta or Sybyl.

Useful programs to aid one of skill in the art in connecting the individual chemical entities, compounds, or agents include but are not limited to:

1. CAVEAT (Bartlett, P. A. et al, "CAVEAT: A Program to Facilitate the Structure-Derived Design of Biologically Active Molecules". In molecular Recognition in Chemical and Biological Problems", Special Pub., Royal Chem. Soc., 78, pp. 82-196 (1989)).

Several methodologies for searching three-dimensional databases to test pharmacophore hypotheses and select compounds for screening are available. These include the program CAVEAT (Bacon et al. J. Mol. Biol., 225: 849-858 (1992)) which uses databases of cyclic compounds which can act as "spacers" to connect any number of chemical fragments already positioned in the active site. This allows one skilled in the art to quickly generate hundreds of possible ways to connect the fragments already known or suspected to be necessary for tight binding. CAVEAT is available from the University of California, Berkeley, Calif.

2. 3D Database systems such as MACCS-3D (MDL Information Systems, San Leandro, Calif.). This area is reviewed in Martin, Y. C., "3D Database Searching in Drug Design", J. Med. Chem., 35, pp. 2145-2154 (1992).

3. HOOK (available from Molecular Simulations, Burlington, Mass.).

Instead of proceeding to build an inhibitor of protein synthesis or an inhibitor of a ribosome or a ribosomal subunit in a step-wise fashion one chemical entity at a time as described above, inhibitory or other ribosomal binding compounds may be designed as a whole or "de novo" using either an empty active site or optionally including some portion(s) of a known inhibitor(s). These methods include:

1. LUDI (Bohm, H.-J., "The Computer Program LUDI: A New Method for the De Novo Design of Enzyme Inhibitors", J. ComR. Aid. Molec. Design, 6, pp. 61-78 (1992)).

The program LUDI can determine a list of interaction sites into which to place both hydrogen bonding and hydrophobic fragments. LUDI then uses a library of approx. 600 linkers to connect up to four different interaction sites into fragments. Then smaller "bridging" groups such as —CH2— and —COO— are used to connect these fragments. For example, for the enzyme DHFR, the placements of key functional groups in the well-known inhibitor methotrexate were reproduced by LUDI. See also, Rotstein and Murcko, J. Med. Chem., 36:1700-1710 (1992). LUDI is available from Biosym Technologies, San Diego, Calif.

2. LEGEND (Nishibata, Y. and A. Itai, Tetrahedron, 47, p. 8985 (1991)). LEGEND is available from Molecular Simulations, Burlington, Mass.

3. LeapFrog (available from Tripos Associates, St. Louis, Mo.).

Other molecular modeling techniques may also be employed in accordance with this invention. See, e.g., Cohen, N. C. et al., "Molecular Modeling Software and Methods for Medicinal Chemistry, J. Med. Chem., 33, pp. 883-894 (1990). See also, Navia, M. A. and M. A. Murcko, "The Use of Structural Information in Drug Design", Current Opinions in Structural Biology, 2, pp. 202-210 (1992).

Once a compound has been designed or selected by the above methods, the affinity with which that compound may bind to the ribosome or ribosomal subunit may be tested and optimized by computational evaluation and/or by testing biological activity after synthesizing the compound. Inhibitors or compounds may interact with the ribosomes or ribosomal subunits in more than one conformation that is similar in overall binding energy. In those cases, the deformation energy of binding is taken to be the difference between the energy of the free compound and the average energy of the conformations observed when the inhibitor binds to the ribosomes or ribosomal subunits, more preferably to the large ribosomal subunits, and even more preferably to the 50S ribosomal subunits.

A compound designed or selected as binding to a ribosome or ribosomal subunit may be further computationally optimized so that in its bound state it would preferably lack repulsive electrostatic interaction with the target enzyme. Such non-complementary (e.g., electrostatic) interactions include repulsive charge-charge, dipole-dipole and charge-dipole interactions. Specifically, the sum of all electrostatic interactions between the inhibitor and the enzyme when the inhibitor is bound to the ribosome or the ribosomal subunit, preferably make a neutral or favorable contribution to the enthalpy of binding. Weak binding compounds will also be designed by these methods so as to determine SAR.

Specific computer software is available in the art to evaluate compound deformation energy and electrostatic interaction. Examples of programs designed for such uses include: Gaussian 92, revision C (M. J. Frisch, Gaussian, Inc., Pittsburgh, Pa.,COPYRGT.1992); AMBER, version 4.0 (P. A. Kollman, University of California at San Francisco, .COPYRGT.1994); QUANTA/CHARMM (Molecular Simulations, Inc., Burlington, Mass. .COPYRGT.1994); and Insight II/Discover (Biosym Technologies Inc., San Diego, Calif. .COPYRGT.1994). These programs may be implemented, for instance, using a Silicon Graphics workstation, IRIS 4D/35 or IBM RISC/6000 workstation model 550. Other hardware systems and software packages will be known to those skilled in the art.

Once an inhibitor of protein synthesis or of a ribosome or ribosomal subunit or any compound that associates with the ribosome or ribosomal subunit has been optimally selected or designed, as described above, substitutions may then be made in some of its atoms or side groups in order to improve or modify its binding properties. Generally, initial substitutions are conservative, i.e., the replacement group will have approximately the same size, shape, hydrophobicity and charge as the original group. It should, of course, be understood that components known in the art to alter conformation should be avoided. Such substituted chemical compounds may then be analyzed for efficiency of fit to the ribosome or ribosomal subunit by the same computer methods described in detail, above.

The present invention further provides a method of obtaining new compounds and agents that interact differentially with the ribosomes or ribosomal subunits from prokaryotes and eukaryotes, more preferably the large ribosomal subunits from prokaryotes and eukaryotes, and even more preferably the 50S ribosomal subunits from prokaryotes. As discussed earlier, the large ribosomal subunit from procaryotes and eucaryotes are structurally conserved. The amino acid sequences of the large ribosomal subunit from procaryotes and eukaryotes can be aligned due to the evolutionary conservation of the identity of amino acid residues that are important for 3-D structure, the nature and shape of the binding sites for substrates and the catalytic site. This similarity in amino acid sequence of the homologous large ribosomal subunit allows the construction of approximate models for the homologues whose crystal structures have not been solved, so-called homology modeling.

The present invention also provides new compounds, ligands and agents that interact with the ribosomes and ribosomal subunits and compositions comprising the new compounds or agents and carriers.

The compounds designed by the above methods are useful for inhibiting protein synthesis and therefore are useful as therapeutic agents to treat and prevent diseases or conditions associated with protein synthesis or to function as pesticides, such as herbicides and insecticides.

E. Uses of the Atomic Coordinates Determined for One Molecule

As discussed earlier, the phase information cannot be measured directly from diffraction patterns. If the crystal being examined contains a macromolecule of unknown structure, additional experiments must be done to determine phases, which are often time consuming and uncertain of success (Blundell and Johnson, supra). Those who choose to work with crystals of molecules of known, or nearly entirely known structure face a much less challenging and time-consuming task. Depending on how close the relationship is between the molecules in their new crystals and those already known, three different approaches can be taken. First, if the new molecule is only slightly different and the crystals it forms are isomorphous to those in which the related molecule was solved, the coordinates deposited for the related molecule can be used to compute phases that can then be combined directly with newly observed amplitudes to obtain maps of the new molecule. Second, if the new molecule is closely related to the old, but crystallizes in a different unit cell with different symmetry, a technique called molecular replacement can be used to obtain useful phases from the coordinates of a related molecule (Blundell and Johnson, supra). Third, if the new molecule diverges significantly from the old, but is still homologous, a model for the new molecule can be generated by homology modeling and that approximate model used to obtain phases by molecular replacement. Provided the computed phases are good enough to get a crudely interpretable image of the new molecule, the numerous techniques that exist for phase extension are likely to make it possible to improve that image considerably. The point is that knowledge of the coordinates of one molecule can greatly facilitate the determination of the structures of related molecules.

F. Use of the Coordinates of the *H. Marismortui* Large Ribosomal Subunit to Determine the Crystal Structure of the Large Subunit of Other Species The coordinates of the large ribosomal subunit from *H. Marismortui* can be used to experimentally determine the structures of the large subunit from other species either as an isolated subunit, in complex with the small subunit or either of these complexed with functionally important ligands such as aminoacylated tRNA, and/or the various protein synthesis factors, such as elongation factor G, elongation factor Tu, termination factor or recycling factor, in both their GTP and GDP conformational states. The *H. marismortui* subunit coordinates can also be used to solve the structures of ribosomal complexes with components of the protein secretion machinery such as signal recognition particle, and the translocon.

These *H. marismortui* coordinates could be used in a variety of ways to solve other large ribosomal subunit containing structures. They could be used to solve the structure of the 70S ribosome (or the large subunit) even at lower resolutions, such as 4.5 to 15 Å resolution. This would utilize a combination of homology modeling and fitting of the homologous structures to the electron density maps, generated either by X-ray crystallography or cryo electron microscopy.

These *H. marismortui* coordinates could be used to solve homologous structures or structures of other complexes using the method of molecular replacement, as implemented in many standard crystallographic packages, such as CNS, for example. In this method the *H. marismortui* subunit structures is positioned in the unit cell of the new crystal by finding the orientation and position that provides the best agreement between observed diffraction amplitudes and those calculated from the coordinates of the positioned subunit. A starting electron density map calculated using 2F(observed)-F (calculated), where F is the diffraction amplitude, and adjusting the model to fit the map. Refinement of the initial model can be done as is standard in the field of macromolecular crystallography.

Any of these new ribosome or large ribosomal subunit structures determined using the *H. marismortui* coordinates can then subsequently be used for structure based drug design using all of the approaches described above.

G. Use of Homology Structure Modeling to Design Ligands that will Bind More Tightly to the Target Enzyme than to the Non-Target Enzyme The present invention contemplates the use of the atomic coordinates and structures of the large ribosomal subunit and its complexes with two substrate analogues to designing modifications to starting compounds, such as puromycin, that will bind more tightly to the target enzyme (e.g., the 50S ribosomal subunit of bacteria) and less tightly to the non-targeted enzyme (e.g., human 60S ribosomal subunit).

The structure of a complex between the large ribosomal subunit and the starting compound (e.g., puromycin or other protein synthesis inhibitors) can also be used to guide the modification of that compound to produce new compounds that have other desirable properties for the applicable industrial and other uses (e.g., as pharmaceuticals, herbicides or insecticides), such as chemical stability, solubility or membrane permeability. Lipinski et al. (1997, Adv. Drug Deliv. Rev., 23:3) provide the 'Rule of Five' probability scheme that estimates oral absorption of the newly synthesized compounds.

Inhibitors of protein synthesis that are known in the art include but are not limited to chloramphenicol, macrolides such as erythromycin, azithromycin, tylosin, carbomycin, and lincomycin, and streptogamins such as virginiamycin, thiostrepton, and anisomycin. Inhibitors can be diffused into or soaked with the stabilized crystals of the large ribosomal subunit as described in Example 3 to form a complex with the large ribosomal subunit for collecting X-ray diffraction data. Alternatively, the inhibitors can be cocrystallized with the large ribosomal subunit by mixing the inhibitor with the large ribosomal subunit before precipitation with high salt.

Starting with the structure of the ribosome from *H. marismortui*, the structure of the ribosome from a non-targeted organism (for example, the human 60S ribosomal subunit) can be constructed by changing the structure of residues at the binding site for a ligand for the residues at the same positions in of the non-target ribosome. The process whereby this modeling is achieved is called homology structure modeling. This is done computationally by removing the side chains from the ribosome of known structure and replacing them by the side chains of the unknown structure put in sterically plausible positions. In this way it can be understood how the shapes of the active site cavities of the targeted and non-targeted ribosomes differ. This process, therefore, provides information concerning how a bound ligand can be chemically altered in order to produce compounds that will bind tightly and specifically to the targeted ribosome but will simultaneously be sterically prevented from binding to the non-targeted ribosome. Likewise, knowledge of portions of the bound ligands that are facing to the solvent would allow introduction of other functional groups for additional pharmaceutical purposes. This same process of homology structure modeling can be used to understand the mechanisms whereby mutant ribosomes become resistant to the effects of pharmaceuticals or pesticides, such as herbicides or insecticides.

The use of homology structure modeling to design molecules (ligands) that bind more tightly to the target enzyme than to the non-target enzyme has wide spread applicability. The method outlined herein can be used to control any targeted organisms by designing ligands which inhibit large ribosomal subunits while failing to inhibit the 50S or 60S ribosomal subunit of the non-targeted organisms to the same extent or not at all. The ligands identified or prepared by the methods of the present invention can be used to control the targeted organisms while causing the non-targeted organism little or no adverse effects. Thus, the ligands identified or developed using the methods of the present invention can be designed so that their administration kills the target organisms or inhibits some aspect of the biological functions of the target organisms while failing to have a similar effect on the non-targeted organism. The adverse effects of the agent on the targeted organisms may include, but are not limited to, death of the target organism; slowing growth rates; slowing or eliminating passage from one growth phase to another (e.g., extending the larval growth stage); slowing or eliminating reproduction, decreasing or preventing mating, decreasing or eliminating offspring production, limiting or eliminating target organism weight gains; decreasing or eliminating feeding ability and behaviors; and disrupting cellular, tissue and/or organ functions.

The present invention contemplates novel agents that interact with ribosomes, more particularly with ribosomal subunits, and even more particularly with large ribosomal subunits, and most particularly with the 50S ribosomal subunit. These novel agents can be obtained by modifying known agents that interact with ribosomes and ribosomal subunits. In one particular embodiment, these agents can be obtained by analyzing the structure of the large ribosomal subunit and the structure of the complex comprising the large ribosomal subunit and a substrate such as CCd-A-Puro, aa-tRNA, or other known agents that interact with the large ribosomal subunit, especially with the 50S ribosomal subunit. The present invention is not limited to these analyses, but include other methods of analyzing and modifying agents wherein such analyses and methods are useful for obtaining novel agents.

In one aspect, the novel agents contemplated by the present invention are useful as herbicides, pesticides (e.g., insecticides, nematocides, rodenticides, etc.), miticides, or antimicrobial agents (e.g., antifungals, antibacterials, antiprotozoals, etc.) to target specific organisms. For example, the novel agents can target animal and plant parasitic nematodes, prokaryotic organisms (disease causing microbes), and eukaryotic multicellular pests. Specific examples. of multicellular pests include, but are not limited to, insects, fungi, bacteria, nematodes, mites and ticks, protozoan pathogens, animal-parasitic liver flukes, and the like.

Cinnamomin is a type II ribosome-inactivating protein purified from the seeds of *Cinnamomum camphora* (camphor tree). Zhou et al. (2000) tested the toxicity of cinnamomin against *Helicoverpa armigera* (bollworm) and *Culex pipines pallens* (mosquito). The tools and methodologies of the present invention can be used to obtain cinnamom derivatives that inhibit the protein synthesis of target insects, such as bollworms and mosquitoes, more than they inhibit the protein synthesis of non-target insects, such as beetles of the family Coccinellidae (e.g., ladybugs) and *Apis mellifera* (honey bees). Other possible target insects include, but are not limited to, insects selected from the orders Coleoptera (beetles), Diptera (flies, mosquitoes), Hymenoptera (wasps, ants, sawflies), Lepidoptera (butterflies and moths), Mallophaga (lice), Homoptera (whiteflies, aphids), Hemiptera (bugs), Orthroptera (locusts, cockroches), Thysanoptera (thrips), Dermaptera (earwigs), Isoptera, Anoplura, Siphonaptera, and Trichoptera (caddis flies).

Herbicides, pesticides, miticides, and antimicrobial agents that inhibit protein synthesis by interacting with ribosomes are known to the skilled artisan. A few examples are discussed below. These known agents can be modified to obtain novel agents by using computer modeling techniques and knowledge of the structure of ribosomes and ribosomal subunits and the structure of ribosome/agent and ribosomal subunit/agent complexes.

Capobianco et al. (2000) report that the novel ketolide ABT-773 binds ribosomes tighter than erythromycin in *S. pneumoniae* and is able to defeat macrolide resistance in bacteria. The tools and methodologies of the present invention can be used to obtain erythromycin derivatives that bind the ribosomes or ribosomal subunits of target bacteria more tightly than they bind the ribosomes and ribosomal subunits of non-target animals. The target bacteria can be any infectious bacteria, particularly *S. pneumoniae*, and even more particularly erythromycin-resistant *S. pneumoniae*. The non-target animals can be any animal, particularly mammals, and even more particularly humans.

Fabra et al. (1993) disclose that 2,4-dichlorophenoxyacetic acid (2,4-D), an herbicide used extensively in agriculture, affects protein synthesis of *Azospirillum brasilense* at the ribosomal level. The tools and methodologies of the present invention can be used to obtain 2,4-D derivatives that inhibit the protein synthesis of target plants more than they inhibit the protein synthesis of non-target plants and animals. The target plants can be any unwanted plant species, particular weeds, and even more particularly noxious weeds. Whether or not a particular plant is considered a weed will depend upon the context in which it is growing. For example, unwanted *Zea mays* (corn) plants growing in a *Glycine max* (soybean) field could be considered unwanted weeds. Examples of weeds which are likely target plants include, but are not limited to, *Allium vineale* (wild garlic), *Bromus tectorum* (downy brome), *Triticum cylindricum* (jointed goatgrass), *Amaranthus spp.* (pigsweed), *Chenopodium album* (lambsquarters), *Avena fatua* (wild oats), *B. secalinus* (cheat), *Echinochloa crus-galli* (barnyardgrass), *Alopecurus myosuroides* (blackgrass), *Setaria faberii* (giant foxtail), *Xanthium strumarium* (common cocklebur), *Ambrosia artemisiifolia* (common ragweed), and *Ipomoea spp.* (morning-glories). The non-target organisms can be any plant, particularly any desirable plant, and even more particularly any crop plant. The non-target organisms can also be any animals, particularly mammals, and even more particularly humans. In one preferred embodiment, the tools and methodologies of the present invention can be used to produce 2,4-D analogs which kill or injure one or more noxious weed species but fail to harm non-target plants and animals.

Fernandez-Puentes et al. (1993) report that ricin inhibits the binding of aminoacyl-tRNA to ribosomes and that similar results were observed with abrin, ricin A chain, abrin A chain, and ricinus aglutinin A chain. The tools and methodologies of the present invention can be used to obtain ricin derivatives that inhibit the binding of aminoacyl-tRNA to the ribosomes or ribosomal subunits of target organisms more than they inhibit the binding of aminoacyl-tRNA to the ribosomes and ribosomal subunits of non-target organisms.

Sonnemann et al. (1991) show that the ribosome of *Dicyostelium discoideum* contains a calmodulin-binding protein. This protein is homologous to rat ribosomal protein L19 of the large ribosomal subunit. Sonnemann et al. propose that $Ca^{++}$ plays a role in regulating protein synthesis. This proposal is supported by the work of Kumar et al. (1991) who demonstrated that calmodulin antagonists inhibited protein synthesis in Ehrlich ascites tumor cells. The tools and methodologies of the present invention can be used to obtain derivatives of calmodulin-binding antagonists that inhibit the protein synthesis of target organisms, such as rats, more than they inhibit the protein synthesis of non-target organisms, such as humans.

Examples of antibiotics that are inhibitors of protein synthesis include but are not limited to puromycin, cycloheximide, chloramphenicol, tetracycline, and streptomycin (Heldt, 1997). Puromycin, as discussed earlier, binds as an analogue of an aminoacyl-tRNA to the A site and participates in all elongation steps, but prevents the formation of a peptide bond, thus terminating protein synthesis in prokaryotes and eukaryotes. Cycloheximide inhibits peptidyl transferase in eukaryotic ribosomes. Chloramphenicol inhibits peptidyl transferase in prokaryotic ribosomes. Tetracycline binds to the 30S subunit and inhibits the binding of aminoacyl-tRNA to prokaryotic ribosomes much more than to eukaryotic ones. Streptomycin interacts with 70S ribosomes which results in an incorrect recognition of mRNA sequences and thus inhibits initiation in prokaryotic ribosomes. U.S. Pat. No. 5,801,153 discloses antibiotics against pathogens. An example of antibacterial antibiotics that inhibit protein synthesis by inference with the activity of ribosomes is aminoglycosides. However, there is a limitation to their use because of their ototoxic and nephrotoxic properties. Amikacin sulfate, Framycetin sulfate, Gentamycin sulfate, Kanamycin sulfate, Neomycin sulfate, Netilmicin sulfate, Paromomycin sulfate, Sissomycin sulfate, Tobramycin, Vancomycin hydrochloride, and Viomycin sulfate are the members of the aminoglycoside family. The tools and methodologies of the present invention can be used to obtain derivatives of any antibiotic of choice so that they inhibit the protein synthesis of target organisms to a greater degree than they inhibit the protein synthesis of non-target organisms, such as humans.

Examples of targeted and non-targeted organisms include, but are not limited to, those provided in Table 4.

TABLE 4

Examples of the types of ligands which may be identified and/or developed by the methods of the present invention and the applicable target/non-target organisms.

| Type of Ligand | Target Organisms | Non-Target Organisms |
| --- | --- | --- |
| Herbicides | Dicotyledonous plants | Monocotyledonous plants |
| Herbicides | Grasses | Soybeans, potatoes, coffee |
| Insecticides | Flies, Mites | Honey bees |
| Pesticides | Ticks | Deer |
| Pesticides | Lice | Birds |

TABLE 4-continued

Examples of the types of ligands which may be identified and/or developed by the methods of the present invention and the applicable target/non-target organisms.

| Type of Ligand | Target Organisms | Non-Target Organisms |
|---|---|---|
| Miticides | Parasitic mites (mange) | Dogs |
| Antimicrobial Agents (Antibacterials) | Streptococcus pneumoniae | Humans |
| Antimicrobial Agents (Antibacterials) | Clostridium difficile | Escherichia coli |
| Antimicrobial Agents (Antifungals) | Etysiphe graminis | Barley |
| Antimicrobial Agents (Antiprotozoals) | Toxoplasma gondii | Animals |
| Poisons | Rats | Dogs cats humans |

Target bacteria of interest include, but are not limited to, *Staphylococcus aureus, Streptococcus pyogenes, Streptococcus agalactiae, Streptococcus bovis, Streptococcus pneumoniae, Moraxella catarrhalis, Neisseria gonorrhoeae, Neisseria menigtidis, Bacillus anthracis, Corynebacterium diphtheriae, Listeria monocytogenes, Erysipelothrix rhusiopathiae, Clostridium perfringens, Clostridium tetani, Clostridium difficile, Eschericia coli, Proteus mirabilis, Psuedomonas aeruginosa, Klebsiella pneumoniae, Haemophilus influenzae, Haemophilus ducreyi, Yersinia pestis, Yersinia enterocolitica, Francisella tularensis, Pasteurella multocida, Vibrio cholerae, Flavobacterium meningosepticum, Pseudomonas mallei, Pseudomonas pseudomallei, Campylobacter jejuni, Campylobacter fetus, Fusobacterium nucleatum, Calymmatobacterium granulomatis, Streptobacillus moniliformis, Legionella pneumophila, Mycobacterium avium-intracellulare, Mycobacterium tuberculosis, Mycobacterium leprae, Treponema pallidum, Treponema pertenue, Borrelia burgdorferi, Borrelia recurrentis, Actinomyces isrealli, Nocardia asteroides, Ureaplasma urealyticum, Mycoplasma pneumoniae, Chlamydia psittaci, Chlamydia trachomatis, Chlamydia pnemoniae, Pneumocystis carinii, Coccidioides immitis, Histoplasma capsulatum, Blastomyces dermatitidis, Paracoccidioides brasiliensis, Sporothrix schenckii, Cryptococcus neoformans*

H. Detecting Protein Synthesis

Once the compound, agent, or chemical entity that interacts with the ribosome or ribosomal subunit, has been designed or identified, it is further characterized as a modulator of protein synthesis or inducer or inhibitor of the functional activity of the ribosome or ribosomal subunit.

The compound can be administered to a whole organism, tissue, organ, organelle, cell, a cellular or subcellular extract, or a purified ribosome preparation and its pharmacological and inhibitory properties can be assayed by determining its inhibition constant ($IC_{50}$) for inhibiting protein synthesis. Incorporation of $^3H$ leucine or $^{35}S$ methionine, or similar experiments can be performed to investigate protein synthesis activity.

A change in the amount or the rate of protein synthesis in the cell in the presence of compound indicates that the compound is a modulator of protein synthesis. A decrease in the rate or the amount of protein synthesis indicates that the compound is a inhibitor of protein synthesis.

I. High Throughput Assays

The power of high throughput screening is utilized to test new compounds which are identified or designed for their ability to interact with a ribosome or ribosomal subunit using the tools and methods of the present invention. For general information on high-throughput screening (see, for example, Devlin, 1998, High Throughput Screening, Marcel Dekker; U.S. Pat. No. 5,763,263). High throughput assays utilize one or more different assay techniques including, but not limited to, those described below.

Immunodiagnostics and Immunoassays. These are a group of techniques used for the measurement of specific biochemical substances, commonly at low concentrations in complex mixtures such as biological fluids, that depend upon the specificity and high affinity shown by suitably prepared and selected antibodies for their complementary antigens. A substance to be measured must, of necessity, be antigenic—either an immunogenic macromolecule or a haptenic small molecule. To each sample a known, limited amount of specific antibody is added and the fraction of the antigen combining with it, often expressed as the bound:free ratio, is estimated, using as indicator a form of the antigen labeled with radioisotope (radioimmunoassay), fluorescent molecule (fluoroimmunoassay), stable free radical (spin immunoassay), enzyme (enzyme immunoassay), or other readily distinguishable label.

Antibodies can be labeled in various ways, including: enzyme-linked immunosorbent assay (ELISA); radioimmuno assay (RIA); fluorescent immunoassay (FIA); chemiluminescent immunoassay (CLIA); and labeling the antibody with colloidal gold particles (immunogold).

Common assay formats include the sandwich assay, competitive or competition assay, latex agglutination assay, homogeneous assay, microtitre plate format and the microparticle-based assay.

Enzyme-linked immunosorbent assay (ELISA). ELISA is an immunochemical technique that avoids the hazards of radiochemicals and the expense of fluorescence detection systems. Instead, the assay uses enzymes as indicators. ELISA is a form of quantitative immunoassay based on the use of antibodies (or antigens) that are linked to an insoluble carrier surface, which is then used to "capture" the relevant antigen (or antibody) in the test solution. The antigen-antibody complex is then detected by measuring the activity of an appropriate enzyme that had previously been covalently attached to the antigen (or antibody).

For information on ELISA techniques, see, for example, Crowther, (1995) ELISA—Theory and Practice (Methods in Molecular Biology), Humana Press; Challacombe & Kemeny, (1998) ELISA and Other Solid Phase Immunoassays—Theoretical and Practical Aspects, John Wiley; Kemeny, (1991) A Practical Guide to ELISA, Pergamon Press; Ishikawa, (1991) Ultrasensitive and Rapid Enzyme Immunoassay (Laboratory Techniques in Biochemistry and Molecular Biology) Elsevier.

Colorimetric Assays for Enzymes. Colorimetry is any method of quantitative chemical analysis in which the concentration or amount of a compound is determined by comparing the color produced by the reaction of a reagent with both standard and test amounts of the compound, often using a colorimeter. A colorimeter is a device for measuring color intensity or differences in color intensity, either visually or photoelectrically.

Standard colorimetric assays of beta-galactosidase enzymatic activity are well known to those skilled in the art (see, for example, Norton et al., (1985) Mol. Cell. Biol. 5, 281-290). A colorimetric assay can be performed on whole cell lysates using O-nitrophenyl-beta-D-galactopyranoside (ONPG, Sigma) as the substrate in a standard colorimetric beta-galactosidase assay (Sambrook et al., (1989) Molecular Cloning—A Laboratory Manual, Cold Spring Harbor Laboratory Press). Automated colorimetric assays are also available for the detection of beta-galactosidase activity, as described in U.S. Pat. No. 5,733,720.

Immunofluorescence Assays. Immunofluorescence or immunofluorescence microscopy is a technique in which an antigen or antibody is made fluorescent by conjugation to a fluorescent dye and then allowed to react with the complementary antibody or antigen in a tissue section or smear. The location of the antigen or antibody can then be determined by observing the fluorescence by microscopy under ultraviolet light.

For general information on immunofluorescent techniques, see, for example, Knapp et al., (1978) Immunofluorescence and Related Staining Techniques, Elsevier; Allan, (1999) Protein Localization by Fluorescent Microscopy—A Practical Approach (The Practical Approach Series) Oxford University Press; Caul, (1993) Immunofluorescence Antigen Detection Techniques in Diagnostic Microbiology, Cambridge University Press. For detailed explanations of immunofluorescent techniques applicable to the present invention, see U.S. Pat. Nos. 5,912,176; 5,869,264; 5,866,319; and 5,861,259.

J. Computer Related Embodiments

An amino acid sequence or nucleotide sequence of a ribosome or ribosomal subunit and/or x-ray diffraction data, useful for computer molecular modeling of ribosomes or a portion thereof, can be "provided" in a variety of mediums to facilitate use thereof. As used herein, "provided" refers to a manufacture, which contains, for example, a ribosome amino acid sequence or nucleotide sequence and/or atomic coordinates derived from x-ray diffraction data of the present invention, e.g., an amino acid or rRNA sequence of a 50S ribosomal subunit, a representative fragment thereof, or a homologue thereof. Such a method provides the amino acid sequence and/or x-ray diffraction data in a form which allows a skilled artisan to analyze and molecular model the three-dimensional structure of a ribosome or ribosomal subunit, including a subdomain thereof.

In one application of this embodiment, a ribosome or ribosomal subunit, or at least one subdomain thereof, amino acid and nucleic acid sequence and/or x-ray diffraction data of the present invention is recorded on computer readable medium. As used herein, "computer readable medium" refers to any medium which can be read and accessed directly by a computer. Such media include, but are not limited to: magnetic storage media, such as floppy discs, hard disc storage medium, and magnetic tape; optical storage media such as optical discs or CD-ROM; electrical storage media such as RAM and ROM; and hybrids of these categories such as magnetic/optical storage media. A skilled artisan can readily appreciate how any of the presently known computer readable mediums can be used to create a manufacture comprising computer readable medium having recorded thereon an amino acid sequence and/or x-ray diffraction data of the present invention.

As used herein, "recorded" refers to a process for storing information on computer readable medium. A skilled artisan can readily adopt any of the presently known methods for recording information on computer readable medium to generate manufactures comprising an amino acid sequence and/or atomic coordinate/x-ray diffraction data information of the present invention.

A variety of data storage structures are available to a skilled artisan for creating a computer readable medium having recorded thereon an amino acid sequence and/or atomic coordinate/x-ray diffraction data of the present invention. The choice of the data storage structure will generally be based on the means chosen to access the stored information. In addition, a variety of data processor programs and formats can be used to store the sequence and x-ray data information of the present invention on computer readable medium. The sequence information can be represented in a word processing text file, formatted in commercially-available software such as WordPerfect and MICROSOFT Word, or represented in the form of an ASCII file, stored in a database application, such as DB2, Sybase, Oracle, or the like. A skilled artisan can readily adapt any number of dataprocessor structuring formats (e.g. text file or database) in order to obtain computer readable medium having recorded thereon the information of the present invention.

By providing computer readable medium having stored thereon a ribosome or ribosomal subunit sequence and/or atomic coordinates based on x-ray diffraction data, a skilled artisan can routinely access the sequence and atomic coordinate or x-ray diffraction data to model a ribosome or ribosomal subunit, a subdomain thereof, mimetic, or a ligand thereof. Computer algorithms are publicly and commercially available which allow a skilled artisan to access this data provided in a computer readable medium and analyze it for molecular modeling and/or RDD (rational drug design). See, e.g., Biotechnology Software Directory, MaryAnn Liebert Publ., New York (1995).

The present invention further provides systems, particularly computer-based systems, which contain the sequence and/or diffraction data described herein. Such systems are designed to do structure determination and RDD for a ribosome or ribosomal subunit or at least one subdomain thereof. Non-limiting examples are microcomputer workstations available from Silicon Graphics Incorporated and Sun Microsystems running UNIX based, Windows NT or IBM OS/2 operating systems.

As used herein, "a computer-based system" refers to the hardware means, software means, and data storage means used to analyze the sequence and/or x-ray diffraction data of the present invention. The minimum hardware means of the computer-based systems of the present invention comprises a central processing unit (CPU), input means, output means, and data storage means. A skilled artisan can readily appreciate which of the currently available computer-based systems are suitable for use in the present invention. A visualization device, such as a monitor, is optionally provided to visualize structure data.

As stated above, the computer-based systems of the present invention comprise a data storage means having stored therein a ribosome or ribosomal subunit or fragment sequence and/or atomic coordinate/x-ray diffraction data of the present invention and the necessary hardware means and software means for supporting and implementing an analysis means. As used herein, "data storage means" refers to memory which can store sequence or atomic coordinate/x-ray diffraction data of the present invention, or a memory access means which can access manufactures having recorded thereon the sequence or x-ray data of the present invention.

As used herein, "search means" or "analysis means" refers to one or more programs which are implemented on the computer-based system to compare a target sequence or target structural motif with the sequence or x-ray data stored within the data storage means. Search means are used to identify fragments or regions of a ribosome or ribosomal subunit which match a particular target sequence or target motif. A variety of known algorithms are disclosed publicly and a variety of commercially available software for conducting search means are and can be used in the computer-based systems of the present invention. A skilled artisan can readily recognize that any one of the available algorithms or implementing software packages for conducting computer analyses can be adapted for use in the present computer-based systems.

As used herein, "a target structural motif," or "target motif," refers to any rationally selected sequence or combination of sequences in which the sequence(s) are chosen based on a three-dimensional configuration or electron density map which is formed upon the folding of the target motif. There are a variety of target motifs known in the art. Protein target motifs include, but are not limited to, enzymic active sites, inhibitor binding sites, structural subdomains, epitopes, functional domains and signal sequences. Similar motifs are known for RNA. A variety of structural formats for the input and output means can be used to input and output the information in the computer-based systems of the present invention.

A variety of comparing means can be used to compare a target sequence or target motif with the data storage means to identify structural motifs or electron density maps derived in part from the atomic coordinate/x-ray diffraction data. A skilled artisan can readily recognize that any one of the publicly available computer modeling programs can be used as the search means for the computer-based systems of the present invention.

K. Integrated Procedures which Utilize the Present Invention

Molecular modeling is provided by the present invention for rational drug design (RDD) of mimetics and ligands of ribosomes and ribosomal subunits of any organism. The drug design paradigm uses computer modeling programs to determine potential mimetics and ligands which are expected to interact with sites on the protein. The potential mimetics or ligands are then screened for activity and/or binding and/or interaction. For ribosome-related mimetics or ligands, screening methods can be selected from assays for at least one biological activity of ribosomes or ribosomal subunits, e.g., protein synthesis, according to known method steps.

The resulting mimetics or ligands provided by the methods of the present invention are useful for treating, inhibiting or preventing the biological activities of target organisms, thereby killing or injuring their growth. Alternatively, the resulting mimetics or ligands provided by the methods of the present invention may be useful for treating, inhibiting or preventing infections in any organism, including animals, particularly including humans.

Thus, the tools and methodologies provided by the present invention may be used in novel procedures for identifying and designing ligands which bind in desirable ways with ribosomes and ribosomal subunits. Basically, the procedures utilize an iterative process whereby ligands are synthesized, tested and characterized. New ligands can be designed based on the information gained in the testing and characterization of the initial ligands and then such newly identified ligands can themselves be tested and characterized. This series of processes may be repeated as many times as necessary to obtain ligands with the desirable binding properties.

The following steps serve as an example of the overall procedure:

1. A biological activity of a ribosome or ribosomal subunit is selected (e.g., protein synthesis).

2. A ligand is identified that appears to be in some way associated with the chosen biological activity (e.g., the ligand may be an inhibitor of protein synthesis). The activity of the ligand may be tested by in vivo and/or in vitro methods.

A ligand of the present invention can be, but is not limited to, at least one selected from a lipid, a nucleic acid, a compound, a protein, an element, an antibody, a saccharide, an isotope, a carbohydrate, an imaging agent, a lipoprotein, a glycoprotein, an enzyme, a detectable probe, and antibody or fragment thereof, or any combination thereof, which can be detectably labeled as for labeling antibodies. Such labels include, but are not limited to, enzymatic labels, radioisotope or radioactive compounds or elements, fluorescent compounds or metals, chemiluminescent compounds and bioluminescent compounds. Alternatively, any other known diagnostic or therapeutic agent can be used in a method of the invention. Suitable compounds are then tested for activities in relationship to a ribosome or ribosomal subunit.

Complexes between the ribosome or ribosomal subunit and ligands are made either by co-crystallization or more commonly by diffusing the small molecule ligand into a subunit crystal. X-ray diffraction data from the complex crystal are measured and a difference electron density map is calculated. This process provides the precise location of the bound ligand on the ribosome or ribosomal subunits. It is enabled by the coordinates of the atomic structure. The difference Fourier is calculated using measure diffraction amplitudes and the phases of these reflections calculated from the coordinates.

3. Using the methods of the present invention, X-ray crystallography is utilized to create electron density maps and/or molecular models of the interaction of the ligand with a ribosome or a ribosomal subunit.

The entry of the coordinates of the ribosome's or ribosomal subunit's proteins and RNAs into the computer programs discussed above results in the calculation of most probable structure of the macromolecule, including overall atomic coordinates of a ribosome, ribosomal subunit or a fragment thereof. These structures are combined and refined by additional calculations using such programs to determine the probable or actual three-dimensional structure of the ribosome, ribosomal subunit or a fragment thereof, including potential or actual active or binding sites of ligands. Such molecular modeling (and related) programs useful for rational drug design of ligands or mimetics, are also provided by the present invention.

4. The electron density maps and/or molecular models obtained in Step 3 are compared to the electron density maps and/or molecular models of a non-ligand containing ribosome or a non-ligand containing ribosomal subunit and the observed/calculated differences are used to specifically locate the binding of the ligand on the ribosome or ribosomal subunit.

5. Modeling tools, such as computational chemistry and computer modeling, are used to adjust or modify the structure of the ligand so that it can make additions or different interactions binds with the ribosome or ribosomal subunit, and thus bind more tightly to the wild-type subunit or one that has developed resistance to a particular pharmaceutical.

The ligand design uses computer modeling programs which calculate how different molecules interact with the various sites of the ribosome, ribosomal subunit, or a fragment thereof. This procedure determines potential ligands or mimetics of a ribosome, ribosomal subunit, or at least one fragment thereof.

The ligand design uses computer modeling programs which calculate how different molecules interact with the various sites of the ribosome, ribosomal subunit, or a fragment thereof. Thus, this procedure determines potential ligands or mimetics of a ribosome, ribosomal subunit, or at least one fragment thereof.

6. The newly designed ligand from Step 5 can be tested for its biological activity using appropriate in vivo or in vitro tests, including the high throughput screening methods discussed above.

The potential ligands or mimetics are then screened for activity relating to a ribosome, ribosomal subunit, or at least a fragment thereof. Such screening methods are selected from assays for at least one biological activity of the native ribosome.

The resulting ligands or mimetics, provided by methods of the present invention, are useful for treating, screening or preventing bacterial infections in animals, such as mammals (including humans) and birds. Mimetics or ligands for a particular ribosome or ribosomal subunit will similarly react with other ribosomes and ribosomal subunits from other species, subgenera or genera of the source organism.

7. Of course, each of the above steps can be modified as desired by those of skill in the art so as to refine the procedure for the particular goal in mind. Also, additional X-ray diffraction data may be collected on ribosomes, ribosome/ligand complexes, ribosomal subunits, and ribosomal subunit/ligand complexes at any step or phase of the procedure. Such additional diffraction data can be used to reconstruct electron density maps and molecular models which may further assist in the design and selection of ligands with the desirable binding attributes.

The actual ribosome-related ligands, complexes or mimetics are crystallized and analyzed using x-ray diffraction. The diffraction pattern coordinates are similarly used to calculate the three-dimensional interaction of a ligand and the ribosome, ribosomal subunit, or a mimetic, in order to confirm that the ligand binds to, or changes the conformation of, a particular site on the ribosome or ribosomal subunit, or where the mimetic has a similar three-dimensional structure to that of a ribosome, ribosomal subunit or a fragment thereof.

In light of the foregoing general discussion, the specific examples presented below are illustrative only and are not intended to limit the scope of the invention. Other generic and specific configurations will be apparent to those persons skilled in the art.

EXAMPLES

Example 1

Preparation of 50S Ribosomal Subunit Crystals

*H. marismortui* (ATCC 43049) was grown as described previously (Ban et al., 1998) on a slightly modified version of ATCC culture medium 1230, which was supplemented with 4.3 g of yeast extract, 5.1 g of Tris, and 3.4 g of glucose per liter. Bacteria were grown at 37° C. to an $OD_{550nm}$ between 1.0 and 2.2. They were harvested by centrifugation, and stored at −80° C. Cells were ruptured using a French press. Ribosomes were prepared from lysates by centrifugation, and subunits were isolated on sucrose gradients (Shevack et al., 1985).

Reverse Extraction

1. Take 1 mg of subunits from a concentrated 50S ribosomal subunit stock (30 mg/ml in 1.2 M KCl, 0.5 M NH4Cl, 20 mM MgCl2, Tris 10 mM, $CdCl_2$ 1 mM, Tris 5 mM, pH 7.5) and mix with ½ vol. of 30% PEG6000 (300 g PEG, 700 ml $H_2O$ to make 1 liter of 30% PEG; filter through 0.2 μm filter)

Leave on ice for 1 to 2 hr.

2. Spin down precipitate ~30 sec. using a desktop centrifuge.
3. Remove supernatant and add 100 ul of RE-buffer: 7% PEG6000, 1.2 M KCl, 0.5 M $NH_4Cl$, 100 mM KAc, 30 mM $MgCl_2$, 10 mM Tris, 10 mM MES (pH 7.5), 1 mM $CdCl_2$.
4. Resuspend pellet at room temperature by pumping up and down with P200 pipette set at 50 ul. Caution: The pellet will tend to stick to the tip. Avoid air bubbles. Resuspended material should appear a little cloudy.
5. Wrap the eppendorf tube in Alu-foil and leave for equilibration at room temperature for 30-60 min.
The solution will be saturated with 50S.
6. Spin down for 2 min. in desk-top centrifuge at room temperature, transfer supernatant to new eppendorf tube.

A little pellet should be found in the tube used for centrifugation. Keep the supernatant at room temperature.
7. Put 8-10 μl of supernatant in the sample well of a sitting drop tray (Charles-Supper). Streak seed one hour later from a seed stock. [Seed stock is prepared by putting previously grown crystals in stabilizing solution buffer A (see below), and then vortexing them violently. To streak seed, a human hair cleaned with water and ethanol and then dried is passed through the vortexed solution and then touched on the new crystallization drop.] Drops should look cloudy. The reservoirs in the sitting drop trays contain 1000 ul of a solution containing 8% PEG6000, 1.2 M KCl, 0.5 M $NH_4Cl$, 100 mM KAc, 6.5 mM HAc (yields pH 5.8), 30 mM $MgCl_2$, and 1 mM $CdCl_2$.
8. Check after one day if seeding succeeded. If yes, let crystals grow for three weeks.

Stabilization Protocol

Buffer A: 1.2 M KCl, 0.5 M $NH_4Cl$, 30 mM $MgCl_2$, 10% PEG6000, 1 mM $CdCl_2$, 100 mM KAc, 10 mM Tris (titrated to final pH 6.1), 30 mM MES.

Buffer B: 1.7 M NaCl, 0.5 M $NH_4Cl$, 30 mM $MgCl_2$, 1 mM $CdCl_2$, 12% PEG6000, 20% EG, 100 mM KAc (tritrated to final pH 5.8 with HAc)

Buffer C: 0.667 M MES, 0.333 M Tris

When crystals have finished growing (after ~3 weeks), each sitting drop chamber is opened by making just a single cut going from the middle and to the edge of the well. Through this narrow slit, 10 ul of buffer A (at room temperature) is added to each drop and 45 ul of Buffer C to each reservoir.

Trays are put in a plastic box with a lid and put in a 16° C. incubator for approximately one day, and then moved to 12° C. for another day. The plastic box is then put in a polystyrene container with a lid and put in the cold room for yet another day. Crystals can be kept like this for a long time, but need to undergo a further changing of buffer prior to any use.

Make the following transition series using buffer A and buffer B (buffer B/buffer A): 1/16, 1/8, 1/4, 1/2, 3/4.

All solutions should be at cold room temperature.

All manipulations of the drops will take place through the narrow slit.

1. Add 40 ul "1/16" to the drop, leave for 15 min.
2. Add 40 ul "1/8" to the drop, leave for 30-60 min.
3. Take out 40 ul from the drop (dump it in the reservoir), add 40 ul "1/4", leave for 30-60 min.
4. Take out 40 ul from the drop (dump it in the reservoir), add 40 ul "1/2", leave for 15 min.
5. Take out 40 ul from the drop (dump it in the reservoir), add 40 ul "3/4", leave for 15 min.
6. Take out 40 ul from the drop (dump it in the reservoir), add 40 ul "B", leave for 15 min.
7. Take out 60-80 ul from the drop (dump it in the reservoir), add 60-80 ul "B", replace reservoirs with 500 ul B.

It's advisable to group the manipulations. For example, work with six drops at a time like this: new tip, remove 40 ul from each of the six drops in a row, new tip, add 40 ul of fresh buffer to each of these drops.

Example 2

Determination of the Crystal Structure of the 50S Ribosomal Subunit

All data, except the two native data sets, were collected at the National Synchrotron Light Source (Brookhaven) from crystals frozen at 100 K, using beamlines X12b and X25 and recorded using a 345 mm MAR imaging plate. For each heavy atom derivative, anomalous diffraction data were collected at the wavelength corresponding to the peak anomalous scattering. The beam size was 100×100 μm for most data collections at X25 and 200×200 μm at beamline X12b. The crystals were aligned along the long axis of the unit cell (570 Å) so that 1.0° oscillations could be used to collect reflections out to a maximum of 2.7 Å resolution at the edge of the MAR detector. At beamline X12b the crystal to detector distances varied between 450.0 mm and 550.0 mm depending on wavelength, crystal quality and beam divergence, and it was chosen so that maximum resolution data could be collected while avoiding overlapping of spots. At beamline X25 the detector was positioned on a rigid platform at 480 mm which allowed data collection to 3.2 Å for iridium and osmium derivatives with the wavelength set at the anomalous edge. Native data to 2.4 Å resolution were collected at the structural biology beamline ID19 of the Advanced Photon Source (Argonne) using a CCD detector (etc.). Data sets were processed by using DENZO and SCALEPACK (Otwinowski et al., 1993).

Heavy atom based phasing was extended to 3.2 Å resolution by combining MIR phases calculated for two different isomorphous groups of data (MIR1 and MIR2, Table 1) with single derivative anomalous dispersion (SAD) phases. The best two derivatives were osmium pentamine and iridium hexamine, each of which contained a large number of binding sites (Table 1). Several other derivatives with smaller number of sites further improved map quality. All phasing was done by maximum likelihood method implemented in CNS (Brunger et al., 1998) with the exception of the $Ta_6Br_{12}$ derivative, which was refined in SHARP (de la Fortelle et al., 1997) represented as spherically averaged electron density (Table 1). Phases were improved and extended from 3.3 Å to 2.4 Å by solvent flipping (Abrahams et al., 1996) and models were built.

Complete atomic coordinates for 23S and 5S rRNAs, and backbone coordinates for the 27 proteins were deposited on Jul. 10, 2000, at the RCSB Protein Data Bank. The accession number is PDB ID: 1FFK.

Example 3

Preparation of Crystals of 50S Ribosomal Subunit/Puromycin Complex and Collection of X-ray Diffraction Data Crystals of 50S ribosomal subunits were grown and stabilized as described earlier. CCdA-p-puromycin (FIG. 9A) was a generous gift from Michael Yarus (Welch, Chastang et al., 1995). Oligonucleotides from amino-N-acylated minihelices (FIG. 9B) were synthesized by Dharnacon. (Following deprotection, oligonucleotides were briefly heated to 100° C. and snap-cooled on ice to reanneal). Ribosomal 50S subunit crystals were stabilized and then soaked for 24 hours in stabilization buffer plus 100 µM CCdA-p-puromycin or amino-N-acylated mini-helices prior to cryovitrification in liquid propane and X-ray diffraction data collection.

Phases were calculated by density modification (CNS) beginning with the best experimental phases using 2Fo(analogue)-Fo(native) for amplitudes, from 60.0 to 3.2 Å. (Native amplitudes were from the most isomorphous native 1 data set, except for those amplitudes which were present only in the more complete native 2 data set. Calculated 2Fo-Fo amplitudes which were less than twice the corresponding calculated a were replaced by Fo(analogue)). Maps were then calculated using phases from density modified and 2Fo(analogue)-Fo(native) or Fo(analogue)-Fo(native) amplitudes.

The atomic coordinates were deposited on Jul. 26, 2000, at the RCSB Protein Data Bank with the accession numbers PDB ID: 1FFZ (50S ribosomal/CCdA-p-Puro complex) and PDB ID: 1FG0 (50 ribosomal/aa-tRNA analogue complex).

Example 4

The Binding Site for Antibiotics Located in the Tunnel Near to the Peptidyl Transfer Center.

Crystalline complexes of the H. marismortui large subunit complexed with three antibiotics have been established at about 4.5 Å resolution. The electron density maps at this resolution have allowed us to position approximately on the ribosome the known coordinates of the antibiotics tylosin, carbomycin and anisomycin. We observed that these antibiotics all bind in the polypeptide exit tunnel in the region that lies between the peptidyl transferase center as defined by the Yarus inhibitor, CCdA-p-puromycin, and the tips of the proteins L22 and L4 at the point that they form a small orifice in the tunnel. The general location of this major antibiotic binding site is shown in FIG. 19. These antibiotics appear to function by blocking the exit of newly synthesized polypeptides.

The antibiotic erythromycin would be expected to bind in a similar location because of its structural similarities to tylosin and because erythromycin resistance mutations are known in both the tip of protein L4 and in portions of the RNA near the Yarus inhibitor binding site.

The vast majority of the interactions between the antibiotics and the ribosome are through rRNA that forms on the surface of the tunnel in this region between the peptidyl transferase center and protein L22. Since these antibiotics do not bind identically to this region, there will be many additional ways that small molecule compounds can be designed to bind in this region using the tools and methodologies of the present invention. By connecting together components of each of the different antibiotics which bind to non-overlapping sites it will be possible to create new antibiotics. Based on new principles of small molecule RNA interaction shown by these antibiotic complexes we will be able to design small molecules that will bind to sites on the ribosome as well as other potential RNA targets.

It should be understood that the foregoing discussion and examples merely present a detailed description of certain preferred embodiments. It therefore should be apparent to those of ordinary skill in the art that various modifications and equivalents can be made without departing from the spirit and scope of the invention. All journal articles, other references, patents, and patent applications that are identified in this patent application are incorporated by reference in their entirety.

REFERENCES FOR WHICH A COMPLETE CITATION IS NOT PROVIDED IN THE TEXT OF THE SPECIFICATION

Abrahams et al., Acta Cryst. D52, 30-42 (1996).
Agrawal et al., Science, 271, 1000-1002 (1996).
Agrawal et al., J. Biol. Chem. 274, 8723-8729 (1999).
Agrawal et al., Proc. Natl. Acad. Sci. USA 95, 6134-6138 (1998).
Ban et al., Cell 93, 1105-1115 (1998).
Ban et al., Science submitted 6/28/00 (2000).
Ban et al., Nature 400, 841-847 (1999).
Barta et al., Proc. Nat. Acad. Sci. USA 81, 3607-3611 (1984).
Beckmann et al., Science 278, 2123-2128 (1997).
Bennett, Jr. et al., Proc. Natl. Acad. Sci., USA 75, 4848-4852 (1978).
Berger, Mol Gen Genet 155(1), 35-40 (1977).
Bemabeu et al., Proc. Nat. Acad. Sci. 79, 3111-3115 (1982).
Blobel et al., J. Cell. Biol. 45, 130-145 (1970).
Blow et al., Nature 221, 337-340 (1969).
Brunger et al., Acta Cryst. D 54, 905-921 (1998).
Capel et al., Science, 238, 1403-1406 (1987).

Capobianco et al., *Antimicrob Agents Chemother* 44(6), 1562-1567 (2000).
Cate et al., *Science* 285, 2095-2104 (1999).
Chothia et al., *Nature* 256, 705-708 (1975).
Clemons, Jr., et al., *Nature* 400, 833-840 (1999).
Conn et al., *Science* 284, 1171-1174 (1999).
Cooperman, in Ribosomes (University Park Press, Baltimore, 1980) pp. 531-554.
Correll et al., *Proc. Natl. Acad. Sci. USA* 95, 13436-13441 (1998).
Correll et al., *Cell* 91, 705-712 (1997).
Culver et al., *Science* 285, 2133-2135 (1999).
Davies et al., *Structure* 4, 55-66 (1996).
de La Fortelle, *Meth. Enzymol.* 276, 472-494 (1997).
Dobberstein, personal communcation.
Dube et al., *Structure* 6, 389-399 (1998).
Fabra et al., *Toxicology* 83(1-3), 19-29 (1993).
Fernandez-Puentes et al., *Biochemistry* 15(20), 4364-4349 (1976).
Ferre-D'Amare et al., *Nature* 395, 567-574 (1998).
Franceschi et al., *J. Biol. Chem.* 265, 6676-6682 (1990).
Frank et al., *Nature* 376, 441-444 (1995).
Frank et al., *Biochem. Cell Biol.* 73, 757-765 (1995).
Freer et al., *Biochem.* 9, 1997-2009 (1970).
Garrett et al., *The Ribosome: Structure, Function, Antibiotics and Cellular Interactions* (2000)
Garrett et al., in *Ribosomal RNA*. (CRC Press, Boca Raton, 1996) pp. 327-355.
Gerbi, in *Ribosomal RNA*. (CRC Press, Boca Raton, Fla., 1995) pp 71-88.
Golden et al., *EMBO J.* 12, 4901-4908 (1993).
Green et al., *Annu. Rev. Biochem.* 66, 679-716 (1997).
Guerrier-Takada et al., Cell 35, 849-857, (1983).
Gutell et al., in preparation (2000)
Gutell, in *Ribosomal RNA*. (CRC Press, Boca Raton, Fla., 1996) pp. 111-128.
Heldt, *Plant Biochemistry and Molecular Biology* 21.2, 458-464 (1996).
Henderson et al., *Cold Spring Harbor Symp. Quant. Biol.* 36, 63-70 (1971).
Khaitovich et al., *Proc. Natl. Acad. Sci. USA* 96, 85-90 (1999).
Khaitovich et al., *RNA* 5, 605-608 (1999).
Kim et al., *Molec. Cell* 4, 859-864 (1999).
Koshland, Jr., *Cold Spring Harbor Symp. Quant. Biol.* 28, 473-489 (1963).
Kruger et al., *Cell* 31, 147-157, (1982).
Lee et al., *J. Mol. Biol.* 55, 379-400 (1971).
Leffers et al., *J. Mol. Biol.* 195, 43-61 (1987).
Leijonmarck et al., *Nature* 286, 824-826 (1980).
Maden et al., *J. Mol. Biol.* 35, 333-345 (1968).
Mao et al., *Nature Struct. Biol.* 6, 1139-1147 (1999).
Markus et al., *Nature Struct. Biol.* 4, 70-77 (1997).
Maskowski et al., *J. Mol. Biol.*, 193, 818-822, 1987.
Matthews et al., *J. Biol. Chem.* 250, 7120-7126 (1975).
May et al., 1992. *EMBO*, 11, 373-378, 1992.
Milligan et al., *Nature* 319, 693-695 (1986).
Moazed et al., *Proc. Natl. Acad. Sci. USA* 88, 3725-3728, (1991).
Moazed et al., *Nature* 334, 362-364 (1988).
Moazed et al., *Cell* 57, 585-597 (1989).
Moazed et al., *Nature* 342, 142-148 (1989).
Moller et al., "Structure, Function, and Genetics of Ribosomes", 1986
Monro, *J. Mol. Biol.* 26, 147-151 (1967).
Monro et al., *Nature* 222, 356-358 (1969).
Moore, *Annu. Rev. Biochem.* 67, 287-300 (1999).
Moore in *Ribosomal RNA*, (CRC Press, Boca Raton, Fla.) pp. 199-236 (1995).
Moore, *Annu. Rev. Biophys.* 27, 35-58 (1998).
Mueller et al., *J. Mol. Biol.* 298, 35-59 (2000).
Muth et al., Science etc. (2000).
Naharo et al., *Science* 287, 1493-1497 (2000)
Nakagawa et al., *EMBO J.* 18, 1459-1467 (1999).
Nikonov et al., *EMBO J.* 15, 1350-1359 (1996).
Nissen et al., *Science* in preparation (2000).
Nitta et al., *Science* 281, 666-669 (1998).
Nitta et al., *RNA* 4, 257-267 (1998).
Noller, *Ann. Rev. Biochem.* 53, 119-162, (1984).
Noller, *Ann. Rev. Biochem.* 60, 191-227 (1991).
Noller et al., *Science* 256, 1416-1419 (1992).
Noller et al., *The Ribosome. Structure, Function & Evolution* (1990).
Oakes et al., *Structure, Function and Genetics of Ribosomes*, (1986).
Ofengand, *Ribosomes. Structure, Function and Genetics* (1980).
Ostergaard et al., *J. Mol. Biol.* 284, 227-240 (1998).
Otwinowski, *Data Collection and processing*, (1993).
Picking et al., *Biochemistry* 31, 2368-2375 (1992).
Puglisi et al., *Nat. Struct. Biol.* 4, 775-778 (1997).
Rapoport et al., *EMBO J.* (2000).
Ryabova et al., *FEBS Letters* 226, 255-260, (1988).
Rychlik, *Biochim. Biophys.* Acta 114, 425 (1966).
Saenger, *Principles of Nucleic Acid Structure*. (Springer-Verlag, N.Y., 1984).
Schlunzen et al., Biochem. Cell Biol., 73, 739-749 (1995).
Shevack et al., *FEBS Lett.* 184, 68-71 (1985).
Sonnemann et al., *J Biol Chem* 266(34), 23091-23096 (1991).
Stark et al., *Structure*, 3, 815-821 (1995).
Stark et al., *Cell* 100, 301-309 (2000).
Stark et al., *Cell*, 28, 19-28 (1997b).
Stark et al., *Nature*, 3898, 403-406 (1997a).
Steitz et al., *Ann. Rev. Biophys. Bioeng.* 11, 419-444 (1982).
Stoeffler et al., *Structure, Function, and Genetics of Ribosomes* (1986).
Symanski et al., *Nucl. Acids Res.* 26, 156-159 (1998).
Szewczak et al., *J. Mol. Biol.* 247, 81-98 (1995).
Tocilj et al., *Proc. Natl. Acad. Sci. USA* 96, 14252-14257 (1999).
Trakanov et al., *FEBS Lett.* 220, 319-322 (1987).
Traut et al., J. Mol. Biol. 10, 63-(1964).
Tronrud, *Macromolecular Crystallography, Part B, Methods In Enzymology* (1997).
Unge et al., *Structure* 6, 1577-1586 (1998).
Van Bohlen, J. Mol. Biol., 222, 11-15 (1991).
Vester et al., *EMBO J.* 7, 3577-3587 (1988).
Wahl et al., *EMBO J.* 19, 807-818 (2000).
Walleczek et al., *EMBO J.* 7, 3571-3576 (1988).
Ware et al., *Nucl. Acids. Res.* 22, 7795-7817 (1983).
Weinstein et al., *J. of Structural Biology*, 127, 141-151 (1999).
Welch et al., *Biochemistry* 34, 385-390 (1995).
Welch et al., *Biochemistry* 36, 6614-6623 (1997).
Westhof, V. Fritsch, *Structural* 8, R55-R65 (2000).
Wilson et al., *Proc. Nat. Acad. Sci. USA* 83, 7251-7255 (1986).
Wimberly et al., *Cell* 97, 491-502 (1999).
Wittmann-Liebold et al., *The Ribosome. Structure, Function, & Genetics*, (1990).
Wittmann-Liebold, *Structure, Function, and Genetics of Ribosomes*, (1986).
Wittmann-Liebold et al., *The Ribosome*. (1990).
Wool et al., *TIBS* 17, 266-269 (1992).
Wool et al., *Biochem. Cell Biol.* 73, 933-947 (1995).
Xu et al., *J. Struct. Biol.* 124, 129-141 (1998).
Yonath et al., *Biochem. Internat.* 1, 428-435 (1980).
Yonath et al., *Science* 236, 813-816 (1987).
Zhaug et al., *Chem. Biol.* 5, 539-553 (1998).
Zhou et al., *Insect Biochem Mol Biol* 30(3), 259-264 (2000)

We claim:

1. A method of growing a crystal of a 50S ribosomal subunit from *Haloarcula marismortui* comprising:
   (a) isolating a 50S ribosomal subunit from *Haloarcula marismortui*;
   (b) precipitating the 50S ribosomal subunit;
   (c) back-extracting or resuspending the precipitated 50S ribosomal subunit to obtain a solution;
   (d) seeding the back-extracted or resuspended solution of step (c);
   (e) growing a crystal of the 50S ribosomal subunit from the seeded solution of step (d) by vapor diffusion at room temperature;
   (f) harvesting the crystal from step (e);
   (g) stabilizing the harvested crystal by gradual transfer of said crystal into a series of solution containing high salt concentration of from about 1.2 M to 1.7 M; and
   (h) maintaining the crystal under high salt concentration, wherein the crystal (i) is untwinned, (ii) has an average thickness greater than about 15 μm, and (iii) diffracts X-rays to a resolution of at least 2.7 Å.

2. The method of claim 1 further comprising:
   (i) flash freezing the crystal of step (h).

\* \* \* \* \*

SEQUENCE LISTING

```
<160> NUMBER OF SEQ ID NOS: 1
<210> SEQ ID NO 1
<211> LENGTH: 33
<212> TYPE: RNA
<213> ORGANISM: Artificial sequence
<220> FEATURE:
<223> OTHER INFORMATION: Oligonucleotide of puromycin

<400> SEQUENCE: 1
ccggcgggcu gguucaaacc ggcccgccgg acc                           33
```